(12) United States Patent
Fraser et al.

(10) Patent No.: US 9,295,718 B2
(45) Date of Patent: *Mar. 29, 2016

(54) TOLEROGENIC SYNTHETIC NANOCARRIERS TO REDUCE IMMUNE RESPONSES TO THERAPEUTIC PROTEINS

(75) Inventors: Christopher Fraser, Arlington, MA (US); Takashi Kei Kishimoto, Lexington, MA (US); Roberto A. Maldonado, Jamaica Plain, MA (US)

(73) Assignee: Selecta Biosciences, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/458,067

(22) Filed: Apr. 27, 2012

(65) Prior Publication Data

US 2012/0276109 A1 Nov. 1, 2012

Related U.S. Application Data

(60) Provisional application No. 61/480,946, filed on Apr. 29, 2011, provisional application No. 61/513,514, filed on Jul. 29, 2011, provisional application No. 61/531,147, filed on Sep. 6, 2011, provisional application No. 61/531,153, filed on Sep. 6, 2011, provisional application No. 61/531,164, filed on Sep. 6, 2011, provisional application No. 61/531,168, filed on Sep. 6, 2011, provisional application No. 61/531,175, filed on Sep. 6, 2011, provisional application No. 61/531,180, filed on Sep. 6, 2011, provisional application No. 61/531,194, filed on Sep. 6, 2011, provisional application No. 61/531,204, filed on Sep. 6, 2011, provisional application No. 61/531,209, filed on Sep. 6, 2011, provisional application No. 61/531,215, filed on Sep. 6, 2011.

(51) Int. Cl.

| A61K 47/48 | (2006.01) |
|---|---|
| A61K 39/00 | (2006.01) |
| A61K 38/38 | (2006.01) |
| A61K 9/16 | (2006.01) |
| A61K 39/36 | (2006.01) |
| B82Y 5/00 | (2011.01) |
| A61K 9/127 | (2006.01) |
| A61K 9/51 | (2006.01) |

(52) U.S. Cl.
CPC ............. *A61K 39/0005* (2013.01); *A61K 9/127* (2013.01); *A61K 9/5115* (2013.01); *A61K 9/5146* (2013.01); *A61K 38/38* (2013.01); *A61K 39/00* (2013.01); *A61K 39/36* (2013.01); *A61K 47/48861* (2013.01); *A61K 47/48884* (2013.01); *A61K 47/48915* (2013.01); *B82Y 5/00* (2013.01); *A61K 2039/55511* (2013.01); *A61K 2039/577* (2013.01); *A61K 2039/6093* (2013.01)

(58) Field of Classification Search
CPC ..... A61K 39/00; A61K 38/38; A61K 39/005; A61K 9/127; A61K 9/1647; A61K 47/48853; A61K 47/48884; A61K 47/48892; A61K 47/48915; A61K 47/48953; A61K 47/48907; A61K 9/5115; A61K 9/5146; A61K 2039/577; A61K 2039/6093; A61K 2039/62; A61K 2300/00; B82Y 5/00

See application file for complete search history.

(56) References Cited

U.S. PATENT DOCUMENTS

| 5,543,158 A | 8/1996 | Gref et al. |
|---|---|---|
| 5,578,325 A | 11/1996 | Domb et al. |
| 5,679,347 A | 10/1997 | Porcelli et al. |
| 5,762,904 A | 6/1998 | Okada et al. |
| 5,912,017 A | 6/1999 | Mathiowitz et al. |
| 5,928,647 A | 7/1999 | Rock |
| 6,007,845 A | 12/1999 | Domb et al. |
| 6,060,082 A | 5/2000 | Chen et al. |
| 6,197,229 B1 | 3/2001 | Ando et al. |
| 6,254,890 B1 | 7/2001 | Hirosue et al. |
| 6,306,640 B1 | 10/2001 | Nicolette |
| 6,387,397 B1 | 5/2002 | Chen et al. |
| 6,800,296 B1 | 10/2004 | Langer et al. |
| 6,881,421 B1 | 4/2005 | da Silveira et al. |
| 7,550,441 B2 | 6/2009 | Farokhzad et al. |
| 7,727,969 B2 | 6/2010 | Farokhzad |
| 8,367,113 B2 | 2/2013 | Gu et al. |
| 8,629,151 B2 | 1/2014 | Zepp et al. |
| 8,652,487 B2 | 2/2014 | Maldonado et al. |
| 2002/0086049 A1 | 7/2002 | Bolton et al. |
| 2004/0043483 A1 | 3/2004 | Qian et al. |
| 2004/0141958 A1 | 7/2004 | Steinaa et al. |
| 2004/0247680 A1 | 12/2004 | Farokhzad et al. |
| 2005/0037075 A1 | 2/2005 | Farokhzad et al. |
| 2006/0002852 A1 | 1/2006 | Saltzman et al. |

(Continued)

FOREIGN PATENT DOCUMENTS

| CN | 101437491 A | 5/2009 |
|---|---|---|
| CN | 101646418 A | 2/2010 |

(Continued)

OTHER PUBLICATIONS

Ashe et al., Mol Genet Metab 100: 309-315, ePub May 10, 2010.*

(Continued)

*Primary Examiner* — Phuong Huynh
(74) *Attorney, Agent, or Firm* — Wolf, Greenfield & Sacks, P.C.

(57) ABSTRACT

Disclosed are synthetic nanocarrier compositions, and related methods, comprising therapeutic protein APC presentable antigens and immunosuppressants that provide tolerogenic immune responses specific to therapeutic proteins.

14 Claims, 8 Drawing Sheets

(56) References Cited

U.S. PATENT DOCUMENTS

| | | |
|---|---|---|
| 2006/0147432 A1 | 7/2006 | Moore et al. |
| 2006/0159766 A1 | 7/2006 | Jenkins et al. |
| 2006/0210638 A1 | 9/2006 | Liversidge et al. |
| 2006/0222652 A1 | 10/2006 | Sebbel et al. |
| 2006/0251677 A1 | 11/2006 | Bachmann et al. |
| 2006/0251710 A1 | 11/2006 | Kwon et al. |
| 2006/0269540 A1 | 11/2006 | Robert et al. |
| 2008/0031899 A1* | 2/2008 | Reddy et al. ............ 424/277.1 |
| 2008/0044484 A1 | 2/2008 | Minev |
| 2008/0064859 A1 | 3/2008 | Vandenbark et al. |
| 2008/0081074 A1 | 4/2008 | Gu et al. |
| 2008/0145441 A1 | 6/2008 | Penades et al. |
| 2008/0160089 A1 | 7/2008 | Vitiello et al. |
| 2008/0254045 A1 | 10/2008 | Donda et al. |
| 2008/0268063 A1 | 10/2008 | Jon et al. |
| 2008/0311140 A1 | 12/2008 | Lee et al. |
| 2009/0004259 A1 | 1/2009 | Rabinovich et al. |
| 2009/0028910 A1 | 1/2009 | DeSimone et al. |
| 2009/0074828 A1 | 3/2009 | Alexis et al. |
| 2009/0155292 A1 | 6/2009 | Santamaria et al. |
| 2009/0226525 A1 | 9/2009 | de los Rios et al. |
| 2009/0298710 A1 | 12/2009 | Farokhzad et al. |
| 2010/0008932 A1 | 1/2010 | Bensussan et al. |
| 2010/0055076 A1 | 3/2010 | Lim et al. |
| 2010/0055189 A1 | 3/2010 | Hubbell et al. |
| 2010/0062968 A1 | 3/2010 | Pulendran et al. |
| 2010/0068261 A1 | 3/2010 | Tamarkin et al. |
| 2010/0080816 A1 | 4/2010 | Hadeiba et al. |
| 2010/0099613 A1 | 4/2010 | Buyse et al. |
| 2010/0111993 A1 | 5/2010 | Tureci et al. |
| 2010/0129392 A1 | 5/2010 | Shi et al. |
| 2010/0129439 A1 | 5/2010 | Alexis et al. |
| 2010/0151000 A1 | 6/2010 | Thomas et al. |
| 2010/0172994 A1 | 7/2010 | Sigmund et al. |
| 2010/0183602 A1 | 7/2010 | Carballido Herrera et al. |
| 2010/0183727 A1 | 7/2010 | Iannacone et al. |
| 2010/0189742 A1 | 7/2010 | Van Der Burg et al. |
| 2010/0203142 A1 | 8/2010 | Zhang et al. |
| 2010/0233197 A1 | 9/2010 | Wakatsuki Pedersen et al. |
| 2010/0233251 A1* | 9/2010 | Von Andrian et al. ......... 424/450 |
| 2010/0303850 A1 | 12/2010 | Lipford et al. |
| 2010/0323199 A1 | 12/2010 | Gu et al. |
| 2011/0020388 A1 | 1/2011 | Zepp et al. |
| 2011/0027217 A1 | 2/2011 | Zepp et al. |
| 2011/0052697 A1 | 3/2011 | Farokhzad et al. |
| 2011/0070153 A1 | 3/2011 | Hyde et al. |
| 2011/0070154 A1 | 3/2011 | Hyde et al. |
| 2011/0076273 A1 | 3/2011 | Adler et al. |
| 2011/0110965 A1 | 5/2011 | Fraser et al. |
| 2011/0171248 A1 | 7/2011 | Pittet et al. |
| 2011/0223201 A1 | 9/2011 | Lipford et al. |
| 2011/0262491 A1 | 10/2011 | Keegan et al. |
| 2011/0272836 A1 | 11/2011 | Keegan et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2012/0027806 A1 | 2/2012 | Ilyinskii et al. |
| 2012/0058153 A1 | 3/2012 | Ilyinskii et al. |
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0114677 A1 | 5/2012 | Zepp et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1 | 11/2012 | Fraser et al. |
| 2012/0276155 A1 | 11/2012 | Kishimoto et al. |
| 2012/0276156 A1 | 11/2012 | Fraser et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2013/0028857 A1 | 1/2013 | Gao et al. |
| 2013/0028941 A1 | 1/2013 | Altreuter et al. |
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado et al. |
| 2013/0059009 A1 | 3/2013 | Kishimoto et al. |
| 2014/0030344 A1 | 1/2014 | Zepp et al. |
| 2014/0193453 A1 | 7/2014 | Zepp et al. |
| 2014/0199340 A1 | 7/2014 | Maldonado |
| 2014/0242173 A1 | 8/2014 | Zepp et al. |
| 2014/0328854 A1 | 11/2014 | Maldonado et al. |
| 2014/0328921 A1 | 11/2014 | Maldonado |
| 2014/0328922 A1 | 11/2014 | Maldonado |
| 2014/0328923 A1 | 11/2014 | Maldonado et al. |
| 2014/0328924 A1 | 11/2014 | Kishimoto |
| 2014/0356361 A1 | 12/2014 | Maldonado et al. |

FOREIGN PATENT DOCUMENTS

| | | |
|---|---|---|
| CN | 101861165 A | 10/2010 |
| EP | 1 153 122 A2 | 11/2001 |
| EP | 1 932 538 A1 | 6/2008 |
| GB | PCT/GB2010/000710 | * 10/2010 |
| WO | WO 95/22963 A1 | 8/1995 |
| WO | WO 96/20698 A2 | 7/1996 |
| WO | WO 99/22762 A1 | 5/1999 |
| WO | WO 99/34826 A1 | 7/1999 |
| WO | WO 00/32626 A1 | 6/2000 |
| WO | WO 2004/0985092 A2 | 11/2004 |
| WO | WO 2007/001448 A2 | 1/2007 |
| WO | WO 2007/068747 A1 | 6/2007 |
| WO | WO 2007/070682 A2 | 6/2007 |
| WO | WO 2007/087341 A2 | 8/2007 |
| WO | WO 2007/098254 A2 | 8/2007 |
| WO | WO 2007/133807 A2 | 11/2007 |
| WO | WO 2007/137117 A2 | 11/2007 |
| WO | WO 2007/144150 A1 | 12/2007 |
| WO | WO 2007/150030 A2 | 12/2007 |
| WO | WO 2008/019142 A2 | 2/2008 |
| WO | WO 2008/036374 A2 | 3/2008 |
| WO | WO 2008/043157 A1 | 4/2008 |
| WO | WO 2008/071774 A1 | 6/2008 |
| WO | WO 2008/105773 A2 | 9/2008 |
| WO | WO 2008/124632 A1 | 10/2008 |
| WO | WO 2008/124634 A1 | 10/2008 |
| WO | WO 2008/124639 A2 | 10/2008 |
| WO | WO 2008/129020 A1 | 10/2008 |
| WO | WO 2008/147456 A2 | 12/2008 |
| WO | WO 2008/150868 A1 | 12/2008 |
| WO | WO 2009/022154 A2 | 2/2009 |
| WO | WO 2009/051837 A2 | 4/2009 |
| WO | WO 2009/106999 A2 | 9/2009 |
| WO | WO 2009/131712 A2 | 10/2009 |
| WO | WO 2009/145238 A1 | 12/2009 |
| WO | WO 2010/018384 A1 | 2/2010 |
| WO | WO 2010/037402 A1 | 4/2010 |
| WO | WO 2010/042863 A1 | 4/2010 |
| WO | WO 2010/042870 A1 | 4/2010 |
| WO | WO 2010/047839 A1 | 4/2010 |
| WO | WO 2010/085509 A1 | 7/2010 |
| WO | WO 2010/116141 A2 | 10/2010 |
| WO | WO 2010/123569 A2 | 10/2010 |
| WO | WO 2010/138192 A2 | 12/2010 |
| WO | WO 2010/138193 A2 | 12/2010 |
| WO | WO 2010/138194 A2 | 12/2010 |
| WO | WO 2011/005850 A1 | 1/2011 |
| WO | WO 2011/033090 A1 | 3/2011 |
| WO | WO 2011/109833 A2 | 9/2011 |
| WO | WO 2012/019041 A2 | 2/2012 |
| WO | WO 2012/054920 A2 | 4/2012 |

(56) References Cited

FOREIGN PATENT DOCUMENTS

OTHER PUBLICATIONS

Witkowski et al., Biochemistry 38(36): 11643-50, Sep. 7, 1999.*
Colman et al., in Research in Immunology (145(1):33-36, 1994.*
Wu et al., J Mol Biol 294: 151-162, 1999.*
Dobrovoskaia et al., Nature nanotechnology 2: 469-478, 2007.*
Bawarski et al., Nanomedicine 4: 273-282, 2008.*
Seffernick et al., J Bacteriol 183 (8): 2405-10, Apr. 2001.*
Gao et al., American J Transplantation 7:1722-1732, 2007.*
Mason et al., Molecular Endocrinology 8(3): 325-332, 1994.*
Skolnick et al., Trends in Biotechnology, 18: 34-39, 2000.*
Jones et al., Pharmacogenomics Journal, 1:126-134, 2001.*
Tosatto et al., Current Pharmaceutical Design, 12:2067-2086, 2006.*
Fifis et al., J Immunology 173: 3148-3154, 2004.*
Mottram et al., Molecular Pharmaceutics 4(1): 73-84, 2007.*
Miyara et al., J allergy Clin Immunol 123(4): 749-755, Apr. 2009.*
Witkowski et al., Biochemistry. 38(36): 11643-50, Sep. 7, 1999.*
Shimizu et al., Circulation 108:2113-2120, 2003.*
Imamura et al., Thorax 64: 44-49, 2009.*
Suzuki et al., Human Immunol 69(11): 781-789, 2008.*
Menzies et al., J Allergy Clin Immunol 119: 328-335, 2007.*
Chayen et al., Lysosomal enzymes and inflammation with particular reference to rheumatoid diseases. Ann Rheum Dis. Sep. 1971;30(5):522-36.
Katsnelson, Next-generation proteasome inhibitor approved in multiple myeloma. Next-generation proteasome inhibitor approved in multiple myeloma. Nat Biotechnol. Nov. 2012;30(11):1011-2. doi: 10.1038/nbt1112-1011.
Lutsiak et al., Analysis of poly(D,L-lactic-co-glycolic acid) nanosphere uptake by human dendritic cells and macrophages in vitro. Pharm Res. Oct. 2002;19(10):1480-7.
Meng et al., Statins induce the accumulation of regulatory T cells in atherosclerotic plaque. Mol Med. May 9, 2012;18:598-605. doi: 10.2119/molmed.2011.00471.
Orban et al., Prevention of Type 1 Diabetes Mellitus using a Novel Vaccine. Ther Adv Endocrinol Metab. Feb. 2011;2(1):9-16.
[No Author Listed] Autologous Dendritic Cell Therapy for Type 1 Diabestes Suppression: A Safety Study. Clinical Trials. Mar. 2007. Last accessed Jan. 5, 2012 available at http://www.clinicaltrials.gov/ct2/show/NCT00445913?term=dendritic &cond=%22Autoimmune+Diseases%22&rank=4. 5 pages.
[No Author Listed] Autologous Tolerogenic Dendritic Cells for Rheumatoid Arthritis (AutoDECRA). Clinical Trials. May 2011. Last accessed Jan. 5, 2012 available at http://www.clinicaltrials.gov/ct2/show/NCT01352858?term=tolerogenic&rank=1. 4 pages.
[No Author Listed] Innovative rheumatoid arthritis therapy receives backing from Janssen. Available at http://www.di.uq.edu.au/innovative-rheumatoid-arthritis-therapy-backed. Jan. 18, 2012. 3 pages.
[No Author Listed] New Research Shows Transplanting Stem Cells from the Brain to the Pancreas Could Cure Diabetes, as Reported by DiabeticLive.com. Oct. 18, 2011. Last accessed Jan. 5, 2012 at http://www.fiercebiotech.com/press-releases/new-research-shows-transplanting-stem-cells-brain-pancreas-could-cure-diabe. 2 pages.
[No Author Listed] Novel nanoparticle vaccine cures type 1 diabetes in mice. Apr. 8, 2010. Last accessed Dec. 6, 2011 at http://www.sciencedaily.com/releases/2010/04/100408121054.htm. 2 pages.
[No Author Listed] Scientists Use Rat's Own Stem Cells to Cure Their Diabetes. Oct. 16, 2011. Last accessed Jan. 5, 2012 at http://www.diabeteshealth.com/read/2011/10/16/7321/scientists-use-rats-own-stem-cells-to-cure-their-diabetes. 4 pages.
Ackerman et al., Cellular mechanisms governing cross-presentation of exogenous antigens. Nat Immunol. 2004;5(7):678-84.
Adorini et al., Tolerogenic dendritic cells induced by vitamin D receptor ligands enhance regulatory T cells inhibiting allograft rejection and autoimmune diseases. J Cell Biochem. Feb. 1, 2003;88(2):227-33.
Alexander et al., Universal influenza DNA vaccine encoding conserved CD4+ T cell epitopes protects against lethal viral challenge in HLA-DR transgenic mice. Vaccine. Jan. 8, 2010;28(3):664-72. Epub Nov. 4, 2009.
Anikeeva et al., Quantum dot/peptide-MHC biosensors reveal strong CD8-dependent cooperation between self and viral antigens that augment the T cell response. Proc Natl Acad Sci U S A. Nov. 7, 2006;103(45):16846-51. Epub Oct. 31, 2006.
Asano et al., Targeting activated lymphocytes with lipid microsphere containing a cytotoxic agent; efficacy of immunosuppression with a new drug delivery system. J Urology. 2001;165(5)384.
Bachem et al., Superior antigen cross-presentation and XCR1 expression define human CD11c+CD141+ cells as homologues of mouse CD8+ dendritic cells. J Exp Med. Jun. 7, 2010;207(6):1273-81. Epub May 17, 2010.
Bachmann et al., T helper cell-independent neutralizing B cell response against vesicular stomatitis virus: role of antigen patterns in B cell induction?. Eur J Immunol. 1995;25(12):3445-51.
Barchet et al., Virus-induced interferon alpha production by a dendritic cell subset in the absence of feedback signaling in vivo. J Exp Med. 2002;195(4):507-16.
Batista et al., The who, how and where of antigen presentation to B cells. Nat Rev Immunol. Jan. 2009;9(1):15-27.
Bayard et al., Hepatitis B virus (HBV)-derived DRB1*0101-restricted CD4 T-cell epitopes help in the development of HBV-specific CD8+ T cells in vivo. Vaccine. May 14, 2010;28(22):3818-26. Epub Mar. 31, 2010.
Blander, Phagocytosis and antigen presentation: a partnership initiated by Toll-like receptors. Ann Rheum Dis. Dec. 2008;67 Suppl 3:iii44-9.
Boden et al., Regulatory T cells in inflammatory bowel disease. Curr Opin Gastroenterol. Nov. 2008;24(6):733-41.
Boes et al., T-cell engagement of dendritic cells rapidly rearranges MHC class II transport. Nature. 418(6901):983-988 (2002).
Bonifaz et al., Efficient targeting of protein antigen to the dendritic cell receptor DEC-205 in the steady state leads to antigen presentation on major histocompatibility complex class I products and peripheral CD8+ T cell tolerance. J Exp Med. 2002;196(12):1627-38.
Bozzacco et al., DEC-205 receptor on dendritic cells mediates presentation of HIV gag protein to CD8+ T cells in a spectrum of human MHC I haplotypes. Proc Natl Acad Sci USA. 2007;104(4):1289-94.
Brennan et al., Invariant natural killer T cells recognize lipid self antigen induced by microbial danger signals. Nat Immunol. Oct. 30, 2011;12(12):1202-11. doi: 10.1038/ni.2143.
Busson et al., Prediction of CD4(+) T cell epitopes restricted to HLA-DP4 molecules. J Immunol Methods. Dec. 20, 2006;317(1-2):144-51. Epub Oct. 26, 2006.
Capini et al., Antigen-specific suppression of inflammatory arthritis using liposomes. J Immunol. Mar. 15, 2009;182(6):3556-65.
Carrasco et al., B cells acquire particulate antigen in a macrophage-rich area at the boundary between the follicle and the subcapsular sinus of the lymph node.Immunity. Jul. 2007;27(1):160-71. Epub Jul. 19, 2007.
Carroll, Stem cell therapy used to cure types 1&2 diabetes in rat models. Oct. 18, 2011. Last accessed Jan. 5, 2012 available at http://www.fiercebiotechresearch.com/story/stem-cell-therapy-used-cure-type-12-diabetes-rat-models/Oct. 18, 2011. 2 pages.
Casola et al., B cell receptor signal strength determines B cell fate. Nat Immunol. 2004;5(3):317-27.
Castelli et al., HLA-DP4, the most frequent HLA II molecule, defines a new supertype of peptide-binding specificity. J Immunol. Dec. 15, 2002;169(12):6928-34.
Chao et al., Induction of tolerance to human factor VIII in mice. Blood. May 15, 2001;97(10):3311-2.
Chapoval et al., HLA-DQ6 and HLA-DQ8 transgenic mice respond to ragweed allergens and recognize a distinct set of epitopes on short and giant ragweed group 5 antigens. J Immunol. Aug. 15, 1998;161(4):2032-7.
Chengalvala et al., Enhanced immunogenicity of hepatitis B surface antigen by insertion of a helper T cell epitope from tetanus toxoid. Vaccine. Mar. 5, 1999;17(9-10):1035-41.
Chinen et al., Basic and clinical immunology. J Allergy Clin Immunol. Aug. 2005;116(2):411-8.

(56) References Cited

OTHER PUBLICATIONS

Chinnery et al., The chemokine receptor CX3CR1 mediates homing of MHC class II-positive cells to the normal mouse corneal epithelium. Invest Ophthalmol Vis Sci. Apr. 2007;48(4):1568-74.

Clark, The reticulum of lymph nodes in mice studied with the electron microscope. Am J Anat. 1962;110:217-57.

Coombes et al., A functionally specialized population of mucosal CD103+ DCs induces Foxp3+ regulatory T cells via a TGF-beta and retinoic acid-dependent mechanism. J Exp Med. Aug. 6, 2007;204(8):1757-64. Epub Jul. 9, 2007.

Crozat et al. The XC chemokine receptor 1 is a conserved selective marker of mammalian cells homologous to mouse CD8alpha+ dendritic cells. J Exp Med. Jun. 7, 2010;207(6):1283-92. Epub May 17, 2010.

Cruz et al., The influence of PEG chain length and targeting moiety on antibody-mediated delivery of nanoparticle vaccines to human dendritic cells. Biomaterials. Oct. 2011;32(28):6791-803. Epub Jul. 2, 2011. E-pub version.

Cvetanovich et al., Human regulatory T cells in autoimmune diseases. Curr Opin Immunol. Dec. 2010;22(6):753-60. Epub Sep. 24, 2010.

Dane et al., Nano-sized drug-loaded micelles deliver payload to lymph node immune cells and prolong allograft survival. J Control Release. Dec. 10, 2011;156(2):154-60. Epub Aug. 12, 2011.

Dang et al., Stimulation of B lymphocytes through surface Ig receptors induces LFA-1 and ICAM-1-dependent adhesion. J Immunol. 1991;146(10):3273-9.

Del Rio et al., Development and functional specialization of CD103+ dendritic cells. Immunol Rev. Mar. 2010;234(1):268-81.

Delemarre et al., Repopulation of macrophages in popliteal lymph nodes of mice after liposome-mediated depletion. J Leukoc Biol. 1990;47(3):251-7.

Demangel et al., Single chain antibody fragments for the selective targeting of antigens to dendritic cells. Mol Immunol. May 2005;42(8):979-85. Epub Dec. 10, 2004.

Diethelm-Okita et al., Universal epitopes for human CD4+ cells on tetanus and diphtheria toxins. J Infect Dis. Mar. 2000;181(3):1001-9.

Dilillo et al., B10 cells and regulatory B cells balance immune responses during inflammation, autoimmunity, and cancer. Ann N Y Acad Sci. Jan. 2010;1183:38-57.

Dorner et al., Selective expression of the chemokine receptor XCR1 on cross-presenting dendritic cells determines cooperation with CD8+ T cells. Immunity. Nov. 20, 2009;31(5):823-33. Epub Nov. 12, 2009.

Farr et al., The structure of the sinus wall of the lymph node relative to its endocytic properties and transmural cell passage. Am J Anat. 1980;157(3):265-84.

Faunce et al., Cutting edge: in vitro-generated tolerogenic APC induce CD8+ T regulatory cells that can suppress ongoing experimental autoimmune encephalomyelitis. J Immunol. Feb. 15, 2004;172(4):1991-5.

Fischer et al., Rapamycin-conditioned, alloantigen-pulsed myeloid dendritic cells present donor MHC class I/peptide via the semi-direct pathway and inhibit survival of antigen-specific CD8(+) T cells in vitro and in vivo. Transpl Immunol. Jul. 2011;25(1):20-6. Epub May 10, 2011.

Gaitonde et al., Downregulation of CD40 signal and induction of TGF-β by phosphatidylinositol mediates reduction in immunogenicity against recombinant human Factor VIII. J Pharm Sci. Jan. 2012;101(1):48-55. doi: 10.1002/jps.22746. Epub Sep. 23, 2011.

Garcia et al., CCR9+ and CD103+ tolerogenic dendritic cell populations in food allergy patients undergoing oral immunotherapy. Clin Transl Allergy. 2011; 1(Suppl 1): O51.

Getts et al., Microparticles bearing encephalitogenic peptides induce T-cell tolerance and ameliorate experimental autoimmune encephalomyelitis. Nat Biotechnol. Nov. 18, 2012. doi: 10.1038/nbt.2434. [Epub ahead of print].

Giannoukakis et al., Phase I (safety) study of autologous tolerogenic dendritic cells in type 1 diabetic patients. Diabetes Care. Sep. 2011;34(9):2026-32. Epub Jun. 16, 2011.

Gray et al., Apoptotic cells protect mice from autoimmune inflammation by the induction of regulatory B cells. Proc Natl Acad Sci U S A. Aug. 28, 2007;104(35):14080-5. Epub Aug. 21, 2007.

Gray et al., What are regulatory B cells? Eur J Immunol. Oct. 2010;40(10):2677-9.

Gross et al., Fulfilling the dream: tolerogenic dendritic cells to treat multiple sclerosis. Eur J Immunol. Mar. 2012;42(3):569-72. doi: 10.1002/eji.201242402.

Hamdy et al., Co-delivery of cancer-associated antigen and Toll-like receptor 4 ligand in PLGA nanoparticles induces potent CD8+ T cell-mediated anti-tumor immunity. Vaccine. Sep. 15, 2008;26(39):5046-57. Epub Aug. 3, 2008.

Hangartner et al., Antiviral immune responses in gene-targeted mice expressing the immunoglobulin heavy chain of virus-neutralizing antibodies. Proc Natl Acad Sci USA. 2003;100:12883-88.

Harry et al., Generation and characterisation of therapeutic tolerogenic dendritic cells for rheumatoid arthritis. Ann Rheum Dis. Nov. 2010;69(11):2042-50. Epub Jun. 15, 2010.

Hawiger et al., Dendritic cells induce peripheral T cell unresponsiveness under steady state conditions in vivo. J Exp Med. 2001;194(6):769-79.

Jordan et al., Promotion of B cell immune responses via an alum-induced myeloid cell population. Science. Jun. 18, 2004;304(5678):1808-10.

Junt et al., Subcapsular sinus macrophages in lymph nodes clear lymph-borne viruses and present them to antiviral B cells. Nature. 2007;450:110-4. Supplemental material.

Kang et al., Cutting edge: Immunosuppressant as adjuvant for tolerogenic immunization. J Immunol. Apr. 15, 2008;180(8):5172-6.

Karrer et al., On the key role of secondary lymphoid organs in antiviral immune responses studied in alymphoplastic (aly/aly) and spleenless (Hox11(−)/−) mutant mice. J Exp Med. 1997;185(12):2157-70.

Kim et al., Inhibition of follicular T-helper cells by CD8(+) regulatory T cells is essential for self tolerance. Nature. Sep. 16, 2010;467(7313):328-32.

Krieg et al., CpG motifs in bacterial DNA trigger direct B-cell activation. Nature. 1995;374(6522):546-9.

Kuwabara et al., Insulin biosynthesis in neuronal progenitors derived from adult hippocampus and the olfactory bulb. EMBO Mol Med. Dec. 2011;3(12):742-54. doi: 10.1002/emmm.201100177. Epub Oct. 10, 2011. E-pub verion.

Lanza et al., Transplantation of encapsulated cells and tissues. Surgery. Jan. 1997;121(1):1-9.

Liu et al., Origin and development of dendritic cells. Immunol Rev. Mar. 2010;234(1):45-54.

Livingston et al., A rational strategy to design multiepitope immunogens based on multiple Thlymphocyte epitopes. J Immunol. Jun. 1, 2002;168(11):5499-506.

Lloyd, Disulphide reduction in lysosomes. The role of cysteine. Biochem J. Jul. 1, 1986;237(1):271-2.

Ludewig et al., Induction of optimal anti-viral neutralizing B cell responses by dendritic cells requires transport and release of virus particles in secondary lymphoid organs. Eur J Immunol. 2000;30(1):185-96.

Lund et al., Effector and regulatory B cells: modulators of CD4(+) T cell immunity. Nat Rev Immunol. Apr. 2010;10(4):236-47. Epub Mar. 12, 2010.

Martin et al., A vector-based minigene vaccine approach results in strong induction of T-cell responses specific of hepatitis C virus. Vaccine. May 12, 2008;26(20):2471-81. Epub Apr. 1, 2008.

Martinez-Pomares et al., Antigen presentation the macrophage way. Cell. Nov. 16, 2007;131(4):641-3.

Martín-Gayo et al., Plasmacytoid dendritic cells resident in human thymus drive natural Treg cell development. Blood. Jul. 1, 2010;115(26):5366-75. Epub Mar. 31, 2010.

Matta et al., Tolerogenic plasmacytoid DC. Eur J Immunol. Oct. 2010;40(10):2667-76.

Matteoli et al., Gut CD103+ dendritic cells express indoleamine 2,3-dioxygenase which influences T regulatory/T effector cell balance and oral tolerance induction. Gut. May 2010;59(5):595-604.

(56) References Cited

OTHER PUBLICATIONS

Maye et al., Comparison of the phagocytosis of two types of cyclosporin (SDZ OXL 400 and SDZ IMM 125) by alveolar macrophages from hamsters. Cell Biol Toxicol. Dec. 1998;14(6):411-8.

Mempel et al., T-cell priming by dendritic cells in lymph nodes occurs in three distinct phases. Nature. 2004;427(6970):154-9.

Metelitsa et al., Antidisialoganglioside/granulocyte macrophage-colonystimulating factor fusion protein facilitates neutrophil antibody-dependent cellular cytotoxicity and depends on FcγRII (CD32) and Mac-1 (CD11b/CD18) for enhanced effector cell adhesion and azurophil granule exocytosis. Blood. 2002;99(11):4166-73.

Miyara et al., Therapeutic approaches to allergy and autoimmunity based on FoxP3+ regulatory T-cell activation and expansion. J Allergy Clin Immunol. Apr. 2009;123(4):749-55.

Moghimi et al., Induction of tolerance to factor VIII by transient co-administration with rapamycin. J Thromb Haemost. Aug. 2011;9(8):1524-33. doi: 10.1111/j.1538-7836.2011.04351.x.

Nepom et al., Challenges in the pursuit of immune tolerance. Challenges in the pursuit of immune tolerance. Immunol Rev. May 2011;241(1):49-62. doi: 10.1111/j.1600-065X.2011.01003.x.

Nikolic et al., Plasmacytoid dendritic cells in autoimmune diabetes—potential tools for immunotherapy. Immunobiology. 2009;214(9-10):791-9. Epub Jul. 22, 2009.

Notter et al., Targeting of a B7-1 (CD80) immunoglobulin G fusion protein to acute myeloid leukemia blasts increases their costimulatory activity for autologous remission T cells. Blood. 2001;97(10):3138-45.

Ochsenbein et al., Control of early viral and bacterial distribution and disease by natural antibodies. Science. 1999;286(5447):2156-9.

Ochsenbein et al., Protective T cell-independent antiviral antibody responses are dependent on complement. J Exp Med. 1999;190(8):1165-74.

Oh et al., CD4+CD25+ regulatory T cells in autoimmune arthritis. Immunol Rev. Jan. 2010;233(1):97-111.

Okada et al., Antigen-engaged B cells undergo chemotaxis toward the T zone and form motile conjugates with helper T cells. PLoS Biol. 2005;3(6):e150. 1047-61.

O'Neil et al., Extracellular matrix binding mixed micelles for drug delivery applications. J Control Release. Jul. 20, 2009;137(2):146-51. Epub Mar. 27, 2009.

O'Sullivan et al., Truncation analysis of several DR binding epitopes. J Immunol. Feb. 15, 1991;146(4):1240-6.

Paolicelli et al., Surface-modified PLGA-based nanoparticles that can efficiently associate and deliver virus-like particles. Nanomedicine (Lond). Aug. 2010;5(6):843-53. doi: 10.2217/nnm.10.69.

Pape et al., The humoral immune response is initiated in lymph nodes by B cells that acquire soluble antigen directly in the follicles. Immunity. 2007;26(4):491-502.

Phillips et al., Enhanced antibody response to liposome-associated protein antigens: preferential stimulation of IgG2a/b production. Vaccine. 1992;10(3):151-8.

Qadura et al., Reduction of the immune response to factor VIII mediated through tolerogenic factor VIII presentation by immature dendritic cells. J Thromb Haemost. Dec. 2008;6(12):2095-104. Epub Sep. 27, 2008.

Qi et al., Extrafollicular activation of lymph node B cells by antigen-bearing dendritic cells. Science. 2006;312(5780):1672-6.

Ragni et al., Factor VIII-pulsed dendritic cells reduce anti-factor VIII antibody formation in the hemophilia A mouse model. Exp Hematol. Jun. 2009;37(6):744-54.

Reddy et al., Exploiting lymphatic transport and complement activation in nanoparticle vaccines. Nat Biotech. 2007;25(10):1159-64.

Reif et al., Balanced responsiveness to chemoattractants from adjacent zones determines B-cell position. Nature. 2002;416(6876):94-9.

Robbins et al., Stable expression of shRNAs in human CD34+ progenitor cells can avoid induction of interferon responses to siRNAs in vitro. Nature Biotechnology. 2006;24(5):566-71.

Rossbacher et al, The B cell receptor itself can activate complement to provide the complement receptor 1/2 ligand required to enhance B cell immune responses in vivo. J Exp Med. 2003;198(4):591-602.

Scardino et al., A polyepitope DNA vaccine targeted to Her-2/ErbB-2 elicits a broad range of human and murine CTL effectors to protect against tumor challenge. Cancer Res. Jul. 15, 2007;67(14):7028-36.

Shen et al., Enhanced and prolonged cross-presentation following endosomal escape of exogenous antigens encapsulated in biodegradable nanoparticles. Immunol. 2006;117:78-88.

Shiow et al., CD69 acts downstream of interferon-alpha/beta to inhibit S1P1 and lymphocyte egress from lymphoid organs. Nature. Mar. 23, 2006;440(7083):540-4. Epub Mar. 8, 2006.

Shortman et al., Steady-state and inflammatory dendritic-cell development. Nat Rev Immunol. Jan. 2007;7(1):19-30. Epub Dec. 15, 2006.

Sondel et al., Preclinical and clinical development of immunocytokines. Curr Opin Investig Drugs. 2003;4(6):696-700.

Srinivasan et al., Prediction of class I T-cell epitopes: evidence of presence of immunological hot spots inside antigens. Bioinformatics. Aug. 4, 2004;20 Suppl 1:i297-302.

Storm et al., Surface Modification of Nanoparticles to Oppose Uptake by the Mononuclear Phagocyte System. Adv Drug Deliv Rev. 1995;17:31-48.

Tang et al., Adenovirus hexon T-cell epitope is recognized by most adults and is restricted by HLA DP4, the most common class II allele. Gene Ther. Sep. 2004;11(18):1408-15.

Tarlinton et al., Antigen to the node: B cells go native. Immunity. Apr. 2007;26(4):388-90.

Taylor et al., Macrophage receptors and immune recognition. Annu Rev Immunol. 2005;23:901-44.

Turnquist et al., Rapamycin-conditioned dendritic cells are poor stimulators of allogeneic CD4+ T cells, but enrich for antigen-specific Foxp3+ T regulatory cells and promote organ transplant tolerance. J Immunol. Jun. 1, 2007;178(11):7018-31.

Unkeless et al., Structure and function of human and murine receptors for IgG. Annu Rev Immunol. 1998;6:251-81.

Vascotto et al., Antigen presentation by B lymphocytes: how receptor signaling directs membrane trafficking. Curr Opin Immunol. 2007;19(1):93-8.

Velluto et al., PEG-b-PPS diblock copolymer aggregates for hydrophobic drug solubilization and release: cyclosporin A as an example. Mol Pharm. Jul.-Aug. 2008;5(4):632-42. Epub Jun. 12, 2008.

Vila et al., Regulatory T cells and autoimmunity. Curr Opin Hematol. Jul. 2009;16(4):274-9.

Villadangos et al., Found in translation: the human equivalent of mouse CD8+ dendritic cells. J Exp Med. Jun. 7, 2010;207(6):1131-4. Epub May 31, 2010.

Von Andrian et al., Homing and cellular traffic in lymph nodes. Nat Rev Immunol. 2003;3(11):867-78.

Wang et al., Blood mononuclear cells induce regulatory NK T thymocytes in anterior chamber-associated immune deviation. J Leukoc Biol. May 2001;69(5):741-6.

Weber et al., T cell epitope: friend or foe? Immunogenicity of biologics in context. Adv Drug Deliv Rev. Sep. 30, 2009;61(11):965-76. Epub Jul. 18, 2009.

Wessels et al., Studies of group B streptococcal infection in mice deficient in complement component C3 or C4 demonstrate an essential role for complement in both innate and acquired immunity. Proc Natl Acad Sci USA. 1995;92(25):11490-4.

Yeste et al., Nanoparticle-mediated codelivery of myelin antigen and a tolerogenic small molecule suppresses experimental autoimmune encephalomyelitis. Proc Natl Acad Sci U S A. Jul. 10, 2012;109(28):11270-5. Epub Jun. 27, 2012.

Zhang-Hoover et al., Tolerogenic APC generate CD8+ T regulatory cells that modulate pulmonary interstitial fibrosis. J Immunol. Jan. 1, 2004;172(1):178-85.

Zheng et al., How antigen quantity and quality determine T-cell decisions in lymphoid tissue. Mol Cell Biol. Jun. 2008;28(12):4040-51. Epub Apr. 21, 2008.

Zhu et al., T cell epitope mapping of ragweed pollen allergen Ambrosia artemisiifolia (Amb a 5) and Ambrosia trifida (Amb t 5) and the role of free sulfhydryl groups in T cell recognition. J Immunol. Nov. 15, 1995;155(10):5064-73.

(56) References Cited

OTHER PUBLICATIONS

Fasier et al., Antagonistic peptides specifically inhibit proliferation, cytokine production, CD40L expression, and help for IgE synthesis by Der p 1-specific human T-cell clones. J Allergy Clin Immunol. Apr. 1998;101(4 Pt 1):521-30.

Kingsley et al., Transplantation tolerance: lessons from experimental rodent models. Transpl Int. Oct. 2007;20(10):828-41. Epub Aug. 17, 2007.

Sharabi et al., The suppression of murine lupus by a tolerogenic peptide involves foxp3-expressing CD8 cells that are required for the optimal induction and function of foxp3-expressing CD4 cells. J Immunol. Sep. 1, 2008;181(5):3243-51.

Soroosh et al., Th9 and allergic disease. Immunology. Aug. 2009;127(4):450-8. doi: 10.1111/j.1365-2567.2009.03114.x.

International Preliminary Report on Patentability for PCT/US2012/035366 mailed Oct. 29, 2013.

Fifis et al., Size-dependent immunogenicity: therapeutic and protective properties of nano-vaccines against tumors. J Immunol. Sep. 1, 2004;173(5):3148-54.

Jones, Critically assessing the state-of-the-art in protein structure prediction. Pharmacogenomics J. 2001;1(2):126-34. Review.

Mottram et al., Type 1 and 2 immunity following vaccination is influenced by nanoparticle size: formulation of a model vaccine for respiratory syncytial virus. Mol Pharm. Jan.-Feb. 2007;4(1):73-84.

Reichardt et al., Impact of Mammalian Target of Rapamycin Inhibition on Lymphoid Homing and Tolerogenic Function of Nanoparticle-Labeled Dendritic Cells following Allogeneic Hematopoietic Cell Transplantation. J Immunol. 2008;181:4770-9.

Skolnick et al., From genes to protein structure and function: novel applications of computational approaches in the genomic era. Trends Biotechnol. Jan. 2000;18(1):34-9. Review.

Tosatto et al., Large-scale prediction of protein structure and function from sequence. Curr Pharm Des. 2006;12(17):2067-86. Review.

Wang et al., A systematic assessment of MHC class II peptide binding predictions and evaluation of a consensus approach. PLoS Comput Biol. Apr. 4, 2008;4(4):e1000048. doi: 10.1371/journal.pcbi.1000048.

Zhang et al., The mechanism of B lymphocytes in inducing immune tolerance. Immunol J. Jul. 2010;26(7):643-6.

Extended European Search Report for Application No. EP 127760635 mailed Jan. 9, 2015.

Bouaziz et al., Regulatory B cells as inhibitors of immune responses and inflammation. Immunol Rev. Aug. 2008;224:201-14. doi: 10.1111/j.1600-065X.2008.00661.x. Review.

Bryant et al., Nanoparticle delivery of donor antigens for transplant tolerance in allogeneic islet transplantation. Biomaterials. Oct. 2014;35(31):8887-94. doi: 10.1016/j.biomaterials.2014.06.044.

Cappellano et al., Subcutaneous inverse vaccination with PLGA particles loaded with a MOG peptide and IL-10 decreases the severity of experimental autoimmune encephalomyelitis. Vaccine. Aug. 20, 2014. pii: 50264-410X(14)01129-3. doi: 10.1016/j.vaccine.2014.08.016. 9 pages.

Davila et al., Cell-based immunotherapy with suppressor CD8+ T cells in rheumatoid arthritis. J Immunol. Jun. 1, 2005;174(11):7292-301.

Dinesh et al., CD8+ Tregs in lupus, autoimmunity, and beyond. Autoimmun Rev. Jun. 2010;9(8):560-8. doi: 10.1016/j.autrev.2010.03.006. Epub Jun. 1, 2011. 21 pages.

Düchs, Dissertation entitled: Effects of Toll-like receptor agonists on the pathogenesis of atopic asthma in mice, University of Würzburg, Sep. 2011. 147 pages.

Eghtesad et al., Effect of rapamycin on immunity induced by vector-mediated dystrophin expression in mdx skeletal muscle. Sci Rep. 2012;2:399. doi: 10.1038/srep00399. Epub May 8, 2012. 6 pages.

Endharti et al., Cutting edge: CD8+CD122+ regulatory T cells produce IL-10 to suppress IFN-gamma production and proliferation of CD8+ T cells. J Immunol. Dec. 1, 2005;175(11):7093-7.

Haddadi, Delivery of rapamycin by PLGA nanoparticles enhances its suppressive activity on dendritic cells. J Biomed Mat Res A. 2007;84A(4):885-98.

Hahn et al., Cellular and molecular mechanisms of regulation of autoantibody production in lupus. Ann N Y Acad Sci. Jun. 2005;1051:433-41. Review. Epub Apr. 10, 2008. 9 pages.

Hahn et al., Tolerogenic treatment of lupus mice with consensus peptide induces Foxp3-expressing, apoptosis-resistant, TGFbeta-secreting CD8+ T cell suppressors. J Immunol. Dec. 1, 2005;175(11):7728-37.

Hamdy et al., Targeting dendritic cells with nano-particulate PLGA cancer vaccine formulations. Adv Drug Deliv Rev. Sep. 10, 2011;63(10-11):943-55. doi: 10.1016/j.addr.2011.05.021. Epub Jun. 6, 2011. Review.

Imamura et al., Pravastatin attenuates allergic airway inflammation by suppressing antigen sensitisation, interleukin 17 production and antigen presentation in the lung. Thorax. Jan. 2009;64(1):44-9. doi: 10.1136/thx.2007.094540. Epub Oct. 3, 2008.

Kang et al., Very low-dose tolerance with nucleosomal peptides controls lupus and induces potent regulatory T cell subsets. J Immunol. Mar. 15, 2005;174(6):3247-55.

Karamloo et al., Prevention of allergy by a recombinant multi-allergen vaccine with reduced IgE binding and preserved T cell epitopes. Eur J Immunol. Nov. 2005;35(11):3268-76.

Keselowsky et al., Multifunctional dendritic cell-targeting polymeric microparticles: engineering new vaccines for type 1 diabetes. Hum Vaccin. Jan. 1, 2011;7(1):37-44. Epub Jan. 1, 2011. Review.

Kim et al., Simvastatin induces Foxp3+ T regulatory cells by modulation of transforming growth factor-beta signal transduction. Immunology. Aug. 2010;130(4):484-93. doi: 10.1111/j.1365-2567.2010.03269.x. Epub Apr. 12, 2010.

Konya et al., Treating autoimmune disease by targeting CD8(+) T suppressor cells. Expert Opin Biol Ther. Aug. 2009;9(8):951-65. doi: 10.1517/14712590903020759. Review. Epub Aug. 1, 2010. 22 pages.

Menzies et al., Simvastatin does not exhibit therapeutic anti-inflammatory effects in asthma. J Allergy Clin Immunol. Feb. 2007;119(2):328-35. Epub Dec. 4, 2006.

Nixon et al., Synthetic peptides entrapped in microparticles can elicit cytotoxic T cell activity. Vaccine. Nov. 1996;14(16):1523-30.

Shimizu et al., Direct anti-inflammatory mechanisms contribute to attenuation of experimental allograft arteriosclerosis by statins. Circulation. Oct. 28, 2003;108(17):2113-20. Epub Sep. 29, 2003.

Tai et al., A novel rapamycin-polymer conjugate based on a new poly(ethylene glycol) multiblock copolymer. Pharm Res. Mar. 2014;31(3):706-19. doi: 10.1007/s11095-013-1192-3. Epub Sep. 26, 2013.

Tarzi et al., Peptide immunotherapy for allergic disease. Expert Opin Biol Ther. Jul. 2003;3(4):617-26. Review.

\* cited by examiner

In vivo effects of t2SVP after a single injection

TOLEROGENIC SYNTHETIC NANOCARRIERS TO REDUCE IMMUNE RESPONSES TO THERAPEUTIC PROTEINS

RELATED APPLICATIONS

This application claims the benefit under 35 U.S.C. §119 of U.S. provisional application 61/480,946, filed Apr. 29, 2011, 61/513,514, filed Jul. 29, 2011, 61/531,147, filed Sep. 6, 2011, 61/531,153, filed Sep. 6, 2011, 61/531,164, filed Sep. 6, 2011, 61/531,168, filed Sep. 6, 2011, 61/531,175, filed Sep. 6, 2011, 61/531,180, filed Sep. 6, 2011, 61/531,194, filed Sep. 6, 2011, 61/531,204, filed Sep. 6, 2011, 61/531,209, filed Sep. 6, 2011, 61/531,215, filed Sep. 6, 2011, the entire contents of each of which are incorporated herein by reference.

FIELD OF THE INVENTION

This invention relates to synthetic nanocarrier compositions with therapeutic protein antigen-presenting cell (APC) presentable antigens and immunosuppressants, and related methods. The compositions and methods allow for efficient uptake by APCs to shift the immune response in favor of tolerogenic immune response development specific to therapeutic proteins. The compositions and methods provided can, therefore, be used to generate a tolerogenic immune response in a subject in which the administration of a therapeutic protein is or is expected to result in undesired immune responses.

BACKGROUND OF THE INVENTION

Therapeutic treatments, such as protein or enzyme replacement therapies, often result in undesired immune responses to the particular therapeutic. In such cases, cells of the immune system recognize the therapeutic as foreign and attempt to destroy it, just as they attempt to destroy infecting organisms such as bacteria and viruses. Such undesired immune responses may be reduced through the use of immunosuppressant drugs. Conventional immunosuppressant drugs, however, are broad-acting. Additionally, in order to maintain immunosuppression, immunosuppressant drug therapy is generally a life-long proposition. Unfortunately, the use of broad-acting immunosuppressants are associated with a risk of severe side effects, such as tumors, infections, nephrotoxicity and metabolic disorders. Accordingly, new immunosuppressant therapies would be beneficial.

SUMMARY OF THE INVENTION

In one aspect, a composition comprising (i) a first population of synthetic nanocarriers that are coupled to immunosuppressants, and (ii) a second population of synthetic nanocarriers that are coupled to therapeutic protein APC presentable antigens is provided. In one embodiment, the first population and second population are the same population. In another embodiment. The first population and second population are different populations.

In yet another embodiment, the immunosuppressants comprise a statin, an mTOR inhibitor, a TGF-β signaling agent, a corticosteroid, an inhibitor of mitochondrial function, a P38 inhibitor, an NF-κβ inhibitor, an adenosine receptor agonist, a prostaglandin E2 agonist, a phosphodiesterasse 4 inhibitor, an HDAC inhibitor or a proteasome inhibitor. In still another embodiment, the mTOR inhibitor is rapamycin or a rapamycin analog.

In some embodiments, the therapeutic protein APC presentable antigens are provided by coupling the therapeutic protein to the synthetic nanocarriers. In other embodiments, the therapeutic protein APC presentable antigens are provided by coupling a polypeptide or peptide obtained or derived from the therapeutic protein. In a further embodiment, the therapeutic protein APC presentable antigens comprise MHC Class I-restricted and/or MHC Class II-restricted epitopes and/or B cell epitopes of a therapeutic protein. In another embodiment, the therapeutic protein APC presentable antigens comprise MHC Class II-restricted epitopes of a therapeutic protein. In another embodiment, the therapeutic protein APC presentable antigens comprise substantially no B cell epitopes of a therapeutic protein. In another embodiment, the therapeutic protein APC presentable antigens comprise MHC Class II-restricted epitopes and substantially no B cell epitopes of a therapeutic protein.

In one embodiment, the therapeutic protein APC presentable antigens comprise a therapeutic protein for protein replacement or protein supplementation therapy, or a fragment or derivative thereof. In another embodiment, the therapeutic protein APC presentable antigens comprise a/an infusible or injectable therapeutic protein, enzyme, enzyme cofactor, hormone, blood or blood coagulation factor, cytokine, interferon, growth factor, monoclonal antibody, polyclonal antibody or protein associated with Pompe's disease, or a fragment or derivative of any of the foregoing. In another embodiment, the infusible or injectable therapeutic protein comprises Tocilizumab, alpha-1 antitrypsin, Hematide, albinterferon alfa-2b, Rhucin, tesamorelin, ocrelizumab, belimumab, pegloticase, taliglucerase alfa, agalsidase alfa or velaglucerase alfa. In another embodiment, the enzyme comprises an oxidoreductase, transferase, hydrolase, lyase, isomerase or ligase. In another embodiment, the enzyme comprises an enzyme for enzyme replacement therapy for a lysosomal storage disorder. In another embodiment, the enzyme for enzyme replacement therapy for a lysosomal storage disorder comprises imiglucerase, a-galactosidase A (a-gal A), agalsidase beta, acid a-glucosidase (GAA), alglucosidase alfa, LUMIZYME, MYOZYME, arylsulfatase B, laronidase, ALDURAZYME, idursulfase, ELAPRASE, arylsulfatase B or NAGLAZYME. In another embodiment, the cytokine comprises a lymphokine, interleukin, chemokine, type 1 cytokine or a type 2 cytokine. In another embodiment, the blood and blood coagulation factor comprises Factor I, Factor II, tissue factor, Factor V, Factor VII, Factor VIII, Factor IX, Factor X, Factor Xa, Factor XII, Factor XIII, von Willebrand factor, prekallikrein, high-molecular weight kininogen, fibronectin, antithrombin III, heparin cofactor II, protein C, protein S, protein Z, protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant or epoetin alfa. In still another embodiment, the therapeutic protein is expressed in, by or on cells of a cell-based therapy.

In one embodiment, the composition is in an amount effective to generate a tolerogenic immune response to the therapeutic protein APC presentable antigen or therapeutic protein from which the antigens are obtained or derived. In another embodiment, the composition is in an amount effective to reduce the generation of therapeutic protein-specific antibodies when administered to a subject.

In another embodiment, the load of the immunosuppressants and/or antigens on average across the first and/or second population of synthetic nanocarriers is between 0.0001% and 50%. In still another embodiment, the load of the immunosuppressants and/or antigens on average across the first and/or second population of synthetic nanocarriers is between 0.1% and 10%.

In one embodiment, the synthetic nanocarriers of the first population and/or second population comprise lipid nanoparticles, polymeric nanoparticles, metallic nanoparticles, surfactant-based emulsions, dendrimers, buckyballs, nanowires, virus-like particles or peptide or protein particles. In another embodiment, the synthetic nanocarriers of the first and/or second populations comprise lipid nanoparticles. In yet another embodiment, the synthetic nanocarriers of the first and/or second populations comprise liposomes. In still another embodiment, the synthetic nanocarriers of the first and/or second populations comprise metallic nanoparticles. In a further embodiment, the metallic nanoparticles comprise gold nanoparticles. In yet a further embodiment, the synthetic nanocarriers of the first and/or second populations comprise polymeric nanoparticles. In another embodiment, the polymeric nanoparticles comprise polymers that are non-methoxy-terminated, pluronic polymers. In still a further embodiment, the polymeric nanoparticles comprise a polyester, a polyester coupled to a polyether, polyamino acid, polycarbonate, polyacetal, polyketal, polysaccharide, polyethyloxazoline or polyethyleneimine. In another embodiment, the polyester comprises a poly(lactic acid), poly(glycolic acid), poly(lactic-co-glycolic acid) or polycaprolactone. In yet another embodiment, the polymeric nanoparticles comprise a polyester and a polyester coupled to a polyether. In another embodiment, the polyether comprises polyethylene glycol or polypropylene glycol.

In another embodiment, the mean of a particle size distribution obtained using dynamic light scattering of the synthetic nanocarriers of the first and/or second population is a diameter greater than 100 nm. In another embodiment, the diameter is greater than 150 nm. In another embodiment, the diameter is greater than 200 nm. In another embodiment, the diameter is greater than 250 nm. In another embodiment, the diameter is greater than 300 nm.

In a further embodiment, the aspect ratio of the synthetic nanocarriers of the first population and/or second population is greater than 1:1, 1:1.2, 1:1.5, 1:2, 1:3, 1:5, 1:7 or 1:10.

In yet another embodiment, the composition further comprises a pharmaceutically acceptable excipient.

In another aspect, a dosage form comprising any of the compositions provided herein is provided.

In another aspect, a method comprising administering any of the compositions or dosage forms provided herein to a subject that is being administered or will be administered a therapeutic protein is provided. In one embodiment, the method further comprises administering the therapeutic protein to the subject. In another embodiment, the therapeutic protein is administered prior to, concomitantly with or after the administration of the composition or dosage form. In yet another embodiment, one or more maintenance doses of the composition or dosage form is administered to the subject.

In yet another embodiment, the method further comprises assessing the generation of an undesired immune response in the subject prior to and/or after the administration of the composition or dosage form and/or the therapeutic protein. In one embodiment, the undesired immune response is the generation of therapeutic protein-specific antibodies. In another embodiment, the undesired immune response is CD4+ T cell proliferation and/or activity specific to the therapeutic protein. In yet another embodiment, the undesired immune response is B cell proliferation and/or activity specific to the therapeutic protein.

In one embodiment, the therapeutic protein comprises a therapeutic protein for protein replacement or protein supplementation therapy. In another embodiment, the therapeutic protein comprises a/an infusible or injectable therapeutic protein, enzyme, enzyme cofactor, hormone, blood or blood coagulation factor, cytokine, interferon, growth factor, monoclonal antibody, polyclonal antibody or protein associated with Pompe's disease. In another embodiment, the infusible or injectable therapeutic protein comprises Tocilizumab, alpha-1 antitrypsin, Hematide, albinterferon alfa-2b, Rhucin, tesamorelin, ocrelizumab, belimumab, pegloticase, taliglucerase alfa, agalsidase alfa or velaglucerase alfa. In another embodiment, the enzyme comprises an oxidoreductase, transferase, hydrolase, lyase, isomerase or ligase. In another embodiment, the enzyme comprises an enzyme for enzyme replacement therapy for a lysosomal storage disorder. In another embodiment, the enzyme for enzyme replacement therapy for a lysosomal storage disorder comprises imiglucerase, a-galactosidase A (a-gal A), agalsidase beta, acid a-glucosidase (GAA), alglucosidase alfa, LUMIZYME, MYOZYME, arylsulfatase B, laronidase, ALDURAZYME, idursulfase, ELAPRASE, arylsulfatase B or NAGLAZYME. In another embodiment, the cytokine comprises a lymphokine, interleukin, chemokine, type 1 cytokine or a type 2 cytokine. In another embodiment, the blood and blood coagulation factor comprises Factor I, Factor II, tissue factor, Factor V, Factor VII, Factor VIII, Factor IX, Factor X, Factor Xa, Factor XII, Factor XIII, von Willebrand factor, prekallikrein, high-molecular weight kininogen, fibronectin, antithrombin III, heparin cofactor II, protein C, protein S, protein Z, protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant or epoetin alfa. In still another embodiment, the therapeutic protein is expressed in, by or on cells of a cell-based therapy.

In one embodiment, the administering of the first and/or second population of synthetic nanocarriers and/or therapeutic protein is by intravenous, intraperitoneal, transmucosal, oral, subcutaneous, pulmonary, intranasal, intradermal or intramuscular administration. In another embodiment, the administering of the first and/or second population of synthetic nanocarriers and/or therapeutic protein is by inhalation or intravenous, subcutaneous or transmucosal administration.

In still another aspect, a method comprising administering to a subject a composition comprising (i) a first population of synthetic nanocarriers that are coupled to immunosuppressants, and (ii) a second population of synthetic nanocarriers that are coupled to therapeutic protein APC presentable antigens, wherein the composition is in an amount effective to reduce the generation of an undesired immune response against the therapeutic protein APC presentable antigens is provided. In yet another aspect, a method comprising reducing the generation of an undesired immune response in a subject by administering a composition comprising (i) a first population of synthetic nanocarriers that are coupled to immunosuppressants, and (ii) a second population of synthetic nanocarriers that are coupled to therapeutic protein APC presentable antigens is provided. In a further aspect, a method comprising administering a composition to a subject according to a protocol that was previously shown to reduce the generation of an undesired immune response to therapeutic protein APC presentable antigens in one or more test subjects; wherein the composition comprises (i) a first population of synthetic nanocarriers that are coupled to immunosuppressants, and (ii) a second population of synthetic nanocarriers that are coupled to the therapeutic protein APC presentable antigens is provided. In one embodiment, the first population and second population are the same population. In another embodiment, the first population and second population are different populations.

In yet another embodiment, the method further comprises providing or identifying the subject. In still another embodiment, the method further comprises assessing the generation of the undesired immune response in the subject prior to and/or after the administration of the composition. In one embodiment, the undesired immune response is the generation of therapeutic protein-specific antibodies and/or CD4+ T cell proliferation and/or activity specific to the therapeutic protein and/or B cell proliferation and/or activity specific to the therapeutic protein.

In another embodiment, the immunosuppressants comprise a statin, an mTOR inhibitor, a TGF-β signaling agent, a corticosteroid, an inhibitor of mitochondrial function, a P38 inhibitor, an NF-κβ inhibitor, an adenosine receptor agonist, a prostaglandin E2 agonist, a phosphodiesterasse 4 inhibitor, an HDAC inhibitor or a proteasome inhibitor. In yet another embodiment, the mTOR inhibitor is rapamycin or a rapamycin analog.

In some embodiments, the therapeutic protein APC presentable antigens are provided by coupling the therapeutic protein to the synthetic nanocarriers. In other embodiments, the therapeutic protein APC presentable antigens are provided by coupling a polypeptide or peptide obtained or derived from the therapeutic protein. In a further embodiment, the therapeutic protein APC presentable antigens comprise MHC Class I-restricted and/or MHC Class II-restricted epitopes and/or B cell epitopes of a therapeutic protein. In another embodiment, the therapeutic protein APC presentable antigens comprise MHC Class II-restricted epitopes of a therapeutic protein. In another embodiment, the therapeutic protein APC presentable antigens comprise substantially no B cell epitopes of a therapeutic protein. In another embodiment, the therapeutic protein APC presentable antigens comprise MHC Class II-restricted epitopes and substantially no B cell epitopes of a therapeutic protein.

In one embodiment, the therapeutic protein comprises a therapeutic protein for protein replacement or protein supplementation therapy. In another embodiment, the therapeutic protein comprises a/an infusible or injectable therapeutic protein, enzyme, enzyme cofactor, hormone, blood or blood coagulation factor, cytokine, interferon, growth factor, monoclonal antibody, polyclonal antibody or protein associated with Pompe's disease. In another embodiment, the infusible or injectable therapeutic protein comprises Tocilizumab, alpha-1 antitrypsin, Hematide, albinterferon alfa-2b, Rhucin, tesamorelin, ocrelizumab, belimumab, pegloticase, taliglucerase alfa, agalsidase alfa or velaglucerase alfa. In another embodiment, the enzyme comprises an oxidoreductase, transferase, hydrolase, lyase, isomerase or ligase. In another embodiment, the enzyme comprises an enzyme for enzyme replacement therapy for a lysosomal storage disorder. In another embodiment, the enzyme for enzyme replacement therapy for a lysosomal storage disorder comprises imiglucerase, a-galactosidase A (a-gal A), agalsidase beta, acid a-glucosidase (GAA), alglucosidase alfa, LUMIZYME, MYOZYME, arylsulfatase B, laronidase, ALDURAZYME, idursulfase, ELAPRASE, arylsulfatase B or NAGLAZYME. In another embodiment, the cytokine comprises a lymphokine, interleukin, chemokine, type 1 cytokine or a type 2 cytokine. In another embodiment, the blood and blood coagulation factor comprises Factor I, Factor II, tissue factor, Factor V, Factor VII, Factor VIII, Factor IX, Factor X, Factor Xa, Factor XII, Factor XIII, von Willebrand factor, prekallikrein, high-molecular weight kininogen, fibronectin, antithrombin III, heparin cofactor II, protein C, protein S, protein Z, protein Z-related protease inhibitor (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant or epoetin alfa. In still another embodiment, the therapeutic protein is expressed in, by or on cells of a cell-based therapy.

In one embodiment, the composition reduces is in an amount effective to reduce the generation of therapeutic protein-specific antibodies and/or CD4+ T cell proliferation and/ or activity specific to the therapeutic protein and/or B cell proliferation and/or activity specific to the therapeutic protein.

In another embodiment, the load of the immunosuppressants and/or antigens on average across the first and/or second population of synthetic nanocarriers is between 0.0001% and 50%. In still another embodiment, the load of the immunosuppressants and/or antigens on average across the first and/ or second population of synthetic nanocarriers is between 0.1% and 10%.

In one embodiment, the synthetic nanocarriers of the first population and/or second population comprise lipid nanoparticles, polymeric nanoparticles, metallic nanoparticles, surfactant-based emulsions, dendrimers, buckyballs, nanowires, virus-like particles or peptide or protein particles. In another embodiment, the synthetic nanocarriers of the first and/or second populations comprise lipid nanoparticles. In yet another embodiment, the synthetic nanocarriers of the first and/or second populations comprise liposomes. In still another embodiment, the synthetic nanocarriers of the first and/or second populations comprise metallic nanoparticles. In a further embodiment, the metallic nanoparticles comprise gold nanoparticles. In yet a further embodiment, the synthetic nanocarriers of the first and/or second populations comprise polymeric nanoparticles. In another embodiment, the polymeric nanoparticles comprise polymers that are non-methoxy-terminated, pluronic polymers. In still a further embodiment, the polymeric nanoparticles comprise a polyester, a polyester coupled to a polyether, polyamino acid, polycarbonate, polyacetal, polyketal, polysaccharide, polyethyloxazoline or polyethyleneimine. In another embodiment, the polyester comprises a poly(lactic acid), poly(glycolic acid), poly(lactic-co-glycolic acid) or polycaprolactone. In yet another embodiment, the polymeric nanoparticles comprise a polyester and a polyester coupled to a polyether. In still another embodiment, the polyether comprises polyethylene glycol or polypropylene glycol.

In another embodiment, the mean of a particle size distribution obtained using dynamic light scattering of the synthetic nanocarriers of the first and/or second population is a diameter greater than 100 nm. In another embodiment, the diameter is greater than 150 nm. In another embodiment, the diameter is greater than 200 nm. In another embodiment, the diameter is greater than 250 nm. In another embodiment, the diameter is greater than 300 nm.

In a further embodiment, the aspect ratio of the synthetic nanocarriers of the first population and/or second population is greater than 1:1, 1:1.2, 1:1.5, 1:2, 1:3, 1:5, 1:7 or 1:10.

In still a further embodiment, the composition further comprises a pharmaceutically acceptable excipient.

In yet a further embodiment, the method further comprises administering the therapeutic protein to the subject. In one embodiment, the therapeutic protein is administered prior to, concomitantly with or after the administration of the composition.

In another embodiment, one or more maintenance doses of the composition is administered to the subject.

In still another embodiment, the method further comprises assessing the generation of an undesired immune response in the subject prior to and/or after the administration of the composition and/or therapeutic protein. In another embodiment, the undesired immune response is the generation of therapeutic protein-specific antibodies and/or CD4+ T cell proliferation and/or activity specific to the therapeutic protein and/or B cell proliferation and/or activity specific to the therapeutic protein.

In one embodiment, the administering of the first and/or second population of synthetic nanocarriers and/or therapeutic protein is by intravenous, intraperitoneal, transmucosal, oral, subcutaneous, pulmonary, intranasal, intradermal or intramuscular administration. In another embodiment, the administering of the first and/or second population of synthetic nanocarriers and/or therapeutic protein is by inhalation or intravenous, subcutaneous or transmucosal administration.

In a further aspect, a method comprising (i) producing a first population of synthetic nanocarriers that are coupled to immunosuppressants, and (ii) producing a second population of synthetic nanocarriers that are coupled to therapeutic protein APC presentable antigens is provided. In one embodiment, the first population and second population are the same population. In another embodiment, the first population and second population are different populations. In yet another embodiment, the first and second populations of synthetic nanocarriers that are produced are as defined as provided anywhere herein.

In one embodiment, the method further comprises producing a dosage form of a composition comprising the first and second populations of synthetic nanocarriers produced. In still another embodiment, the method further comprises making a composition comprising the first population and second population of synthetic nanocarriers or the dosage form available to a subject for administration. In a further embodiment, the method further comprises assessing the reduction of an undesired immune response with a composition comprising the first population and second population of synthetic nanocarriers. In one embodiment, the undesired immune response is the generation of therapeutic protein-specific antibodies and/or CD4+ T cell proliferation and/or activity specific to the therapeutic protein and/or B cell proliferation and/or activity specific to the therapeutic protein.

In yet a further aspect, a process for producing a composition or dosage form comprising (i) a first population of synthetic nanocarriers that are coupled to immunosuppressants, and (ii) a second population of synthetic nanocarriers that are coupled to therapeutic protein APC presentable antigens, the process comprising the steps as defined in any of the methods provided herein is provided.

In another aspect, a composition or dosage form obtainable by any of the methods or processes provided herein is provided.

In yet another aspect, any of the compositions or dosage forms provided herein may be for use in therapy or prophylaxis.

In still another aspect, any of the compositions or dosage forms provided herein may be for use in a method of inducing a tolerogenic immune response to therapeutic protein antigens, cell-based therapy, protein replacement therapy, protein supplementation therapy or in any of the methods provided herein.

In a further aspect, use of any of the compositions or dosage forms provided herein for the manufacture of a medicament for use in a method of inducing a tolerogenic immune response to therapeutic protein antigens, cell-based therapy, protein replacement therapy, protein supplementation therapy or in any of the methods provided herein is provided.

In still another aspect, a dosage form comprising any of the compositions provided herein is provided.

In some embodiments of any of the compositions and methods provided, the compositions provided herein are administered prophylactically, early in the immune response (e.g., during an IgM phase) and/or prior to establishment of a mature memory response and/or an IgG antibody response. In embodiments of any of the compositions and methods provided herein, the compositions and methods may reduce the frequency of effector T cells reacting to antigen and/or their capacity to produce pro-inflammatory cytokines. In other embodiments of any of the compositions and methods provided herein, the compositions and methods increase the frequency of suppressive regulatory T or B cells that reduce the incidence of undesired therapeutic-protein immune responses.

In an embodiment of any of the compositions and methods provided herein, antigens that are proteins that comprise the aforementioned epitopes can be coupled to the synthetic nanocarriers. In another embodiment, polypeptides or peptides that comprise the aforementioned epitopes but additional amino acids that flank one or both ends of the epitope(s) can be coupled to the synthetic nanocarriers. In another embodiment, the epitopes themselves are coupled to the synthetic nanocarriers.

DETAILED DESCRIPTION OF THE INVENTION

Figure 1:
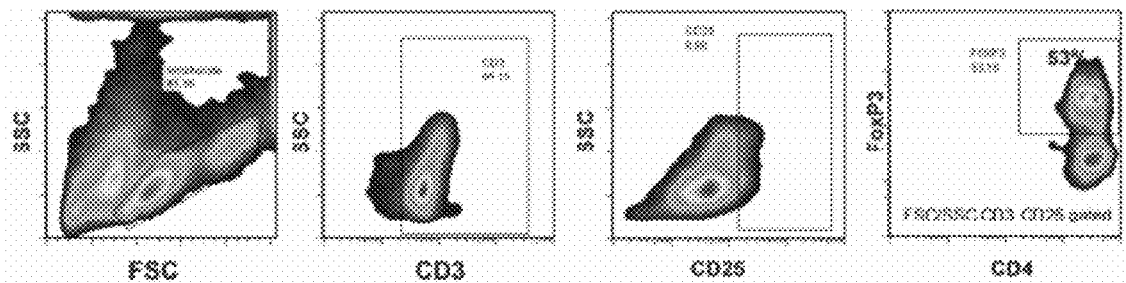
FIG. 1 shows results from a flow cytometric analysis of Treg.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules or a mixture of differing molecular weights of a single polymer species, reference to "a synthetic nanocarrier" includes a mixture of two or more such synthetic nanocarriers or a plurality of such synthetic nanocarriers, reference to "a DNA molecule" includes a mixture of two or more such DNA molecules or a plurality of such DNA molecules, reference to "an immunosuppressant" includes a mixture of two or more such materials or a plurality of immunosuppressant molecules, and the like.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein, the term "comprising" is inclusive and does not exclude additional, unrecited integers or method/process steps.

In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

A. Introduction

As previously mentioned, current conventional immunosuppressants are broad acting and generally result in an overall systemic downregulation of the immune system. The compositions and methods provided herein allow for more targeted immune effects by, for example, allowing for the targeted delivery to immune cells of interest. Thus, the compositions and methods can achieve immune suppression in a more directed manner. It has been found that delivering immunosuppressants and antigens comprising MHC Class II-restricted epitopes can effectively reduce the production of antigen-specific antibodies as well as reduce the generation of antigen-specific CD4+ T cells and B cells. As such immune responses can be beneficial in countering undesired immune responses that are generated during therapeutic treatment with therapeutic proteins, the invention is useful for promoting tolerogenic immune responses in subjects who have received, are receiving or will receive a therapeutic protein against which undesired immune responses are generated or are expected to be generated. The present invention, in some embodiments, prevents or suppresses undesired immune responses that may neutralize the beneficial effect of certain therapeutic treatments.

The inventors have unexpectedly and surprisingly discovered that the problems and limitations noted above can be overcome by practicing the invention disclosed herein. In particular, the inventors have unexpectedly discovered that it is possible to provide synthetic nanocarrier compositions, and related methods, that induce a tolerogenic immune response to therapeutic proteins. The compositions described herein include compositions that comprise (i) a first population of synthetic nanocarriers that are coupled to immunosuppressants, and (ii) a second population of synthetic nanocarriers that are coupled to therapeutic protein APC presentable antigens.

In another aspect, dosage forms of any of the compositions herein are provided. Such dosage forms can be administered to a subject, such as a subject in need thereof (e.g., in need of therapeutic protein-specific tolerogenic immune responses). In one embodiment, the subject is one who has been, is being or will be treated with a therapeutic protein against which undesired immune responses are generated or are expected to be generated.

In another aspect, any of the compositions provided herein is administered to a subject. The composition may be administered in an amount effective to reduce the generation of an undesired immune response against one or more therapeutic proteins. In one embodiment, a composition is administered to a subject according to a protocol that was previously shown to reduce the generation of an undesired immune response to therapeutic proteins in one or more subjects. The undesired immune response may be the generation of therapeutic protein-specific antibodies, CD4+ T cell proliferation and/or activity or B cell proliferation and/or activity or combinations thereof. The undesired immune responses may also be the generation of other immune responses downstream from the foregoing. In embodiments, the amounts effective, or protocol, generates, or has been shown to generate desired immune responses. Such immune responses include the reduction of any of, or combinations of, the foregoing. Such immune responses include any tolerogenic immune responses, such as those described herein.

The compositions may be administered to a subject prior to, concomitantly with or after the administration of a therapeutic protein to the subject. In some embodiments, the synthetic nanocarriers compositions are administered prior to the establishment of a mature memory response in the subject. The methods provided, in some embodiments, may further comprise administering the therapeutic protein. In embodiments, the compositions provided may also be administered as one or more maintenance doses to a subject that has received, is receiving or will receive a therapeutic protein. In such embodiments, the compositions provided are administered such that the generation of an undesired immune response is reduced for a certain length of time. Examples of such lengths of time are provided elsewhere herein.

In yet another aspect, a method of (i) producing a first population of synthetic nanocarriers that are coupled to immunosuppressants, and (ii) producing a second population of synthetic nanocarriers that are coupled to therapeutic protein APC presentable antigens is provided. In one embodiment, the method further comprises producing a dosage form comprising the first and second populations of synthetic nanocarriers.

The invention will now be described in more detail below.

B. Definitions

"Administering" or "administration" means providing a material to a subject in a manner that is pharmacologically useful.

"Amount effective" in the context of a composition or dosage form for administration to a subject refers to an amount of the composition or dosage form that produces one or more desired immune responses in the subject, for example, the generation of a tolerogenic immune response (e.g., a reduction in the proliferation, activation, induction, recruitment of antigen-specific CD4+ T cells or antigen-specific B cells or a reduction in the production of antigen-specific antibodies). Therefore, in some embodiments, an amount effective is any amount of a composition provided herein that produces one or more of these desired immune responses. This amount can be for in vitro or in vivo purposes. For in vivo purposes, the amount can be one that a clinician would believe may have a clinical benefit for a subject in need of antigen-specific tolerization.

Amounts effective can involve only reducing the level of an undesired immune response, although in some embodiments, it involves preventing an undesired immune response altogether. Amounts effective can also involve delaying the occurrence of an undesired immune response. An amount that is effective can also be an amount of a composition provided herein that produces a desired therapeutic endpoint or a desired therapeutic result. Amounts effective, preferably, result in a tolerogenic immune response in a subject to an antigen. The achievement of any of the foregoing can be monitored by routine methods.

In some embodiments of any of the compositions and methods provided, the amount effective is one in which the desired immune response persists in the subject for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer. In other embodiments of any of the compositions and methods provided, the amount effective is one which produces a measurable desired immune response, for example, a measurable decrease in an immune response (e.g., to a specific antigen), for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

In general, doses of the immunosuppressants and/or antigens in the compositions of the invention can range from about 10 µg/kg to about 100,000 µg/kg. In some embodiments, the doses can range from about 0.1 mg/kg to about 100 mg/kg. In still other embodiments, the doses can range from about 0.1 mg/kg to about 25 mg/kg, about 25 mg/kg to about 50 mg/kg, about 50 mg/kg to about 75 mg/kg or about 75 mg/kg to about 100 mg/kg. Alternatively, the dose can be administered based on the number of synthetic nanocarriers that provide the desired amount of immunosuppressants and/or antigens. For example, useful doses include greater than $10^6$, $10^7$, $10^8$, $10^9$ or $10^{10}$ synthetic nanocarriers per dose. Other examples of useful doses include from about $1 \times 10^6$ to about $1 \times 10^{10}$, about $1 \times 10^7$ to about $1 \times 10^9$ or about $1 \times 10^8$ to about $1 \times 10^9$ synthetic nanocarriers per dose.

"Antigen" means a B cell antigen or T cell antigen. "Type (s) of antigens" means molecules that share the same, or substantially the same, antigenic characteristics. In some embodiments, antigens may be proteins, polypeptides, peptides, lipoproteins, glycolipids, polynucleotides, polysaccharides or are contained or expressed in cells. In some embodiments, such as when the antigens are not well defined or characterized, the antigens may be contained within a cell or tissue preparation, cell debris, cell exosomes, conditioned media, etc. An antigen can be combined with the synthetic nanocarriers in the same form as what a subject is exposed to that causes an undesired immune response but may also be a fragment or derivative thereof. When a fragment or derivative, however, a desired immune response to the form encountered by such a subject is the preferable result with the compositions and methods provided.

"Antigen-specific" refers to any immune response that results from the presence of the antigen, or portion thereof, or that generates molecules that specifically recognize or bind the antigen. For example, where the immune response is antigen-specific antibody production, antibodies are produced that specifically bind the antigen. As another example, where the immune response is antigen-specific B cell or CD4+ T cell proliferation and/or activity, the proliferation and/or activity results from recognition of the antigen, or portion thereof, alone or in complex with MHC molecules, B cells, etc.

"Assessing an immune response" refers to any measurement or determination of the level, presence or absence, reduction, increase in, etc. of an immune response in vitro or in vivo. Such measurements or determinations may be performed on one or more samples obtained from a subject. Such assessing can be performed with any of the methods provided herein or otherwise known in the art.

An "at risk" subject is one in which a health practitioner believes has a chance of having a disease, disorder or condition as provided herein or is one a health practitioner believes has a chance of experiencing an undesired immune response as provided herein.

"Average", as used herein, refers to the arithmetic mean unless otherwise noted.

"B cell antigen" means any antigen that is or recognized by and triggers an immune response in a B cell (e.g., an antigen that is specifically recognized by a B cell or a receptor thereon). In some embodiments, an antigen that is a T cell antigen is also a B cell antigen. In other embodiments, the T cell antigen is not also a B cell antigen. B cell antigens include, but are not limited to proteins, peptides, etc. In some embodiments, the B cell antigen comprises a non-protein antigen (i.e., not a protein or peptide antigen).

"Concomitantly" means administering two or more substances to a subject in a manner that is correlated in time, preferably sufficiently correlated in time so as to provide a modulation in an immune response. In embodiments, concomitant administration may occur through administration of two or more substances in the same dosage form. In other embodiments, concomitant administration may encompass administration of two or more substances in different dosage forms, but within a specified period of time, preferably within 1 month, more preferably within 1 week, still more preferably within 1 day, and even more preferably within 1 hour.

"Couple" or "Coupled" or "Couples" (and the like) means to chemically associate one entity (for example a moiety) with another. In some embodiments, the coupling is covalent, meaning that the coupling occurs in the context of the presence of a covalent bond between the two entities. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In embodiments, encapsulation is a form of coupling.

"Derived" means prepared from a material or information related to a material but is not "obtained" from the material. Such materials may be substantially modified or processed forms of materials taken directly from a biological material. Such materials also include materials produced from information related to a biological material.

"Dosage form" means a pharmacologically and/or immunologically active material in a medium, carrier, vehicle, or device suitable for administration to a subject.

"Encapsulate" means to enclose at least a portion of a substance within a synthetic nanocarrier. In some embodiments, a substance is enclosed completely within a synthetic nanocarrier. In other embodiments, most or all of a substance that is encapsulated is not exposed to the local environment external to the synthetic nanocarrier. In other embodiments, no more than 50%, 40%, 30%, 20%, 10% or 5% (weight/weight) is exposed to the local environment. Encapsulation is distinct from absorption, which places most or all of a substance on a surface of a synthetic nanocarrier, and leaves the substance exposed to the local environment external to the synthetic nanocarrier.

"Epitope", also known as an antigenic determinant, is the part of an antigen that is recognized by the immune system, specifically by, for example, antibodies, B cells, or T cells. As used herein, "MHC Class I-restricted epitopes" are epitopes that are presented to immune cells by MHC class 1 molecules found on nucleated cells. "MHC Class II-restricted epitopes" are epitopes that are presented to immune cells by MHC class II molecules found on antigen-presenting cells (APCs), for example, on professional antigen-presenting immune cells, such as on macrophages, B cells, and dendritic cells, or on non-hematopoietic cells, such as hepatocytes. "B cell epitopes" are molecular structures that are recognized by antibodies or B cells. In some embodiments, the epitope itself is an antigen.

A number of epitopes are known to those of skill in the art, and exemplary epitopes suitable according to some aspects of this invention include, but are not limited to those listed in the Immune Epitope Database (www.immuneepitope.org, Vita R, Zarebski L, Greenbaum J A, Emami H, Hoof I, Salimi N, Damle R, Sette A, Peters B. The immune epitope database 2.0. Nucleic Acids Res. 2010 January; 38(Database issue): D854-62; the entire contents of which as well as all database entries of IEDB version 2.4, August 2011, and particularly all epitopes disclosed therein, are incorporated herein by reference). Epitopes can also be identified with publicly available algorithms, for example, the algorithms described in Wang P, Sidney J, Kim Y, Sette A, Lund O, Nielsen M, Peters B. 2010. peptide binding predictions for HLA DR, DP and DQ molecules. BMC Bioinformatics 2010, 11:568; Wang P, Sidney J, Dow C, Mothé B, Sette A, Peters B. 2008. A systematic assessment of MHC class II peptide binding predictions and evaluation of a consensus approach. PLoS Comput Biol. 4(4): e1000048; Nielsen M, Lund O. 2009. NN-align. An artificial neural network-based alignment algorithm for MHC class II peptide binding prediction. BMC Bioinformatics. 10:296; Nielsen M, Lundegaard C, Lund O. 2007. Prediction of MHC class II binding affinity using SMM-align, a novel stabilization matrix alignment method. BMC Bioinformatics. 8:238; Bui H H, Sidney J, Peters B, Sathiamurthy M, Sinichi A, Purton K A, Mothé B R, Chisari F V, Watkins D I, Sette A. 2005. Immunogenetics. 57:304-314; Sturniolo T, Bono E, Ding J, Raddrizzani L, Tuereci O, Sahin U, Braxenthaler M, Gallazzi F, Protti M P, Sinigaglia F, Hammer J. 1999. Generation of tissue-specific and promiscuous HLA ligand databases using DNA microarrays and virtual HLA class II matrices. Nat. Biotechnol. 17(6):555-561; Nielsen M, Lundegaard C, Worning P, Lauemoller S L, Lamberth K, Buus S, Brunak S, Lund O. 2003. Reliable prediction of T-cell epitopes using neural networks with novel sequence representations. Protein Sci 12:1007-1017; Bui H H, Sidney J, Peters B, Sathiamurthy M, Sinichi A, Purton K A, Mothe B R, Chisari F V, Watkins D I, Sette A. 2005. Automated generation and evaluation of specific MHC binding predictive tools: ARB matrix applications. Immunogenetics 57:304-314; Peters B, Sette A. 2005. Generating quantitative models describing the sequence specificity of biological processes with the stabilized matrix method. BMC Bioinformatics 6:132; Chou P Y, Fasman G D. 1978. Prediction of the secondary structure of proteins from their amino acid sequence. Adv Enzymol Relat Areas Mol Biol 47:45-148; Emini E A, Hughes J V, Perlow D S, Boger J. 1985. Induction of hepatitis A virus-neutralizing antibody by a virus-specific synthetic peptide. J Virol 55:836-839; Karplus P A, Schulz G E. 1985. Prediction of chain flexibility in proteins. Naturwissenschaften 72:212-213; Kolaskar A S, Tongaonkar P C. 1990. A semi-empirical method for prediction of antigenic determinants on protein antigens. FEBS Lett 276:172-174; Parker J M, Guo D, Hodges R S. 1986. New hydrophilicity scale derived from high-performance liquid chromatography peptide retention data: correlation of predicted surface residues with antigenicity and X-ray-derived accessible sites. Biochemistry 25:5425-5432; Larsen J E, Lund O, Nielsen M. 2006. Improved method for predicting linear B-cell epitopes. Immunome Res 2:2; Ponomarenko J V, Bourne P E. 2007. Antibody-protein interactions: benchmark datasets and prediction tools evaluation. BMC Struct Biol 7:64; Haste Andersen P, Nielsen M, Lund 0.2006. Prediction of residues in discontinuous B-cell epitopes using protein 3D structures. Protein Sci 15:2558-2567; Ponomarenko J V, Bui H, Li W, Fusseder N, Bourne P E, Sette A, Peters B. 2008. ElliPro: a new structure-based tool for the prediction of antibody epitopes. BMC Bioinformatics 9:514; Nielsen M, Lundegaard C, Blicher T, Peters B, Sette A, Justesen S, Buus S, and Lund 0.2008. PLoS Comput Biol. 4(7)e1000107. Quantitative predictions of peptide binding to any HLA-DR molecule of known sequence: NetMHCIIpan; the entire contents of each of which are incorporated herein by reference for disclosure of methods and algorithms for the identification of epitopes.

"Generating" means causing an action, such as an immune response (e.g., a tolerogenic immune response) to occur, either directly oneself or indirectly, such as, but not limited to, an unrelated third party that takes an action through reliance on one's words or deeds.

"Identifying" is any action or set of actions that allows a clinician to recognize a subject as one who may benefit from the methods and compositions provided herein. Preferably, the identified subject is one who is in need of a tolerogenic immune response as provided herein. The action or set of actions may be either directly oneself or indirectly, such as, but not limited to, an unrelated third party that takes an action through reliance on one's words or deeds.

"Immunosuppressant" means a compound that causes an APC to have an immunosuppressive (e.g., tolerogenic effect). An immunosuppressive effect generally refers to the production or expression of cytokines or other factors by the APC that reduces, inhibits or prevents an undesired immune response or that promotes a desired immune response. When the APC results in an immunosuppressive effect on immune cells that recognize an antigen presented by the APC, the immunosuppressive effect is said to be specific to the presented antigen. Such effect is also referred to herein as a tolerogenic effect. Without being bound by any particular theory, it is thought that the immunosuppressive or tolerogenic effect is a result of the immunosuppressant being delivered to the APC, preferably in the presence of an antigen (e.g., an administered antigen or one that is already present in vivo). Accordingly, the immunosuppressant includes compounds that provide a tolerogenic immune response to an antigen that may or may not be provided in the same composition or a different composition. In one embodiment, the immunosuppressant is one that causes an APC to promote a regulatory phenotype in one or more immune effector cells. For example, the regulatory phenotype may be characterized by the inhibition of the production, induction, stimulation or recruitment of antigen-specific CD4+ T cells or B cells, the inhibition of the production of antigen-specific antibodies, the production, induction, stimulation or recruitment of Treg cells (e.g., CD4+CD25highFoxP3+ Treg cells), etc. This may be the result of the conversion of CD4+ T cells or B cells to a regulatory phenotype. This may also be the result of induction of FoxP3 in other immune cells, such as CD8+ T cells, macrophages and iNKT cells. In one embodiment, the immunosuppressant is one that affects the response of the APC after it processes an antigen. In another embodiment, the immunosuppressant is not one that interferes with the processing of the antigen. In a further embodiment, the immunosuppressant is not an apoptotic-signaling molecule. In another embodiment, the immunosuppressant is not a phospholipid.

Immunosuppressants include, but are not limited to, statins; mTOR inhibitors, such as rapamycin or a rapamycin analog; TGF-β signaling agents; TGF-β receptor agonists; histone deacetylase inhibitors, such as Trichostatin A; corticosteroids; inhibitors of mitochondrial function, such as rotenone; P38 inhibitors; NF-κβ inhibitors, such as 6Bio, Dexamethasone, TCPA-1, IKK VII; adenosine receptor agonists; prostaglandin E2 agonists (PGE2), such as Misoprostol; phosphodiesterase inhibitors, such as phosphodiesterase 4 inhibitor (PDE4), such as Rolipram; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors; PI3 KB inhibitors, such as TGX-221; autophagy inhibitors, such as 3-Methyladenine; aryl hydrocarbon receptor inhibitors; proteasome inhibitor I (PSI); and oxidized ATPs, such as P2X receptor blockers. Immunosuppressants also include IDO, vitamin D3, cyclosporins, such as cyclosporine A, aryl hydrocarbon receptor inhibitors, resveratrol, azathiopurine (Aza), 6-mercaptopurine (6-MP), 6-thioguanine (6-TG), FK506, sanglifehrin A, salmeterol, mycophenolate mofetil (MMF), aspirin and other COX inhibitors, niflumic acid, estriol and triptolide. In embodiments, the immunosuppressant may comprise any of the agents provided herein.

The immunosuppressant can be a compound that directly provides the immunosuppressive (e.g., tolerogenic) effect on APCs or it can be a compound that provides the immunosuppressive (e.g., tolerogenic) effect indirectly (i.e., after being processed in some way after administration). Immunosuppressants, therefore, include prodrug forms of any of the compounds provided herein.

Immunosuppressants also include nucleic acids that encode the peptides, polypeptides or proteins provided herein that result in an immunosuppressive (e.g., tolerogenic) immune response. In embodiments, therefore, the immunosuppressant is a nucleic acid that encodes a peptide, polypeptide or protein that results in an immunosuppressive (e.g., tolerogenic) immune response, and it is the nucleic acid that is coupled to the synthetic nanocarrier.

The nucleic acid may be DNA or RNA, such as mRNA. In embodiments, the inventive compositions comprise a complement, such as a full-length complement, or a degenerate (due to degeneracy of the genetic code) of any of the nucleic acids provided herein. In embodiments, the nucleic acid is an expression vector that can be transcribed when transfected into a cell line. In embodiments, the expression vector may comprise a plasmid, retrovirus, or an adenovirus amongst others. Nucleic acids can be isolated or synthesized using standard molecular biology approaches, for example by using a polymerase chain reaction to produce a nucleic acid fragment, which is then purified and cloned into an expression vector. Additional techniques useful in the practice of this invention may be found in Current Protocols in Molecular Biology 2007 by John Wiley and Sons, Inc.; Molecular Cloning: A Laboratory Manual (Third Edition) Joseph Sambrook, Peter MacCallum Cancer Institute, Melbourne, Australia; David Russell, University of Texas Southwestern Medical Center, Dallas, Cold Spring Harbor.

In embodiments, the immunosuppressants provided herein are coupled to synthetic nanocarriers. In preferable embodiments, the immunosuppressant is an element that is in addition to the material that makes up the structure of the synthetic nanocarrier. For example, in one embodiment, where the synthetic nanocarrier is made up of one or more polymers, the immunosuppressant is a compound that is in addition and coupled to the one or more polymers. As another example, in one embodiment, where the synthetic nanocarrier is made up of one or more lipids, the immunosuppressant is again in addition and coupled to the one or more lipids. In embodiments, such as where the material of the synthetic nanocarrier also results in an immunosuppressive (e.g., tolerogenic) effect, the immunosuppressant is an element present in addition to the material of the synthetic nanocarrier that results in an immunosuppressive (e.g., tolerogenic) effect.

Other exemplary immunosuppressants include, but are not limited, small molecule drugs, natural products, antibodies (e.g., antibodies against CD20, CD3, CD4), biologics-based drugs, carbohydrate-based drugs, nanoparticles, liposomes, RNAi, antisense nucleic acids, aptamers, methotrexate, NSAIDs; fingolimod; natalizumab; alemtuzumab; anti-CD3;

tacrolimus (FK506), etc. Further immunosuppressants, are known to those of skill in the art, and the invention is not limited in this respect.

"Load" of the immunosuppressant or therapeutic protein APC presentable antigen is the amount of the immunosuppressant or therapeutic protein APC presentable antigen coupled to a synthetic nanocarrier based on the total weight of materials in an entire synthetic nanocarrier (weight/weight). Generally, the load is calculated as an average across a population of synthetic nanocarriers. In one embodiment, the load of the immunosuppressant on average across the first population of synthetic nanocarriers is between 0.0001% and 50%. In another embodiment, the load of the therapeutic protein APC presentable antigen on average across the first and/or second population of synthetic nanocarriers is between 0.0001% and 50%. In yet another embodiment, the load of the immunosuppressant and/or therapeutic protein APC presentable antigen is between 0.01% and 20%. In a further embodiment, the load of the immunosuppressant and/or therapeutic protein APC presentable antigen is between 0.1% and 10%. In still a further embodiment, the load of the immunosuppressant and/or therapeutic protein APC presentable antigen is between 1% and 10%. In yet another embodiment, the load of the immunosuppressant and/or the therapeutic protein APC presentable antigen is at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least at least 7%, at least 8%, at least 9%, at least 10%, at least 11%, at least 12%, at least 13%, at least 14%, at least 15%, at least 16%, at least 17%, at least 18%, at least 19% or at least 20% on average across the population of synthetic nanocarriers. In yet a further embodiment, the load of the immunosuppressant and/or the therapeutic protein APC presentable antigen is 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19% or 20% on average across the population of synthetic nanocarriers. In some embodiments of the above embodiments, the load of the immunosuppressant and/or the therapeutic protein APC presentable antigen is no more than 25% on average across a population of synthetic nanocarriers. In embodiments, the load is calculated as described in the Examples.

In embodiments of any of the compositions and methods provided, the load is calculated as follows: Approximately 3 mg of synthetic nanocarriers are collected and centrifuged to separate supernatant from synthetic nanocarrier pellet. Acetonitrile is added to the pellet, and the sample is sonicated and centrifuged to remove any insoluble material. The supernatant and pellet are injected on RP-HPLC and absorbance is read at 278 nm. The μg found in the pellet is used to calculate % entrapped (load), μg in supernatant and pellet are used to calculate total μg recovered.

"Maintenance dose" refers to a dose that is administered to a subject, after an initial dose has resulted in an immunosuppressive (e.g., tolerogenic) response in a subject, to sustain a desired immunosuppressive (e.g., tolerogenic) response. A maintenance dose, for example, can be one that maintains the tolerogenic effect achieved after the initial dose, prevents an undesired immune response in the subject, or prevents the subject becoming a subject at risk of experiencing an undesired immune response, including an undesired level of an immune response. In some embodiments, the maintenance dose is one that is sufficient to sustain an appropriate level of a desired immune response.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheroidal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is equal to or greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 μm. Preferably, a minimum dimension of at least 75%, preferably at least 80%, more preferably at least 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of inventive synthetic nanocarriers may vary depending on the embodiment. For instance, aspect ratios of the maximum to minimum dimensions of the synthetic nanocarriers may vary from 1:1 to 1,000,000:1, preferably from 1:1 to 100,000:1, more preferably from 1:1 to 10,000:1, more preferably from 1:1 to 1000:1, still more preferably from 1:1 to 100:1, and yet more preferably from 1:1 to 10:1. Preferably, a maximum dimension of at least 75%, preferably at least 80%, more preferably at least 90%, of the synthetic nanocarriers in a sample, based on the total number of synthetic nanocarriers in the sample is equal to or less than 3 μm, more preferably equal to or less than 2 μm, more preferably equal to or less than 1 μm, more preferably equal to or less than 800 nm, more preferably equal to or less than 600 nm, and more preferably still equal to or less than 500 nm. In preferred embodiments, a minimum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120 nm, more preferably equal to or greater than 130 nm, more preferably equal to or greater than 140 nm, and more preferably still equal to or greater than 150 nm. Measurement of synthetic nanocarrier dimensions (e.g., diameter) is obtained by suspending the synthetic nanocarriers in a liquid (usually aqueous) media and using dynamic light scattering (DLS) (e.g. using a Brookhaven ZetaPALS instrument). For example, a suspension of synthetic nanocarriers can be diluted from an aqueous buffer into purified water to achieve a final synthetic nanocarrier suspension concentration of approximately 0.01 to 0.1 mg/mL. The diluted suspension may be prepared directly inside, or transferred to, a suitable cuvette for DLS analysis. The cuvette may then be placed in the DLS, allowed to equilibrate to the controlled temperature, and then scanned for sufficient time to acquire a stable and reproducible distribution based on appropriate inputs for viscosity of the medium and refractive indicies of the sample. The effective diameter, or mean of the distribution, is then reported. "Dimension" or "size" or "diameter" of synthetic nanocarriers means the mean of a particle size distribution obtained using dynamic light scattering.

"MHC" refers to major histocompatibility complex, a large genomic region or gene family found in most vertebrates that encodes MHC molecules that display fragments or epitopes of processed proteins on the cell surface. The presentation of MHC:peptide on cell surfaces allows for surveillance by immune cells, usually a T cell. There are two general classes of MHC molecules: Class I and Class II. Generally, Class I MHC molecules are found on nucleated cells and present peptides to cytotoxic T cells. Class II MHC molecules are found on certain immune cells, chiefly macrophages, B cells and dendritic cells, collectively known as professional APCs. The best-known genes in the MHC region are the subset that encodes antigen-presenting proteins on the cell surface. In humans, these genes are referred to as human leukocyte antigen (HLA) genes.

"Non-methoxy-terminated polymer" means a polymer that has at least one terminus that ends with a moiety other than methoxy. In some embodiments, the polymer has at least two termini that ends with a moiety other than methoxy. In other embodiments, the polymer has no termini that ends with methoxy. "Non-methoxy-terminated, pluronic polymer" means a polymer other than a linear pluronic polymer with methoxy at both termini. Polymeric nanoparticles as provided herein can comprise non-methoxy-terminated polymers or non-methoxy-terminated, pluronic polymers.

"Obtained" means taken directly from a material and used with substantially no modification and/or processing.

"Pharmaceutically acceptable excipient" means a pharmacologically inactive material used together with the recited synthetic nanocarriers to formulate the inventive compositions. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers.

"Protocol" refers to any dosing regimen of one or more substances to a subject. A dosing regimen may include the amount, frequency and/or mode of administration. In some embodiments, such a protocol may be used to administer one or more compositions of the invention to one or more test subjects. Immune responses in these test subject can then be assessed to determine whether or not the protocol was effective in reducing an undesired immune response or generating a desired immune response (e.g., the promotion of a tolerogenic effect). Any other therapeutic and/or prophylactic effect may also be assessed instead of or in addition to the aforementioned immune responses. Whether or not a protocol had a desired effect can be determined using any of the methods provided herein or otherwise known in the art. For example, a population of cells may be obtained from a subject to which a composition provided herein has been administered according to a specific protocol in order to determine whether or not specific immune cells, cytokines, antibodies, etc. were reduced, generated, activated, etc. Useful methods for detecting the presence and/or number of immune cells include, but are not limited to, flow cytometric methods (e.g., FACS) and immunohistochemistry methods. Antibodies and other binding agents for specific staining of immune cell markers, are commercially available. Such kits typically include staining reagents for multiple antigens that allow for FACS-based detection, separation and/or quantitation of a desired cell population from a heterogeneous population of cells.

"Providing a subject" is any action or set of actions that causes a clinician to come in contact with a subject and administer a composition provided herein thereto or to perform a method provided herein thereupon. Preferably, the subject is one who is in need of a tolerogenic immune response as provided herein. The action or set of actions may be either directly oneself or indirectly, such as, but not limited to, an unrelated third party that takes an action through reliance on one's words or deeds.

"Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like.

"Substantially no B cell epitopes" refers to the absence of B cell epitopes in an amount (by itself, within the context of the antigen, in conjunction with a carrier or in conjunction with an inventive composition) that stimulates substantial activation of a B cell response. In embodiments, a composition with substantially no B cell epitopes does not contain a measurable amount of B cell epitopes of an antigen. In other embodiments, such a composition may comprise a measurable amount of B cell epitopes of an antigen but said amount is not effective to generate a measurable B cell immune response (by itself, within the context of the antigen, in conjunction with a carrier or in conjunction with an inventive composition), such as antigen-specific antibody production or antigen-specific B cell proliferation and/or activity, or is not effective to generate a significant measurable B cell immune response (by itself, within the context of the antigen, in conjunction with a carrier or in conjunction with an inventive composition). In some embodiments, a significant measurable B cell immune response is one that produces or would be expected to produce an adverse clinical result in a subject. In other embodiments, a significant measurable B cell immune response is one that is greater than the level of the same type of immune response (e.g., antigen-specific antibody production or antigen-specific B cell proliferation and/or activity) produced by a control antigen (e.g., one known not to comprise B cell epitopes of the antigen or to stimulate B cell immune responses). In some embodiments, a significant measurable B cell immune response, such as a measurement of antibody titers (e.g., by ELISA) is 2-fold, 3-fold, 4-fold, 5-fold, 6-fold, 7-fold, 8-fold, 9-fold, 10-fold, 15-fold, 20-fold or more greater than the same type of response produced by a control (e.g., control antigen). In other embodiments, a composition with substantially no B cell epitopes is one that produces little to no antigen-specific antibody titers (by itself, within the context of the antigen, in conjunction with a carrier or in conjunction with an inventive composition). Such compositions include those that produce an antibody titer (as an EC50 value) of less than 500, 400, 300, 200, 100, 50, 40, 30, 20 or 10. In other embodiments, a significant measurable B cell immune response, is a measurement of the number or proliferation of B cells that is 10%, 25%, 50%, 100%, 2-fold, 3-fold, 4-fold, 5-fold, 6-fold, 7-fold, 8-fold, 9-fold, 10-fold, 15-fold, 20-fold or more greater that the same type of response produced by a control. Other methods for measuring B cell responses are known to those of ordinary skill in the art.

In embodiments, to ensure that a composition comprises substantially no B cell epitopes, antigens are selected such that they do not comprise B cell epitopes for coupling to the synthetic nanocarriers as provided herein. In other embodiments, to ensure that a composition comprises substantially no B cell epitopes of an antigen, the synthetic nanocarriers coupled to the antigen are produced and tested for B cell immune responses (e.g., antigen-specific antibody production, B cell proliferation and/or activity). Compositions that exhibit the desired properties may then be selected.

"Synthetic nanocarrier(s)" means a discrete object that is not found in nature, and that possesses at least one dimension that is less than or equal to 5 microns in size. Albumin nanoparticles are generally included as synthetic nanocarriers, however in certain embodiments the synthetic nanocarriers do not comprise albumin nanoparticles. In embodiments, inventive synthetic nanocarriers do not comprise chitosan. In other embodiments, inventive synthetic nanocarriers are not lipid-based nanoparticles. In further embodiments, inventive synthetic nanocarriers do not comprise a phospholipid.

A synthetic nanocarrier can be, but is not limited to, one or a plurality of lipid-based nanoparticles (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptide or protein-based particles (also referred to herein as protein particles, i.e., particles where the majority of the material that makes up their structure are peptides or proteins) (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid coupled virus-like particles disclosed in published US Patent Application 20060251677 to Bachmann et al., (9) the virus-like particles disclosed in WO2010047839A1 or WO2009106999A2, (10) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010), or (11) apoptotic cells, apoptotic bodies or the synthetic or semisynthetic mimics disclosed in U.S. Publication 2002/0086049. In embodiments, synthetic nanocarriers may possess an aspect ratio greater than 1:1, 1:1.2, 1:1.5, 1:2, 1:3, 1:5, 1:7, or greater than 1:10.

Synthetic nanocarriers according to the invention that have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers exclude virus-like particles. In embodiments, synthetic nanocarriers may possess an aspect ratio greater than 1:1, 1:1.2, 1:1.5, 1:2, 1:3, 1:5, 1:7, or greater than 1:10.

"T cell antigen" means a CD4+ T-cell antigen or CD8+ cell antigen. "CD4+ T-cell antigen" means any antigen that is recognized by and triggers an immune response in a CD4+ T-cell e.g., an antigen that is specifically recognized by a T-cell receptor on a CD4+ T cell via presentation of the antigen or portion thereof bound to a Class II major histocompatability complex molecule (MHC). "CD8+ T cell antigen" means any antigen that is recognized by and triggers an immune response in a CD8+ T-cell e.g., an antigen that is specifically recognized by a T-cell receptor on a CD8+ T cell via presentation of the antigen or portion thereof bound to a Class I major histocompatability complex molecule (MHC). In some embodiments, an antigen that is a T cell antigen is also a B cell antigen. In other embodiments, the T cell antigen is not also a B cell antigen. T cell antigens generally are proteins or peptides.

A "therapeutic protein" refers to any protein or protein-based therapy that may be administered to a subject and have a therapeutic effect. Such therapies include protein replacement and protein supplementation therapies. Such therapies also include the administration of exogenous or foreign protein, antibody therapies, and cell or cell-based therapies. Therapeutic proteins include enzymes, enzyme cofactors, hormones, blood clotting factors, cytokines, growth factors, monoclonal antibodies and polyclonal antibodies. Examples of other therapeutic proteins are provided elsewhere herein. Therapeutic proteins may be produced in, on or by cells and may be obtained from such cells or administered in the form of such cells. In embodiments, the therapeutic protein is produced in, on or by mammalian cells, insect cells, yeast cells, bacteria cells, plant cells, transgenic animal cells, transgenic plant cells, etc. The therapeutic protein may be recombinantly produced in such cells. The therapeutic protein may be produced in, on or by a virally transformed cell. The therapeutic protein may also be produced in, on or by autologous cells that have been transfected, transduced or otherwise manipulated to express it. Alternatively, the therapeutic protein may be administered as a nucleic acid or by introducing a nucleic acid into a virus, VLP, liposome, etc. Alternatively, the therapeutic protein may be obtained from such forms and administered as the therapeutic protein itself. Subjects, therefore, include any subject that has received, is receiving or will receive any of the foregoing. Such subject includes subjects that have received, is receiving or will receive gene therapy, autologous cells that have been transfected, transduced or otherwise manipulated to express a therapeutic protein, polypeptide or peptide; or cells that express a therapeutic protein, polypeptide or peptide.

"Therapeutic protein APC presentable antigen" means an antigen that is associated with a therapeutic protein (i.e., the therapeutic protein or a fragment thereof can generate an immune response against the therapeutic protein (e.g., the production of therapeutic protein-specific antibodies)). Generally, therapeutic protein APC presentable antigens can be presented for recognition by the immune system (e.g., cells of the immune system, such as presented by antigen presenting cells, including but not limited to dendritic cells, B cells or macrophages). The therapeutic protein APC presentable antigen can be presented for recognition by, for example, T cells.

Such antigens may be recognized by and trigger an immune response in a T cell via presentation of an epitope of the antigen bound to a Class I or Class II major histocompatability complex molecule (MHC). Therapeutic protein APC presentable antigens generally include proteins, polypeptides, peptides, lipoproteins, or are contained or expressed in, on or by cells. The therapeutic protein antigens, in some embodiments, are coupled to synthetic nanocarriers and comprise MHC Class I-restricted epitopes and/or MHC Class II-restricted epitopes and/or B cell epitopes. In other embodiments, the antigens do not comprise B cell epitopes, such as when the inclusion of the B cell epitopes would exacerbate an undesired immune response. In other embodiments, the antigens comprise MHC Class II-restricted epitopes and substantially no B cell epitopes. Preferably, one or more tolerogenic immune responses specific to the therapeutic protein result with the compositions provided herein.

"Tolerogenic immune response" means any immune response that can lead to immune suppression specific to an antigen or a cell, tissue, organ, etc. that expresses such an antigen. Such immune responses include any reduction, delay or inhibition in an undesired immune response specific to the antigen or cell, tissue, organ, etc. that expresses such antigen. Such immune responses also include any stimulation, production, induction, promotion or recruitment in a desired immune response specific to the antigen or cell, tissue, organ, etc. that expresses such antigen. Tolerogenic immune responses, therefore, include the absence of or reduction in an undesired immune response to an antigen that can be mediated by antigen reactive cells as well as the presence or promotion of suppressive cells. Tolerogenic immune responses as provided herein include immunological tolerance. To "generate a tolerogenic immune response" refers to the generation of any of the foregoing immune responses specific to an antigen or cell, tissue, organ, etc. that expresses such antigen. The tolerogenic immune response can be the result of MHC Class I-restricted presentation and/or MHC Class II-restricted presentation and/or B cell presentation and/or presentation by CD1d, etc.

Tolerogenic immune responses include any reduction, delay or inhibition in CD4+ T cell, CD8+ T cell or B cell proliferation and/or activity. Tolerogenic immune responses also include a reduction in antigen-specific antibody production. Tolerogenic immune responses can also include any response that leads to the stimulation, induction, production or recruitment of regulatory cells, such as CD4+ Treg cells, CD8+ Treg cells, Breg cells, etc. In some embodiments, the tolerogenic immune response, is one that results in the conversion to a regulatory phenotype characterized by the production, induction, stimulation or recruitment of regulatory cells.

Tolerogenic immune responses also include any response that leads to the stimulation, production or recruitment of CD4+ Treg cells and/or CD8+ Treg cells. CD4+ Treg cells can express the transcription factor FoxP3 and inhibit inflammatory responses and auto-immune inflammatory diseases (Human regulatory T cells in autoimmune diseases. Cvetanovich G L, Hafler D A. Curr Opin Immunol. 2010 December; 22(6): 753-60. Regulatory T cells and autoimmunity. Vila J, Isaacs J D, Anderson A E. Curr Opin Hematol. 2009 July; 16(4):274-9). Such cells also suppress T-cell help to B-cells and induce tolerance to both self and foreign antigens (Therapeutic approaches to allergy and autoimmunity based on FoxP3+ regulatory T-cell activation and expansion. Miyara M, Wing K, Sakaguchi S. J Allergy Clin Immunol. 2009 April; 123(4): 749-55). CD4+ Treg cells recognize antigen when presented by Class II proteins on APCs. CD8+ Treg cells, which recognize antigen presented by Class I (and Qa-1), can also suppress T-cell help to B-cells and result in activation of antigen-specific suppression inducing tolerance to both self and foreign antigens. Disruption of the interaction of Qa-1 with CD8+ Treg cells has been shown to dysregulate immune responses and results in the development of auto-antibody formation and an auto-immune lethal systemic-lupus-erythematosus (Kim et al., Nature. 2010 Sep. 16, 467 (7313): 328-32). CD8+ Treg cells have also been shown to inhibit models of autoimmune inflammatory diseases including rheumatoid arthritis and colitis (CD4+CD25+ regulatory T cells in autoimmune arthritis. Oh S, Rankin A L, Caton A J. Immunol. Rev. 2010 January; 233(1):97-111. Regulatory T cells in inflammatory bowel disease. Boden E K, Snapper S B. Curr Opin Gastroenterol. 2008 November; 24(6):733-41). In some embodiments, the compositions provided can effectively result in both types of responses (CD4+ Treg and CD8+ Treg). In other embodiments, FoxP3 can be induced in other immune cells, such as macrophages, iNKT cells, etc., and the compositions provided herein can result in one or more of these responses as well.

Tolerogenic immune responses also include, but are not limited to, the induction of regulatory cytokines, such as Treg cytokines; induction of inhibitory cytokines; the inhibition of inflammatory cytokines (e.g., IL-4, IL-1b, IL-5, TNF-α, IL-6, GM-CSF, IFN-γ, IL-2, IL-9, IL-12, IL-17, IL-18, IL-21, IL-22, IL-23, M-CSF, C reactive protein, acute phase protein, chemokines (e.g., MCP-1, RANTES, MIP-1α, MIP-1β, MIG, ITAC or IP-10), the production of anti-inflammatory cytokines (e.g., IL-4, IL-13, IL-10, etc.), chemokines (e.g., CCL-2, CXCL8), proteases (e.g., MMP-3, MMP-9), leukotrienes (e.g., CysLT-1, CysLT-2), prostaglandins (e.g., PGE2) or histamines; the inhibition of polarization to a Th17, Th1 or Th2 immune response; the inhibition of effector cell-specific cytokines: Th17 (e.g., IL-17, IL-25), Th1 (IFN-γ), Th2 (e.g., IL-4, IL-13); the inhibition of Th1-, Th2- or TH17-specific transcription factors; the inhibition of proliferation of effector T cells; the induction of apoptosis of effector T cells; the induction of tolerogenic dendritic cell-specific genes, the induction of FoxP3 expression, the inhibition of IgE induction or IgE-mediated immune responses; the inhibition of antibody responses (e.g., antigen-specific antibody production); the inhibition of T helper cell response; the production of TGF-β and/or IL-10; the inhibition of effector function of autoantibodies (e.g., inhibition in the depletion of cells, cell or tissue damage or complement activation); etc.

Any of the foregoing may be measured in vivo in one or more animal models or may be measured in vitro. One of ordinary skill in the art is familiar with such in vivo or in vitro measurements. Undesired immune responses or tolerogenic immune responses can be monitored using, for example, methods of assessing immune cell number and/or function, tetramer analysis, ELISPOT, flow cytometry-based analysis of cytokine expression, cytokine secretion, cytokine expression profiling, gene expression profiling, protein expression profiling, analysis of cell surface markers, PCR-based detection of immune cell receptor gene usage (see T. Clay et al., "Assays for Monitoring Cellular Immune Response to Active Immunotherapy of Cancer" Clinical Cancer Research 7:1127-1135 (2001)), etc. Undesired immune responses or tolerogenic immune responses may also be monitored using, for example, methods of assessing protein levels in plasma or serum, immune cell proliferation and/or functional assays, etc. In some embodiments, tolerogenic immune responses can be monitored by assessing the induction of FoxP3. In addition, specific methods are described in more detail in the Examples.

Preferably, tolerogenic immune responses lead to the inhibition of the development, progression or pathology of the diseases, disorders or conditions described herein. Whether or not the inventive compositions can lead to the inhibition of the development, progression or pathology of the diseases, disorders or conditions described herein can be measured with animal models of such diseases, disorders or conditions. In some embodiments, the reduction of an undesired immune response or generation of a tolerogenic immune response may be assessed by determining clinical endpoints, clinical efficacy, clinical symptoms, disease biomarkers and/or clinical scores. Undesired immune responses or tolerogenic immune responses can also be assessed with diagnostic tests to assess the presence or absence of a disease, disorder or condition as provided herein. Undesired immune responses can further be assessed by methods of measuring therapeutic proteins levels and/or function in a subject.

In some embodiments, monitoring or assessing the generation of an undesired immune response or a tolerogenic immune response in a subject can be prior to the administration of a composition of synthetic nanocarriers provided herein and/or prior to administration of a therapeutic protein. In other embodiments, assessing the generation of an undesired immune response or tolerogenic immune response can be after administration of a composition of synthetic nanocarriers provided herein and/or and after administration of a therapeutic protein. In some embodiments, the assessment is done after administration of the composition of synthetic nanocarriers, but prior to administration of the therapeutic protein. In other embodiments, the assessment is done after administration of the therapeutic protein, but prior to administration of the composition. In still other embodiments, the assessment is performed prior to both the administration of the synthetic nanocarriers and the therapeutic protein, while in yet other embodiments the assessment is performed after administration of both the synthetic nanocarriers and the therapeutic protein. In further embodiments, the assessment is performed both prior to and after the administration of the synthetic nanocarriers and/or the therapeutic protein. In still other embodiments, the assessment is performed more than once on the subject to determine that a desirable immune state is maintained in the subject, such as a subject that has been, is being or will be administered a therapeutic protein.

An antibody response can be assessed by determining one or more antibody titers. "Antibody titer" means a measurable level of antibody production. Methods for measuring antibody titers are known in the art and include Enzyme-linked Immunosorbent Assay (ELISA). In embodiments, the antibody response can be quantitated, for example, as the number of antibodies, concentration of antibodies or titer. The values can be absolute or they can be relative. Assays for quantifying an antibody response include antibody capture assays, enzyme-linked immunosorbent assays (ELISAs), inhibition liquid phase absorption assays (ILPAAs), rocket immunoelectrophoresis (RIE) assays and line immunoelectrophoresis (LIE) assays. When an antibody response is compared to another antibody response the same type of quantitative value (e.g., titer) and method of measurement (e.g., ELISA) is preferably used to make the comparison.

An ELISA method for measuring an antibody titer, for example, a typical sandwich ELISA, may consist of the following steps (i) preparing an ELISA-plate coating material such that the antibody target of interest is coupled to a substrate polymer or other suitable material (ii) preparing the coating material in an aqueous solution (such as PBS) and delivering the coating material solution to the wells of a multiwell plate for overnight deposition of the coating onto the multiwell plate (iii) thoroughly washing the multiwell plate with wash buffer (such as 0.05% Tween-20 in PBS) to remove excess coating material (iv) blocking the plate for nonspecific binding by applying a diluent solution (such as 10% fetal bovine serum in PBS), (v) washing the blocking/diluent solution from the plate with wash buffer (vi) diluting the serum sample(s) containing antibodies and appropriate standards (positive controls) with diluent as required to obtain a concentration that suitably saturates the ELISA response (vii) serially diluting the plasma samples on the multiwell plate such to cover a range of concentrations suitable for generating an ELISA response curve (viii) incubating the plate to provide for antibody-target binding (ix) washing the plate with wash buffer to remove antibodies not bound to antigen (x) adding an appropriate concentration of a secondary detection antibody in same diluent such as a biotin-coupled detection antibody capable of binding the primary antibody (xi) incubating the plate with the applied detection antibody, followed by washing with wash buffer (xii) adding an enzyme such as streptavidin-HRP (horse radish peroxidase) that will bind to biotin found on biotinylated antibodies and incubating (xiii) washing the multiwell plate (xiv) adding substrate(s) (such as TMB solution) to the plate (xv) applying a stop solution (such as 2N sulfuric acid) when color development is complete (xvi) reading optical density of the plate wells at a specific wavelength for the substrate (450 nm with subtraction of readings at 570 nm) (xvi) applying a suitable multiparameter curve fit to the data and defining half-maximal effective concentration (EC50) as the concentration on the curve at which half the maximum OD value for the plate standards is achieved.

"Undesired immune response" refers to any undesired immune response that results from exposure to an antigen, promotes or exacerbates a disease, disorder or condition provided herein (or a symptom thereof), or is symptomatic of a disease, disorder or condition provided herein. Such immune responses generally have a negative impact on a subject's health or is symptomatic of a negative impact on a subject's health. Undesired immune responses include antigen-specific antibody production, antigen-specific B cell proliferation and/or activity or antigen-specific CD4+ T cell proliferation and/or activity.

C. Inventive Compositions

Provided herein are tolerogenic synthetic nanocarrier compositions comprising immunosuppressants and therapeutic protein APC presentable antigens and related methods. Such compositions and methods are useful for reducing the generation of undesired immune responses and promoting the generation of tolerogenic immune responses that are specific to therapeutic proteins. The compositions can be administered to subjects in which a tolerogenic immune response to therapeutic proteins is desired. Such subjects include those that have been, are being or will be administered a therapeutic protein. In embodiments, a subject is administered the synthetic nanocarriers provided herein and is then administered one or more therapeutic proteins. In other embodiments, a subject is administered a therapeutic protein and then the synthetic nanocarriers provided. In still other embodiments, the synthetic nanocarriers and the one or more therapeutic proteins are administered concomitantly.

As mentioned above, the synthetic nanocarriers are designed to comprise immunosuppressants and, in some embodiments, antigen against which a tolerogenic effect is desired. In embodiments, the antigens comprise MHC Class II-restricted epitopes that when presented in conjunction with immunosuppressant can lead to tolerogenic effects, such as the reduction in antigen-specific CD4+ T cell proliferation and/or activity. The resulting tolerogenic effects also include a reduction in antigen-specific B cell proliferation and/or activity and/or a reduction in antigen-specific antibody production. A wide variety of synthetic nanocarriers can be used according to the invention. In some embodiments, synthetic nanocarriers are spheres or spheroids. In some embodiments, synthetic nanocarriers are flat or plate-shaped. In some embodiments, synthetic nanocarriers are cubes or cubic. In some embodiments, synthetic nanocarriers are ovals or ellipses. In some embodiments, synthetic nanocarriers are cylinders, cones, or pyramids.

In some embodiments, it is desirable to use a population of synthetic nanocarriers that is relatively uniform in terms of size, shape, and/or composition so that each synthetic nanocarrier has similar properties. For example, at least 80%, at least 90%, or at least 95% of the synthetic nanocarriers, based on the total number of synthetic nanocarriers, may have a minimum dimension or maximum dimension that falls within 5%, 10%, or 20% of the average diameter or average dimension of the synthetic nanocarriers. In some embodiments, a population of synthetic nanocarriers may be heterogeneous with respect to size, shape, and/or composition.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g. a polymeric core) and the shell is a second layer (e.g. a lipid bilayer or monolayer). Synthetic nanocarriers may comprise a plurality of different layers.

In some embodiments, synthetic nanocarriers may optionally comprise one or more lipids. In some embodiments, a synthetic nanocarrier may comprise a liposome. In some embodiments, a synthetic nanocarrier may comprise a lipid bilayer. In some embodiments, a synthetic nanocarrier may comprise a lipid monolayer. In some embodiments, a synthetic nanocarrier may comprise a micelle. In some embodiments, a synthetic nanocarrier may comprise a core comprising a polymeric matrix surrounded by a lipid layer (e.g., lipid bilayer, lipid monolayer, etc.). In some embodiments, a synthetic nanocarrier may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In other embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

In some embodiments, synthetic nanocarriers may optionally comprise one or more amphiphilic entities. In some embodiments, an amphiphilic entity can promote the production of synthetic nanocarriers with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of synthetic nanocarriers to be used in accordance with the present invention.

In some embodiments, synthetic nanocarriers may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In embodiments, the inventive synthetic nanocarriers do not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

In some embodiments, synthetic nanocarriers can comprise one or more polymers. In some embodiments, the synthetic nanocarriers comprise one or more polymers that is a non-methoxy-terminated, pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated, pluronic polymers. In some embodiments, all of the polymers that make up the synthetic nanocarriers are non-methoxy-terminated, pluronic polymers. In some embodiments, the synthetic nanocarriers comprise one or more polymers that is a non-methoxy-terminated polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99%

(weight/weight) of the polymers that make up the synthetic nanocarriers are non-methoxy-terminated polymers. In some embodiments, all of the polymers that make up the synthetic nanocarriers are non-methoxy-terminated polymers. In some embodiments, the synthetic nanocarriers comprise one or more polymers that do not comprise pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers do not comprise pluronic polymer. In some embodiments, all of the polymers that make up the synthetic nanocarriers do not comprise pluronic polymer. In some embodiments, such a polymer can be surrounded by a coating layer (e.g., liposome, lipid monolayer, micelle, etc.). In some embodiments, various elements of the synthetic nanocarriers can be coupled with the polymer.

The immunosuppressants and/or antigens can be coupled to the synthetic nanocarriers by any of a number of methods. Generally, the coupling can be a result of bonding between the immunosuppressants and/or antigens and the synthetic nanocarriers. This bonding can result in the immunosuppressants and/or antigens being attached to the surface of the synthetic nanocarriers and/or contained within (encapsulated) the synthetic nanocarriers. In some embodiments, however, the immunosuppressants and/or antigens are encapsulated by the synthetic nanocarriers as a result of the structure of the synthetic nanocarriers rather than bonding to the synthetic nanocarriers. In preferable embodiments, the synthetic nanocarrier comprises a polymer as provided herein, and the immunosuppressants and/or antigens are coupled to the polymer.

When coupling occurs as a result of bonding between the immunosuppressants and/or antigens and synthetic nanocarriers, the coupling may occur via a coupling moiety. A coupling moiety can be any moiety through which an immunosuppressant and/or antigen is bonded to a synthetic nanocarrier. Such moieties include covalent bonds, such as an amide bond or ester bond, as well as separate molecules that bond (covalently or non-covalently) the immunosuppressant and/or antigen to the synthetic nanocarrier. Such molecules include linkers or polymers or a unit thereof. For example, the coupling moiety can comprise a charged polymer to which an immunosuppressant and/or antigen electrostatically binds. As another example, the coupling moiety can comprise a polymer or unit thereof to which it is covalently bonded.

In preferred embodiments, the synthetic nanocarriers comprise a polymer as provided herein. These synthetic nanocarriers can be completely polymeric or they can be a mix of polymers and other materials.

In some embodiments, the polymers of a synthetic nanocarrier associate to form a polymeric matrix. In some of these embodiments, a component, such as an immunosuppressant or antigen, can be covalently associated with one or more polymers of the polymeric matrix. In some embodiments, covalent association is mediated by a linker. In some embodiments, a component can be noncovalently associated with one or more polymers of the polymeric matrix. For example, in some embodiments, a component can be encapsulated within, surrounded by, and/or dispersed throughout a polymeric matrix. Alternatively or additionally, a component can be associated with one or more polymers of a polymeric matrix by hydrophobic interactions, charge interactions, van der Waals forces, etc. A wide variety of polymers and methods for forming polymeric matrices therefrom are known conventionally.

Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

In some embodiments, the polymer comprises a polyester, polycarbonate, polyamide, or polyether, or unit thereof. In other embodiments, the polymer comprises poly(ethylene glycol) (PEG), polypropylene glycol, poly(lactic acid), poly(glycolic acid), poly(lactic-co-glycolic acid), or a polycaprolactone, or unit thereof. In some embodiments, it is preferred that the polymer is biodegradable. Therefore, in these embodiments, it is preferred that if the polymer comprises a polyether, such as poly(ethylene glycol) or polypropylene glycol or unit thereof, the polymer comprises a block-copolymer of a polyether and a biodegradable polymer such that the polymer is biodegradable. In other embodiments, the polymer does not solely comprise a polyether or unit thereof, such as poly(ethylene glycol) or polypropylene glycol or unit thereof.

Other examples of polymers suitable for use in the present invention include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly(β-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some embodiments, polymers in accordance with the present invention include polymers which have been approved for use in humans by the U.S. Food and Drug Administration (FDA) under 21 C.F.R. §177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a synthetic nanocarrier comprising a hydrophilic polymeric matrix generates a hydrophilic environment within the synthetic nanocarrier. In some embodiments, polymers can be hydrophobic. In some embodiments, a synthetic nanocarrier comprising a hydrophobic polymeric matrix generates a hydrophobic environment within the synthetic nanocarrier. Selection of the hydrophilicity or hydrophobicity of the polymer may have an impact on the nature of materials that are incorporated (e.g. coupled) within the synthetic nanocarrier.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. In embodiments, the inventive synthetic nanocarriers may not comprise (or may exclude) cationic polymers.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that inventive synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some embodiments, synthetic nanocarriers do not comprise a polymeric component. In some embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

Compositions according to the invention comprise synthetic nanocarriers in combination with pharmaceutically acceptable excipients, such as preservatives, buffers, saline, or phosphate buffered saline. The compositions may be made using conventional pharmaceutical manufacturing and compounding techniques to arrive at useful dosage forms. In an embodiment, inventive synthetic nanocarriers are suspended in sterile saline solution for injection together with a preservative.

In embodiments, when preparing synthetic nanocarriers as carriers, methods for coupling components to the synthetic nanocarriers may be useful. If the component is a small molecule it may be of advantage to attach the component to a polymer prior to the assembly of the synthetic nanocarriers. In embodiments, it may also be an advantage to prepare the synthetic nanocarriers with surface groups that are used to couple the component to the synthetic nanocarrier through the use of these surface groups rather than attaching the component to a polymer and then using this polymer conjugate in the construction of synthetic nanocarriers.

In certain embodiments, the coupling can be a covalent linker. In embodiments, peptides according to the invention can be covalently coupled to the external surface via a 1,2,3-triazole linker formed by the 1,3-dipolar cycloaddition reaction of azido groups on the surface of the nanocarrier with antigen or immunosuppressant containing an alkyne group or by the 1,3-dipolar cycloaddition reaction of alkynes on the surface of the nanocarrier with antigens or immunosuppressants containing an azido group. Such cycloaddition reactions are preferably performed in the presence of a Cu(I) catalyst along with a suitable Cu(I)-ligand and a reducing agent to reduce Cu(II) compound to catalytic active Cu(I) compound. This Cu(I)-catalyzed azide-alkyne cycloaddition (CuAAC) can also be referred as the click reaction.

Additionally, the covalent coupling may comprise a covalent linker that comprises an amide linker, a disulfide linker, a thioether linker, a hydrazone linker, a hydrazide linker, an imine or oxime linker, an urea or thiourea linker, an amidine linker, an amine linker, and a sulfonamide linker.

An amide linker is formed via an amide bond between an amine on one component such as an antigen or immunosuppressant with the carboxylic acid group of a second component such as the nanocarrier. The amide bond in the linker can be made using any of the conventional amide bond forming reactions with suitably protected amino acids and activated carboxylic acid such N-hydroxysuccinimide-activated ester.

A disulfide linker is made via the formation of a disulfide (S—S) bond between two sulfur atoms of the form, for instance, of R1-S—S—R2. A disulfide bond can be formed by thiol exchange of a component containing thiol/mercaptan group (—SH) with another activated thiol group on a polymer or nanocarrier or a nanocarrier containing thiol/mercaptan groups with a component containing activated thiol group.

A triazole linker, specifically a 1,2,3-triazole of the form

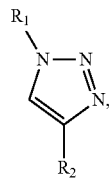

wherein R1 and R2 may be any chemical entities, is made by the 1,3-dipolar cycloaddition reaction of an azide attached to a first component such as the nanocarrier with a terminal alkyne attached to a second component such as the immunosuppressant or antigen. The 1,3-dipolar cycloaddition reaction is performed with or without a catalyst, preferably with Cu(I)-catalyst, which links the two components through a 1,2,3-triazole function. This chemistry is described in detail by Sharpless et al., Angew. Chem. Int. Ed. 41(14), 2596, (2002) and Meldal, et al, Chem. Rev., 2008, 108(8), 2952-3015 and is often referred to as a "click" reaction or CuAAC.

In embodiments, a polymer containing an azide or alkyne group, terminal to the polymer chain is prepared. This polymer is then used to prepare a synthetic nanocarrier in such a manner that a plurality of the alkyne or azide groups are positioned on the surface of that nanocarrier. Alternatively, the synthetic nanocarrier can be prepared by another route, and subsequently functionalized with alkyne or azide groups. The component is prepared with the presence of either an alkyne (if the polymer contains an azide) or an azide (if the polymer contains an alkyne) group. The component is then allowed to react with the nanocarrier via the 1,3-dipolar cycloaddition reaction with or without a catalyst which covalently couples the component to the particle through the 1,4-disubstituted 1,2,3-triazole linker.

A thioether linker is made by the formation of a sulfur-carbon (thioether) bond in the form, for instance, of R1-S—R2. Thioether can be made by either alkylation of a thiol/mercaptan (—SH) group on one component with an alkylating group such as halide or epoxide on a second component. Thioether linkers can also be formed by Michael addition of a thiol/mercaptan group on one component to an electron-deficient alkene group on a second component containing a maleimide group or vinyl sulfone group as the Michael acceptor. In another way, thioether linkers can be prepared by the radical thiol-ene reaction of a thiol/mercaptan group on one component with an alkene group on a second component.

A hydrazone linker is made by the reaction of a hydrazide group on one component with an aldehyde/ketone group on the second component.

A hydrazide linker is formed by the reaction of a hydrazine group on one component with a carboxylic acid group on the second component. Such reaction is generally performed using chemistry similar to the formation of amide bond where the carboxylic acid is activated with an activating reagent.

An imine or oxime linker is formed by the reaction of an amine or N-alkoxyamine (or aminooxy) group on one component with an aldehyde or ketone group on the second component.

An urea or thiourea linker is prepared by the reaction of an amine group on one component with an isocyanate or thioisocyanate group on the second component.

An amidine linker is prepared by the reaction of an amine group on one component with an imidoester group on the second component.

An amine linker is made by the alkylation reaction of an amine group on one component with an alkylating group such as halide, epoxide, or sulfonate ester group on the second component. Alternatively, an amine linker can also be made by reductive amination of an amine group on one component with an aldehyde or ketone group on the second component with a suitable reducing reagent such as sodium cyanoborohydride or sodium triacetoxyborohydride.

A sulfonamide linker is made by the reaction of an amine group on one component with a sulfonyl halide (such as sulfonyl chloride) group on the second component.

A sulfone linker is made by Michael addition of a nucleophile to a vinyl sulfone. Either the vinyl sulfone or the nucleophile may be on the surface of the nanocarrier or attached to a component.

The component can also be conjugated to the nanocarrier via non-covalent conjugation methods. For example, a negative charged antigen or immunosuppressant can be conjugated to a positive charged nanocarrier through electrostatic adsorption. A component containing a metal ligand can also be conjugated to a nanocarrier containing a metal complex via a metal-ligand complex.

In embodiments, the component can be attached to a polymer, for example polylactic acid-block-polyethylene glycol, prior to the assembly of the synthetic nanocarrier or the synthetic nanocarrier can be formed with reactive or activatible groups on its surface. In the latter case, the component may be prepared with a group which is compatible with the attachment chemistry that is presented by the synthetic nanocarriers' surface. In other embodiments, a peptide component can be attached to VLPs or liposomes using a suitable linker. A linker is a compound or reagent that capable of coupling two molecules together. In an embodiment, the linker can be a homobifuntional or heterobifunctional reagent as described in Hermanson 2008. For example, an VLP or liposome synthetic nanocarrier containing a carboxylic group on the surface can be treated with a homobifunctional linker, adipic dihydrazide (ADH), in the presence of EDC to form the corresponding synthetic nanocarrier with the ADH linker. The resulting ADH linked synthetic nanocarrier is then conjugated with a peptide component containing an acid group via the other end of the ADH linker on NC to produce the corresponding VLP or liposome peptide conjugate.

For detailed descriptions of available conjugation methods, see Hermanson G T "Bioconjugate Techniques", 2nd Edition Published by Academic Press, Inc., 2008. In addition to covalent attachment the component can be coupled by adsorption to a pre-formed synthetic nanocarrier or it can be coupled by encapsulation during the formation of the synthetic nanocarrier.

Any immunosuppressant as provided herein can be coupled to the synthetic nanocarrier. Immunosuppressants include, but are not limited to, statins; mTOR inhibitors, such as rapamycin or a rapamycin analog; TGF-β signaling agents; TGF-β receptor agonists; histone deacetylase (HDAC) inhibitors; corticosteroids; inhibitors of mitochondrial function, such as rotenone; P38 inhibitors; NF-κβ inhibitors; adenosine receptor agonists; prostaglandin E2 agonists; phosphodiesterase inhibitors, such as phosphodiesterase 4 inhibitor; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors and oxidized ATPs. Immunosuppressants also include IDO, vitamin D3, cyclosporine A, aryl hydrocarbon receptor inhibitors, resveratrol, azathiopurine, 6-mercaptopurine, aspirin, niflumic acid, estriol, tripolide, interleukins (e.g., IL-1, IL-10), cyclosporine A, siRNAs targeting cytokines or cytokine receptors and the like.

Examples of statins include atorvastatin (LIPITOR®, TORVAST®), cerivastatin, fluvastatin (LESCOL®, LESCOL® XL), lovastatin (MEVACOR®, ALTOCOR®, ALTOPREV®), mevastatin (COMPACTIN®), pitavastatin (LIVALO®, PIAVA®), rosuvastatin (PRAVACHOL®, SELEKTINE®, LIPOSTAT®), rosuvastatin (CRESTOR®), and simvastatin (ZOCOR®, LIPEX®).

Examples of mTOR inhibitors include rapamycin and analogs thereof (e.g., CCL-779, RAD001, AP23573, C20-methallylrapamycin (C20-Marap), C16-(S)-butylsulfonamidorapamycin (C16-BSrap), C16-(S)-3-methylindolerapamycin (C16-iRap) (Bayle et al. Chemistry & Biology 2006, 13:99-107)), AZD8055, BEZ235 (NVP-BEZ235), chrysophanic acid (chrysophanol), deforolimus (MK-8669), everolimus (RAD0001), KU-0063794, PI-103, PP242, temsirolimus, and WYE-354 (available from Selleck, Houston, Tex., USA).

Examples of TGF-β signaling agents include TGF-β ligands (e.g., activin A, GDF1, GDF11, bone morphogenic proteins, nodal, TGF-βs) and their receptors (e.g., ACVR1B, ACVR1c, ACVR2A, ACVR2B, BMPR2, BMPR1A, BMPR1B, TGFβRI, TGFβ3RII), R-SMADS/co-SMADS (e.g., SMAD1, SMAD2, SMAD3, SMAD4, SMAD5, SMAD8), and ligand inhibitors (e.g., follistatin, noggin, chordin, DAN, lefty, LTBP1, THBS1, Decorin).

Examples of inhibitors of mitochondrial function include atractyloside (dipotassium salt), bongkrekic acid (triammonium salt), carbonyl cyanide m-chlorophenylhydrazone, carboxyatractyloside (e.g., from *Atractylis gummifera*), CGP-37157, (−)-Deguelin (e.g., from *Mundulea sericea*), F16, hexokinase II VDAC binding domain peptide, oligomycin, rotenone, Ru360, SFK1, and valinomycin (e.g., from *Streptomyces fulvissimus*) (EMD4Biosciences, USA).

Examples of P38 inhibitors include SB-203580 (4-(4-Fluorophenyl)-2-(4-methylsulfinylphenyl)-5-(4-pyridyl)1H-imidazole), SB-239063 (trans-1-(4hydroxycyclohexyl)-4-(fluorophenyl)-5-(2-methoxy-pyrimidin-4-yl)imidazole), SB-220025 (5-(2-amino-4-pyrimidinyl)-4-(4-fluorophenyl)-1-(4-piperidinyl)imidazole)), and ARRY-797.

Examples of NF (e.g., NK-κβ) inhibitors include IFRD1, 2-(1,8-naphthyridin-2-yl)-Phenol, 5-aminosalicylic acid, BAY 11-7082, BAY 11-7085, CAPE (Caffeic Acid Phenethylester), diethylmaleate, IKK-2 Inhibitor IV, TMD 0354, lactacystin, MG-132 [Z-Leu-Leu-Leu-CHO], NFκB Activation Inhibitor III, NF-κB Activation Inhibitor II, JSH-23, parthenolide, Phenylarsine Oxide (PAO), PPM-18, pyrrolidinedithiocarbamic acid ammonium salt, QNZ, RO 106-9920, rocaglamide, rocaglamide AL, rocaglamide C, rocaglamide I, rocaglamide J, rocaglaol, (R)-MG-132, sodium salicylate, triptolide (PG490), wedelolactone.

Examples of adenosine receptor agonists include CGS-21680 and ATL-146e.

Examples of prostaglandin E2 agonists include E-Prostanoid 2 and E-Prostanoid 4.

Examples of phosphodiesterase inhibitors (non-selective and selective inhibitors) include caffeine, aminophylline, IBMX (3-isobutyl-1-methylxanthine), paraxanthine, pentoxifylline, theobromine, theophylline, methylated xanthines, vinpocetine, EHNA (erythro-9-(2-hydroxy-3-nonyl) adenine), anagrelide, enoximone (PERFAN™), milrinone, levosimendon, mesembrine, ibudilast, piclamilast, luteolin, drotaverine, roflumilast (DAXAS™, DALIRESP™), sildenafil (REVATION®, VIAGRA®), tadalafil (ADCIRCA®, CIALIS®), vardenafil (LEVITRA®, STAXYN®), udenafil, avanafil, icariin, 4-methylpiperazine, and pyrazolo pyrimidin-7-1.

Examples of proteasome inhibitors include bortezomib, disulfuram, epigallocatechin-3-gallate, and salinosporamide A.

Examples of kinase inhibitors include bevacizumab, BIBW 2992, cetuximab (ERBITUX®), imatinib (GLEEVEC®), trastuzumab (HERCEPTIN®), gefitinib (IRESSA®), ranibizumab (LUCENTIS®), pegaptanib, sorafenib, dasatinib, sunitinib, erlotinib, nilotinib, lapatinib, panitumumab, vandetanib, E7080, pazopanib, mubritinib.

Examples of glucocorticoids include hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (DOCA), and aldosterone.

Examples of retinoids include retinol, retinal, tretinoin (retinoic acid, RETIN-A®), isotretinoin (ACCUTANE®, AMNESTEEM®, CLARAVIS®, SOTRET®), alitretinoin (PANRETIN®), etretinate (TEGISON™) and its metabolite acitretin (SORIATANE®), tazarotene (TAZORAC®, AVAGE®, ZORAC®), bexarotene (TARGRETIN®), and adapalene (DIFFERIN®).

Examples of cytokine inhibitors include IL1ra, IL1 receptor antagonist, IGFBP, TNF-BF, uromodulin, Alpha-2-Macroglobulin, Cyclosporin A, Pentamidine, and Pentoxifylline (PENTOPAK®, PENTOXIL®, TRENTAL®).

Examples of peroxisome proliferator-activated receptor antagonists include GW9662, PPARγ antagonist III, G335, T0070907 (EMD4Biosciences, USA).

Examples of peroxisome proliferator-activated receptor agonists include pioglitazone, ciglitazone, clofibrate, GW1929, GW7647, L-165,041, LY 171883, PPARγ activator, Fmoc-Leu, troglitazone, and WY-14643 (EMD4Biosciences, USA).

Examples of histone deacetylase inhibitors include hydroxamic acids (or hydroxamates) such as trichostatin A, cyclic tetrapeptides (such as trapoxin B) and depsipeptides, benzamides, electrophilic ketones, aliphatic acid compounds such as phenylbutyrate and valproic acid, hydroxamic acids such as vorinostat (SAHA), belinostat (PXD101), LAQ824, and panobinostat (LBH589), benzamides such as entinostat (MS-275), CI994, and mocetinostat (MGCD0103), nicotinamide, derivatives of NAD, dihydrocoumarin, naphthopyranone, and 2-hydroxynaphaldehydes.

Examples of calcineurin inhibitors include cyclosporine, pimecrolimus, voclosporin, and tacrolimus.

Examples of phosphatase inhibitors include BN82002 hydrochloride, CP-91149, calyculin A, cantharidic acid, cantharidin, cypermethrin, ethyl-3,4-dephostatin, fostriecin sodium salt, MAZ51, methyl-3,4-dephostatin, NSC 95397, norcantharidin, okadaic acid ammonium salt from prorocentrum concavum, okadaic acid, okadaic acid potassium salt, okadaic acid sodium salt, phenylarsine oxide, various phosphatase inhibitor cocktails, protein phosphatase 1C, protein phosphatase 2A inhibitor protein, protein phosphatase 2A1, protein phosphatase 2A2, sodium orthovanadate.

In some embodiments, the therapeutic protein APC presentable antigens as described herein are also coupled to synthetic nanocarriers. In some embodiments, the therapeutic protein APC presentable antigens are coupled to the same or different synthetic nanocarriers as to which the immunosuppressants are coupled. In other embodiments, the therapeutic protein APC presentable antigens are not coupled to any synthetic nanocarriers. Therapeutic protein APC presentable antigens include any of the therapeutic proteins, or fragments or derivatives thereof, provided herein.

Therapeutic proteins include, but are not limited to, infusible therapeutic proteins, enzymes, enzyme cofactors, hormones, blood clotting factors, cytokines and interferons, growth factors, monoclonal antibodies, and polyclonal antibodies (e.g., that are administered to a subject as a replacement therapy), and proteins associated with Pompe's disease (e.g., alglucosidase alfa, rhGAA (e.g., Myozyme and Lumizyme (Genzyme)). Therapeutic proteins also include proteins involved in the blood coagulation cascade. Therapeutic proteins include, but are not limited to, Factor VIII, Factor VII, Factor IX, Factor V, von Willebrand Factor, von Heldebrant Factor, tissue plasminogen activator, insulin, growth hormone, erythropoietin alfa, VEGF, thrombopoietin, lysozyme, antithrombin and the like. Therapeutic proteins also include adipokines, such as leptin and adiponectin. Other examples of therapeutic proteins are as described below and elsewhere herein. Also included are fragments or derivatives of any of the therapeutic proteins provided as the antigen.

Examples of therapeutic proteins used in enzyme replacement therapy of subjects having a lysosomal storage disorder include, but are not limited to, imiglucerase for the treatment of Gaucher's disease (e.g., CEREZYME™), a-galactosidase A (a-gal A) for the treatment of Fabry disease (e.g., agalsidase beta, FABRYZYME™), acid α-glucosidase (GAA) for the treatment of Pompe disease (e.g., alglucosidase alfa, LUMIZYME™, MYOZYME™), arylsulfatase B for the treatment of Mucopolysaccharidoses (e.g., laronidase, ALDURAZYME™, idursulfase, ELAPRASE™, arylsulfatase B, NAGLAZYME™).

Examples of enzymes include oxidoreductases, transferases, hydrolases, lyases, isomerases, and ligases.

Examples of hormones include Melatonin (N-acetyl-5-methoxytryptamine), Serotonin, Thyroxine (or tetraiodothyronine) (a thyroid hormone), Triiodothyronine (a thyroid hormone), Epinephrine (or adrenaline), Norepinephrine (or noradrenaline), Dopamine (or prolactin inhibiting hormone), Antimullerian hormone (or mullerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Calcitonin, Cholecystokinin, Corticotropin-releasing hormone, Erythropoietin, Follicle-stimulating hormone, Gastrin, Ghrelin, Glucagon, Glucagon-like peptide (GLP-1), GIP, Gonadotropin-releasing hormone, Growth hormone-releasing hormone, Human chorionic gonadotropin, Human placental lactogen, Growth hormone, Inhibin, Insulin, Insulin-like growth factor (or somatomedin), Leptin, Luteinizing hormone, Melanocyte stimulating hormone, Orexin, Oxytocin, Parathyroid hormone, Prolactin, Relaxin, Secretin, Somatostatin, Thrombopoietin, Thyroid-stimulating hormone (or thyrotropin), Thyrotropin-releasing hormone, Cortisol, Aldosterone, Testosterone, Dehydroepiandrosterone, Androstenedione, Dihydrotestosterone, Estradiol, Estrone, Estriol, Progesterone, Calcitriol (1,25-dihydroxyvitamin D3), Calcidiol (25-hydroxyvitamin D3), Prostaglandins, Leukotrienes, Prostacyclin, Thromboxane, Prolactin releasing hormone, Lipotropin, Brain natriuretic peptide, Neuropeptide Y, Histamine, Endothelin, Pancreatic polypeptide, Renin, and Enkephalin.

Examples of blood and blood coagulation factors include Factor I (fibrinogen), Factor II (prothrombin), tissue factor, Factor V (proaccelerin, labile factor), Factor VII (stable factor, proconvertin), Factor VIII (antihemophilic globulin), Factor IX (Christmas factor or plasma thromboplastin component), Factor X (Stuart-Prower factor), Factor Xa, Factor XI, Factor XII (Hageman factor), Factor XIII (fibrin-stabilizing factor), von Willebrand factor, prekallikrein (Fletcher factor), high-molecular weight kininogen (HMWK) (Fitzgerald factor), fibronectin, fibrin, thrombin, antithrombin III, heparin cofactor II, protein C, protein S, protein Z, protein Z-related protease inhibitot (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant, and epoetin alfa (Epogen, Procrit).

Examples of cytokines include lymphokines, interleukins, and chemokines, type 1 cytokines, such as IFN-γ, TGF-β, and type 2 cytokines, such as IL-4, IL-10, and IL-13.

Examples of growth factors include Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha(TGF-α), Transforming growth factor beta(TGF-β), Tumour_necrosis_factor-alpha(TNF-α), Vascular endothelial growth factor (VEGF), Wnt Signaling Pathway, placental growth factor (P1GF), [(Foetal Bovine Somatotrophin)] (FBS), IL-1, IL-2, IL-3, IL-4, IL-5, IL-6, and IL-7.

Examples of monoclonal antibodies include Abagovomab, Abciximab, Adalimumab, Adecatumumab, Afelimomab, Afutuzumab, Alacizumab pegol, ALD, Alemtuzumab, Altumomab pentetate, Anatumomab mafenatox, Anrukinzumab, Anti-thymocyte globin, Apolizumab, Arcitumomab, Aselizumab, Atlizumab (tocilizumab), Atorolimumab, Bapineuzumab, Basiliximab, Bavituximab, Bectumomab, Belimumab, Benralizumab, Bertilimumab, Besilesomab, Bevacizumab, Biciromab, Bivatuzumab mertansine, Blinatumomab, Brentuximab vedotin, Briakinumab, Canakinumab, Cantuzumab mertansine, Capromab pendetide, Catumaxomab, Cedelizumab, Certolizumab pegol, Cetuximab, Citatuzumab bogatox, Cixutumumab, Clenoliximab, Clivatuzumab tetraxetan, Conatumumab, Dacetuzumab, Daclizumab, Daratumumab, Denosumab, Detumomab, Dorlimomab aritox, Dorlixizumab, Ecromeximab, Eculizumab, Edobacomab, Edrecolomab, Efalizumab, Efungumab, Elotuzumab, Elsilimomab, Enlimomab pegol, Epitumomab cituxetan, Epratuzumab, Erlizumab, Ertumaxomab, Etaracizumab, Exbivirumab, Fanolesomab, Faralimomab, Farletuzumab, Felvizumab, Fezakinumab, Figitumumab, Fontolizumab, Foravirumab, Fresolimumab, Galiximab, Gantenerumab, Gavilimomab, Gemtuzumab ozogamicin, GC1008, Girentuximab, Glembatumumab vedotin, Golimumab, Gomiliximab, Ibalizumab, Ibritumomab tiuxetan, Igovomab, Imciromab, Infliximab, Intetumumab, Inolimomab, Inotuzumab ozogamicin, Ipilimumab, Iratumumab, Keliximab, Labetuzumab, Lebrikizumab, Lemalesomab, Lerdelimumab, Lexatumumab, Libivirumab, Lintuzumab, Lorvotuzumab mertansine, Lucatumumab, Lumiliximab, Mapatumumab, Maslimomab, Matuzumab, Mepolizumab, Metelimumab, Milatuzumab, Minretumomab, Mitumomab, Morolimumab, Motavizumab, Muromonab-CD3, Nacolomab tafenatox, Naptumomab estafenatox, Natalizumab, Nebacumab, Necitumumab, Nerelimomab, Nimotuzumab, Nofetumomab merpentan, Ocrelizumab, Odulimomab, Ofatumumab, Olaratumab, Omalizumab, Oportuzumab monatox, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, Rafivirumab, Ramucirumab, Ranibizumab, Raxibacumab, Regavirumab Reslizumab, Rilotumumab, Rituximab, Robatumumab, Rontalizumab, Rovelizumab, Ruplizumab, Satumomab pendetide, Sevirumab, Sibrotuzumab, Sifalimumab, Siltuximab, Siplizumab, Solanezumab, Sonepcizumab, Sontuzumab, Stamulumab, Sulesomab, Tacatuzumab tetraxetan, Tadocizumab, Talizumab, Tanezumab, Taplitumomab paptox, Tefibazumab, Telimomab aritox, Tenatumomab, Teneliximab, Teplizumab, Ticilimumab (tremelimumab), Tigatuzumab, Tocilizumab (atlizumab), Toralizumab, Tositumomab, Trastuzumab, Tremelimumab, Tucotuzumab celmoleukin, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, and Zolimomab aritox.

Examples of infusion therapy or injectable therapeutic proteins include, for example, Tocilizumab (Roche/Actemra®), alpha-1 antitrypsin(Kamada/AAT), Hematide® (Affymax and Takeda, synthetic peptide), albinterferon alfa-2b (Novartis/Zalbin™), Rhucin® (Pharming Group, C1 inhibitor replacement therapy), tesamorelin (Theratechnologies/Egrifta, synthetic growth hormone-releasing factor), ocrelizumab (Genentech, Roche and Biogen), belimumab (GlaxoSmithKline/Benlysta®), pegloticase (Savient Pharmaceuticals/Krystexxa™), taliglucerase alfa (Protalix/Uplyso), agalsidase alfa (Shire/Replagal®), velaglucerase alfa (Shire).

Additional therapeutic proteins useful in accordance to aspects of this invention will be apparent to those of skill in the art, and the invention is not limited in this respect.

In some embodiments, a component, such as an antigen or immunosuppressant, may be isolated. Isolated refers to the element being separated from its native environment and present in sufficient quantities to permit its identification or use. This means, for example, the element may be (i) selectively produced by expression cloning or (ii) purified as by chromatography or electrophoresis. Isolated elements may be, but need not be, substantially pure. Because an isolated element may be admixed with a pharmaceutically acceptable excipient in a pharmaceutical preparation, the element may comprise only a small percentage by weight of the preparation. The element is nonetheless isolated in that it has been separated from the substances with which it may be associated in living systems, i.e., isolated from other lipids or proteins. Any of the elements provided herein may be isolated and included in the compositions in isolated form.

D. Methods of Making and Using the Inventive Compositions and Related Methods Synthetic nanocarriers may be prepared using a wide variety of methods known in the art. For example, synthetic nanocarriers can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

Various materials may be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333

(2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6): 843-853 (2010). Other methods suitable for encapsulating materials into synthetic nanocarriers may be used, including without limitation methods disclosed in U.S. Pat. No. 6,632, 671 to Unger Oct. 14, 2003.

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be coupled to the synthetic nanocarriers and/or the composition of the polymer matrix.

If particles prepared by any of the above methods have a size range outside of the desired range, particles can be sized, for example, using a sieve.

Elements (i.e., components) of the inventive synthetic nanocarriers (such as moieties of which an immunofeature surface is comprised, targeting moieties, polymeric matrices, antigens, immunosuppressants and the like) may be coupled to the overall synthetic nanocarrier, e.g., by one or more covalent bonds, or may be coupled by means of one or more linkers. Additional methods of functionalizing synthetic nanocarriers may be adapted from Published US Patent Application 2006/0002852 to Saltzman et al., Published US Patent Application 2009/0028910 to DeSimone et al., or Published International Patent Application WO/2008/127532 A1 to Murthy et al.

Alternatively or additionally, synthetic nanocarriers can be coupled to components directly or indirectly via non-covalent interactions. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Such couplings may be arranged to be on an external surface or an internal surface of an inventive synthetic nanocarrier. In embodiments, encapsulation and/or absorption is a form of coupling. In embodiments, the inventive synthetic nanocarriers can be combined with an antigen by admixing in the same vehicle or delivery system.

Populations of synthetic nanocarriers may be combined to form pharmaceutical dosage forms according to the present invention using traditional pharmaceutical mixing methods. These include liquid-liquid mixing in which two or more suspensions, each containing one or more subsets of nanocarriers, are directly combined or are brought together via one or more vessels containing diluent. As synthetic nanocarriers may also be produced or stored in a powder form, dry powder-powder mixing could be performed as could the re-suspension of two or more powders in a common media. Depending on the properties of the nanocarriers and their interaction potentials, there may be advantages conferred to one or another route of mixing.

Typical inventive compositions that comprise synthetic nanocarriers may comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

Compositions according to the invention comprise inventive synthetic nanocarriers in combination with pharmaceutically acceptable excipients. The compositions may be made using conventional pharmaceutical manufacturing and compounding techniques to arrive at useful dosage forms. Techniques suitable for use in practicing the present invention may be found in Handbook of Industrial Mixing: Science and Practice, Edited by Edward L. Paul, Victor A. Atiemo-Obeng, and Suzanne M. Kresta, 2004 John Wiley & Sons, Inc.; and Pharmaceutics: The Science of Dosage Form Design, 2nd Ed. Edited by M. E. Auten, 2001, Churchill Livingstone. In an embodiment, inventive synthetic nanocarriers are suspended in sterile saline solution for injection together with a preservative.

It is to be understood that the compositions of the invention can be made in any suitable manner, and the invention is in no way limited to compositions that can be produced using the methods described herein. Selection of an appropriate method may require attention to the properties of the particular moieties being associated.

In some embodiments, inventive synthetic nanocarriers are manufactured under sterile conditions or are terminally sterilized. This can ensure that resulting compositions are sterile and non-infectious, thus improving safety when compared to non-sterile compositions. This provides a valuable safety measure, especially when subjects receiving synthetic nanocarriers have immune defects, are suffering from infection, and/or are susceptible to infection. In some embodiments, inventive synthetic nanocarriers may be lyophilized and stored in suspension or as lyophilized powder depending on the formulation strategy for extended periods without losing activity.

The compositions of the invention can be administered by a variety of routes, including but not limited to subcutaneous, intranasal, oral, intravenous, intraperitoneal, intramuscular, transmucosal, transmuco sal, sublingual, rectal, ophthalmic, pulmonary, intradermal, transdermal, transcutaneous or intradermal or by a combination of these routes. Routes of administration also include administration by inhalation or pulmonary aerosol. Techniques for preparing aerosol delivery systems are well known to those of skill in the art (see, for example, Sciarra and Cutie, "Aerosols," in Remington's Pharmaceutical Sciences, 18th edition, 1990, pp. 1694-1712; incorporated by reference).

The therapeutic proteins provided as a cell-based therapy of the invention may be administered by parenteral, intraarterial, intranasal or intravenous administration or by injection to lymph nodes or anterior chamber of the eye or by local administration to an organ or tissue of interest. The administration may be by subcutaneous, intrathecal, intraventricular, intramuscular, intraperitoneal, intracoronary, intrapancreatic, intrahepatic or bronchial injection.

The compositions of the invention can be administered in effective amounts, such as the effective amounts described elsewhere herein. Doses of dosage forms contain varying amounts of populations of synthetic nanocarriers and/or varying amounts of immunosuppressants and/or antigens, according to the invention. The amount of synthetic nanocarriers and/or immunosuppressants and/or antigens present in the inventive dosage forms can be varied according to the nature of the antigens and/or immunosuppressants, the therapeutic benefit to be accomplished, and other such parameters. In embodiments, dose ranging studies can be conducted to establish optimal therapeutic amount of the population of synthetic nanocarriers and the amount of immunosuppressants and/or antigens to be present in the dosage form. In embodiments, the synthetic nanocarriers and/or the immunosuppressants and/or antigens are present in the dosage form in an amount effective to generate a tolerogenic immune response to the antigens upon administration to a subject. It may be possible to determine amounts of the immunosuppressants and/or antigens effective to generate a tolerogenic immune response using conventional dose ranging studies and techniques in subjects. Inventive dosage forms may be administered at a variety of frequencies. In a preferred embodiment, at least one administration of the dosage form is sufficient to generate a pharmacologically relevant response. In more preferred embodiments, at least two administrations, at least three administrations, or at least four administrations, of the dosage form are utilized to ensure a pharmacologically relevant response.

Prophylactic administration of the inventive compositions can be initiated prior to the onset of disease, disorder or condition or therapeutic administration can be initiated after a disorder, disorder or condition is established.

In some embodiments, administration of synthetic nanocarriers is undertaken e.g., prior to administration of a therapeutic protein. In exemplary embodiments, synthetic nanocarriers are administered at one or more times including, but not limited to, 30, 25, 20, 15, 14, 13, 12, 11, 10, 9, 8, 7, 6, 5, 4, 3, 2, 1, or 0 days prior to administration of a therapeutic protein. In addition or alternatively, synthetic nanocarriers can be administered to a subject following therapeutic protein administration. In exemplary embodiments, synthetic nanocarriers are administered at one or more times including, but not limited to, 1, 2, 3, 4, 5, 6, 7, 8, 9, 10, 11, 12, 13, 14, 15, 20, 25, 30, etc. days following administration of a therapeutic protein.

In some embodiments, a maintenance dose (e.g., of a synthetic nanocarrier composition provided herein) is administered to a subject after an initial administration has resulted in a tolerogenic response in the subject, for example, to maintain the tolerogenic effect achieved after the initial dose, to prevent an undesired immune reaction in the subject, or to prevent the subject becoming a subject at risk of experiencing an undesired immune response or an undesired level of an immune response. In some embodiments, the maintenance dose is the same dose as the initial dose the subject received. In some embodiments, the maintenance dose is a lower dose than the initial dose. For example, in some embodiments, the maintenance dose is about $3/4$, about $2/3$, about $1/2$, about $1/3$, about $1/4$, about $1/8$, about $1/10$, about $1/20$, about $1/25$, about $1/50$, about $1/100$, about $1/1,000$, about $1/10,000$, about $1/100,000$, or about $1/1,000,000$ (weight/weight) of the initial dose.

The compositions and methods described herein can be used to induce or enhance a tolerogenic immune response and/or to suppress, modulate, direct or redirect an undesired immune response for the purpose of immune suppression. The compositions and methods described herein can be used to for the generation of a tolerogenic immune response in a subject that has been, is being or will be administered a therapeutic protein.

EXAMPLES

Example 1

Immune Response of Synthetic Nanocarriers with Coupled Rapamycin with and without Ovalbumin Peptide (323-339)

Materials

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). Rapamycin was purchased from TSZ CHEM (185 Wilson Street, Framingham, Mass. 01702; Product Catalogue #R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). Polyvinyl alcohol (85-89% hydrolyzed) was purchased from EMD Chemicals (Product Number 1.41350.1001).

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature.

Solution 2: Rapamycin @ 50 mg/mL in methylene chloride. The solution was prepared by dissolving rapamycin in pure methylene chloride.

Solution 3: PLGA @ 100 mg/mL in methylene chloride. The solution was prepared by dissolving PLGA in pure methylene chloride.

Solution 4: Polyvinyl alcohol @ 50 mg/mL in 100 mM pH 8 phosphate buffer.

Method for Preparing Synthetic Nanocarrier Containing Rapamycin and Ovalbumin (323-339)

A primary water-in-oil emulsion was prepared first. W1/O1 was prepared by combining solution 1 (0.2 mL), solution 2 (0.2 mL), and solution 3 (1.0 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the synthetic nanocarriers to form. A portion of the synthetic nanocarriers were washed by transferring the synthetic nanocarrier suspension to a centrifuge tube and centrifuging at 21,000×g and 4° C. for one hour, removing the supernatant, and re-suspending the pellet in phosphate buffered saline. The washing procedure was repeated, and the pellet was re-suspended in phosphate buffered saline for a final synthetic nanocarrier dispersion of about 10 mg/mL.

The amounts of peptide and rapamycin in the synthetic nanocarriers were determined by HPLC analysis. The total dry-synthetic nanocarrier mass per mL of suspension was determined by a gravimetric method.

Method for Synthetic Nanocarrier Containing Rapamycin

A primary water-in-oil emulsion was prepared first. W1/O1 was prepared by combining 0.13 M hydrochloric acid solution (0.2 mL), solution 2 (0.2 mL), and solution 3 (1.0 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the synthetic nanocarriers to form. A portion of the synthetic nanocarriers were washed by transferring the synthetic nanocarrier suspension to a centrifuge tube and centrifuging at 21,000×g and 4° C. for one hour, removing the supernatant, and re-suspending the pellet in phosphate buffered saline. The washing procedure was repeated, and the pellet was re-suspended in phosphate buffered saline for a final synthetic nanocarrier dispersion of about 10 mg/mL.

The amount of rapamycin in the synthetic nanocarrier was determined by HPLC analysis. The total dry-synthetic nanocarrier mass per mL of suspension was determined by a gravimetric method.

Method for Measuring Rapamycin Load

Approximately 3 mg of synthetic nanocarriers were collected and centrifuged to separate supernatant from synthetic nanocarrier pellet. Acetonitrile was added to the pellet, and the sample was sonicated and centrifuged to remove any insoluble material. The supernatant and pellet were injected on RP-HPLC and absorbance was read at 278 nm. The μg found in the pellet were used to calculate % entrapped (load), μg in supernatant and pellet were used to calculate total μg recovered.

Method for Measuring Ovalbumin (323-339) Load

Approximately 3 mg of synthetic nanocarriers were collected and centrifuged to separate supernatant from synthetic nanocarrier pellet. Trifluoroethanol was added to the pellet and the sample was sonicated to dissolve the polymer, 0.2% trifluoroacetic acid was added and sample was sonicated and then centrifuged to remove any insoluble material. The supernatant and pellet were injected on RP-HPLC and absorbance was read at 215 nm. The μg found in the pellet were used to calculate % entrapped (load), μg in supernatant and pellet were used to calculate total μg recovered.

Antigen-Specific Tolerogenic Dendritic Cells (Tdc) Activity on Treg Cell Development The assay included the use of OTII mice which have a transgenic T-cell receptor specific for an immune-dominant ovalbumin (323-339). In order to create antigen-specific tDCs, CD11c+ splenocytes were isolated, and the ovalbumin (323-339) peptide added in vitro at 1 μg/ml or no antigen. Soluble or nanocarrier-encapsulated rapamycin was then added to the DCs for 2 hours which were then washed extensively to remove free rapamycin from the culture. Purified responder CD4+CD25-cells were isolated from DT11 mice and added to tDC at a 10:1 T to DC ratio. The mixture of tDC and OTII T-cells were then cultured for 4-5 days, and the frequency of Treg cells (CD4+CD25highFoxP3+) were analyzed by flow cytometry as shown in FIG. 1. Regions were selected based on isotype controls.

Example 2

Mesoporous Silica Nanoparticles with Coupled Ibuprofen (Prophetic)

Mesoporous SiO2 nanoparticle cores are created through a sol-gel process. Hexadecyltrimethyl-ammonium bromide (CTAB) (0.5 g) is dissolved in deionized water (500 mL), and then 2 M aqueous NaOH solution (3.5 mL) is added to the CTAB solution. The solution is stirred for 30 min, and then Tetraethoxysilane (TEOS) (2.5 mL) is added to the solution. The resulting gel is stirred for 3 h at a temperature of 80° C. The white precipitate which forms is captured by filtration, followed by washing with deionized water and drying at room temperature. The remaining surfactant is then extracted from the particles by suspension in an ethanolic solution of HCl overnight. The particles are washed with ethanol, centrifuged, and redispersed under ultrasonication. This wash procedure is repeated two additional times.

The SiO2 nanoparticles are then functionalized with amino groups using (3-aminopropyl)-triethoxysilane (APTMS). To do this, the particles are suspended in ethanol (30 mL), and APTMS (50 μL) is added to the suspension. The suspension is allowed to stand at room temperature for 2 h and then is boiled for 4 h, keeping the volume constant by periodically adding ethanol. Remaining reactants are removed by five cycles of washing by centrifugation and redispersing in pure ethanol.

In a separate reaction, 1-4 nm diameter gold seeds are created. All water used in this reaction is first deionized and then distilled from glass. Water (45.5 mL) is added to a 100 mL round-bottom flask. While stirring, 0.2 M aqueous NaOH (1.5 mL) is added, followed by a 1% aqueous solution of tetrakis(hydroxymethyl)phosphonium chloride (THPC) (1.0 mL). Two minutes after the addition of THPC solution, a 10 mg/mL aqueous solution of chloroauric acid (2 mL), which has been aged at least 15 min, is added. The gold seeds are purified through dialysis against water.

To form the core-shell nanocarriers, the amino-functionalized SiO2 nanoparticles formed above are first mixed with the gold seeds for 2 h at room temperature. The gold-decorated SiO2 particles are collected through centrifugation and mixed with an aqueous solution of chloroauric acid and potassium bicarbonate to form the gold shell. The particles are then washed by centrifugation and redispersed in water. Ibuprofen is loaded by suspending the particles in a solution of sodium ibuprofen (1 mg/L) for 72 h. Free ibuprofen is then washed from the particles by centrifugation and redispersing in water.

Example 3

Liposomes Containing Cyclosporine A (Prophetic)

The liposomes are formed using thin film hydration. 1,2-Dipalmitoyl-sn-glycero-3-phosphocholine (DPPC) (32 μmol), cholesterol (32 μmol), and cyclosporin A (6.4 μmol) are dissolved in pure chloroform (3 mL). This lipid solution is added to a 50 mL round-bottom flask, and the solvent is evaporated on a rotary evaporator at a temperature of 60° C. The flask is then flushed with nitrogen gas to remove remaining solvent. Phosphate buffered saline (2 mL) and five glass beads are added to the flask, and the lipid film is hydrated by shaking at 60° C. for 1 h to form a suspension. The suspension is transferred to a small pressure tube and sonicated at 60° C. for four cycles of 30 s pulses with a 30 s delay between each pulse. The suspension is then left undisturbed at room temperature for 2 h to allow for complete hydration. The liposomes are washed by centrifugation followed by resuspension in fresh phosphate buffered saline.

Example 4

Polymeric Nanocarrier Containing Polymer-Rapamycin Conjugate (Prophetic)

Preparation of PLGA-rapamycin conjugate:

PLGA polymer with acid end group (7525 DLG1A, acid number 0.46 mmol/g, Lakeshore Biomaterials; 5 g, 2.3 mmol, 1.0 eq) is dissolved in 30 mL of dichloromethane (DCM). N,N-Dicyclohexylcarbodimide (1.2 eq, 2.8 mmol, 0.57 g) is added followed by rapamycin (1.0 eq, 2.3 mmol, 2.1 g) and 4-dimethylaminopyridine (DMAP) (2.0 eq, 4.6 mmol, 0.56 g). The mixture is stirred at rt for 2 days. The mixture is then filtered to remove insoluble dicyclohexylurea. The filtrate is concentrated to ca. 10 mL in volume and added to 100 mL of isopropyl alcohol (IPA) to precipitate out the PLGA-rapamycin conjugate. The IPA layer is removed and the polymer is then washed with 50 mL of IPA and 50 mL of methyl t-butyl ether (MTBE). The polymer is then dried under vacuum at 35 C for 2 days to give PLGA-rapamycin as a white solid (ca. 6.5 g).

Preparation of nanocarrier containing PLGA-rapamycin conjugate and ovalbumin peptide (323-339):

Nanocarrier containing PLGA-rapamycin is prepared according to the procedure described in Example 1 as follows:

Solutions for nanocarrier formation are prepared as follows:

Solution 1: Ovalbumin peptide 323-339 @ 20 mg/mL in dilute hydrochloric acid aqueous solution. The solution is prepared by dissolving ovalbumin peptide in 0.13 M hydrochloric acid solution at room temperature. Solution 2: PLGA-rapamycin @ 100 mg/mL in methylene chloride. The solution is prepared by dissolving PLGA-rapamycin in pure methylene chloride. Solution 3: PLA-PEG @ 100 mg/mL in methylene chloride. The solution is prepared by dissolving PLA-PEG in pure methylene chloride. Solution 4: Polyvinyl alcohol @ 50 mg/mL in 100 mM pH 8 phosphate buffer.

A primary water-in-oil emulsion is prepared first. W1/O1 is prepared by combining solution 1 (0.2 mL), solution 2 (0.75 mL), and solution 3 (0.25 mL) in a small pressure tube and sonicating at 50% amplitude for 40 seconds using a Branson Digital Sonifier 250. A secondary emulsion (W1/O1/W2) is then prepared by combining solution 4 (3.0 mL) with the primary W1/O1 emulsion, vortexing for 10 s, and sonicating at 30% amplitude for 60 seconds using the Branson Digital Sonifier 250. The W1/O1/W2 emulsion is added to a beaker containing 70 mM pH 8 phosphate buffer solution (30 mL) and stirred at room temperature for 2 hours to allow the methylene chloride to evaporate and for the nanocarriers to form. A portion of the nanocarriers is washed by transferring the nanocarrier suspension to a centrifuge tube and centrifuging at 75,600×g and 4° C. for 35 min, removing the supernatant, and re-suspending the pellet in phosphate buffered saline. The washing procedure is repeated, and the pellet is re-suspended in phosphate buffered saline for a final nanocarrier dispersion of about 10 mg/mL.

Example 5

Preparation of Gold Nanocarriers (AuNCs) Containing Rapamycin (Prophetic)

Preparation of HS-PEG-Rapamycin:

A solution of PEG acid disulfide (1.0 eq), rapamycin (2.0-2.5 eq), DCC (2.5 eq) and DMAP (3.0 eq) in dry DMF is stirred at rt overnight. The insoluble dicyclohexylurea is removed by filtration and the filtrate is added to isopropyl alcohol (IPA) to precipitate out the PEG-disulfide-di-rapamycin ester and washed with IPA and dried. The polymer is then treated with tris(2-carboxyethyl)phosphine hydrochloride in DMF to reduce the PEG disulfide to thiol PEG rapamycin ester (HS-PEG-rapamycin). The resulting polymer is recovered by precipitation from IPA and dried as previously described and analyzed by H NMR and GPC.

Formation of Gold NCs (AuNCs):

An aq. solution of 500 mL of 1 mM HAuC14 is heated to reflux for 10 min with vigorous stirring in a 1 L round-bottom flask equipped with a condenser. A solution of 50 mL of 40 mM of trisodium citrate is then rapidly added to the stirring solution. The resulting deep wine red solution is kept at reflux for 25-30 min and the heat is withdrawn and the solution is cooled to room temperature. The solution is then filtered through a 0.8 µm membrane filter to give the AuNCs solution. The AuNCs are characterized using visible spectroscopy and transmission electron microscopy. The AuNCs are ca. 20 nm diameter capped by citrate with peak absorption at 520 nm.

AuNCs conjugate with HS-PEG-rapamycin:

A solution of 150 µl of HS-PEG-rapamycin (10 µM in 10 mM pH 9.0 carbonate buffer) is added to 1 mL of 20 nm diameter citrate-capped gold nanocarriers (1.16 nM) to produce a molar ratio of thiol to gold of 2500:1. The mixture is stirred at room temperature under argon for 1 hour to allow complete exchange of thiol with citrate on the gold nanocarriers. The AuNCs with PEG-rapamycin on the surface is then purified by centrifuge at 12,000 g for 30 minutes. The supernatant is decanted and the pellet containing AuNC—S-PEG-rapamycin is then pellet washed with 1×PBS buffer. The purified Gold-PEG-rapamycin nanocarriers are then resuspend in suitable buffer for further analysis and bioassays.

Example 6

Mesoporous Silica-gold Core-shell Nanocarriers Containing Ovalbumin (Prophetic)

Mesoporous SiO2 nanoparticle cores are created through a sol-gel process. Hexadecyltrimethyl-ammonium bromide (CTAB) (0.5 g) is dissolved in deionized water (500 mL), and then 2 M aqueous NaOH solution (3.5 mL) is added to the CTAB solution. The solution is stirred for 30 min, and then Tetraethoxysilane (TEOS) (2.5 mL) is added to the solution. The resulting gel is stirred for 3 h at a temperature of 80° C. The white precipitate which forms is captured by filtration, followed by washing with deionized water and drying at room temperature. The remaining surfactant is then extracted from the particles by suspension in an ethanolic solution of HCl overnight. The particles are washed with ethanol, centrifuged, and redispersed under ultrasonication. This wash procedure is repeated two additional times.

The SiO2 nanoparticles are then functionalized with amino groups using (3-aminopropyl)-triethoxysilane (APTMS). To do this, the particles are suspended in ethanol (30 mL), and APTMS (50 µL) is added to the suspension. The suspension is allowed to stand at room temperature for 2 h and then is boiled for 4 h, keeping the volume constant by periodically adding ethanol. Remaining reactants are removed by five cycles of washing by centrifugation and redispersing in pure ethanol.

In a separate reaction, 1-4 nm diameter gold seeds are created. All water used in this reaction is first deionized and then distilled from glass. Water (45.5 mL) is added to a 100 mL round-bottom flask. While stirring, 0.2 M aqueous NaOH (1.5 mL) is added, followed by a 1% aqueous solution of tetrakis(hydroxymethyl)phosphonium chloride (THPC) (1.0 mL). Two minutes after the addition of THPC solution, a 10 mg/mL aqueous solution of chloroauric acid (2 mL), which has been aged at least 15 min, is added. The gold seeds are purified through dialysis against water.

To form the core-shell nanocarriers, the amino-functionalized SiO2 nanoparticles formed above are first mixed with the gold seeds for 2 h at room temperature. The gold-decorated SiO2 particles are collected through centrifugation and mixed with an aqueous solution of chloroauric acid and potassium bicarbonate to form the gold shell. The particles are then washed by centrifugation and redispersed in water. Thiolated Ovalbumin (made by treating Ovalbumin with 2-iminothiolane hydrochloride) is loaded by suspending the particles in a solution of thiolated Ovalbumin (1 mg/L) for 72 h. The particles is then pellet washed with 1×PBS (pH 7.4) to remove free protein. The resulting silica-gold core-shell nanocarriers containing Ovalbumin are then re-suspended in 1×PBS for further analysis and assays.

Example 7

Liposomes Containing Rapamycin and Ovalbumin (Prophetic)

The liposomes are formed by thin film hydration. 1,2-Dipalmitoyl-sn-glycero-3-phosphocholine (DPPC) (32 µmol), cholesterol (32 µmol), and rapamycin (6.4 µmol) are dissolved in pure chloroform (3 mL). This lipid solution is added to a 10 mL glass tube and the solvent is removed under nitrogen gas stream and desiccated for 6 hr. under vacuum. Multilamellar vesicles are obtained by hydration of the film with 2.0 ml of 25 mM MOPS buffer pH 8.5, containing excess amount of Ovalbumin. The tube is vortexed until the lipid film is peeled of from the tube surface. To break the multilamellar vesicles into monolamellar, ten cycles of freezing (liquid nitrogen) and thawing (30° C. water bath) are applied. The sample is then diluted to 1 ml in 25 mM MOPS buffer pH 8.5. Size of the resulting liposome is homogenized by extrusion by passing the sample 10 fold through a 200 nm pore polycarbonate filters. The resulting liposomes are then used for further analysis and bioassays.

Example 8

Polymeric Nanocarriers Composed of Modified Polyamino Acid with Surface Conjugated Ovalbumin (Prophetic)

Step-1. Preparation of Poly(γ-glutamic acid) (7-PGA) modified with L-phenylalanine ethyl ester (L-PAE): 4.7 unit mmol of 7-PGA (Mn=300 kD) is dissolved in 0.3 N—NaHCO₃ aqueous solution (50 mL). L-PAE (4.7 mmol) and EDC.HCl (4.7 mmol) are added to the solution and stirred for 30 min at 4 C. The solution is then maintained at room temperature with stirring for 24 h. Low-molecular-weight chemicals are removed by dialysis using dialysis membrane with MWCO 50 kD. The resulting γ-PGA-graft-L-PAE is obtained by freeze-drying.

Step-2. Preparation of nanoparticles from γ-PGA-graft-L-PAE polymer: Nanoparticles composed of γ-PGA-graft-L-PAE are prepared by a precipitation and dialysis method. γ-PGA-graft-L-PAE (20 mg) was dissolved in 2 ml of DMSO followed by addition of 2 mL of water to form a translucent solution. The solution is then dialyzed against distilled water using cellulose membrane tubing (50,000 MWCO) to form the nanoparticles and to remove the organic solvents for 72 h at room temperature. The distilled water is exchanged at intervals of 12 h. The resulting nanoparticle solution (10 mg/mL in water) is then used for antigen conjugation.

Step-3. Ovalbumin conjugation to γ-PGA nanoparticles: Surface carboxylic acid groups of the γ-PGA nanoparticles (10 mg/ml) are first activated by EDC and NHS (10 mg/mL each in phosphate buffer, pH 5.8) for 2 h at ambient temperature. After pellet washing to remove excess EDC/NHS, the activated nanoparticles are mixed with 1 mL of Ovalbumin (10 mg/ml) in phosphate-buffered saline (PBS, pH 7.4) and the mixture is incubated at 4-8 C for 24 h. The resulting Ovalbumin conjugated γ-PGA nanoparticles are washed twice with PBS and resuspended at 5 mg/mL in PBS for further analysis and bioassays.

Example 9

Erythropoietin (EPO)-Encapsulated γ-PGA Nanoparticles (Prophetic)

To prepare the EPO-encapsulated 7-PGA nanoparticles, 0.25-4 mg of EPO is dissolved in 1 mL of PBS (pH 7.4) and 1 mL of the γ-PGA-graft-L-PAE (10 mg/mL in DMSO) is added to the EPO solution. The resulting solution is centrifuged at 14,000×g for 15 min and repeatedly rinsed with PBS. The resulting EPO-encapsulated γ-PGA nanoparticles are then resuspended in PBS (5 mg/mL) for further analysis and bioassay.

Example 10

Preparation of Gold Nanocarriers (AuNCs) Containing Ovalbumin (Prophetic)

Step-1. Formation of Gold NCs (AuNCs): An aq. solution of 500 mL of 1 mM HAuC14 is heated to reflux for 10 min with vigorous stirring in a 1 L round-bottom flask equipped with a condenser. A solution of 50 mL of 40 mM of trisodium citrate is then rapidly added to the stirring solution. The resulting deep wine red solution is kept at reflux for 25-30 min and the heat is withdrawn and the solution is cooled to room temperature. The solution is then filtered through a 0.8 µm membrane filter to give the AuNCs solution. The AuNCs are characterized using visible spectroscopy and transmission electron microscopy. The AuNCs are ca. 20 nm diameter capped by citrate with peak absorption at 520 nm.

Step-2. Conjugation of Ovalbumin to AuNCs: A solution of 150 µl of thiolated Ovalbumin (10 µM in 10 mM pH 9.0 carbonate buffer) is added to 1 mL of 20 nm diameter citrate-capped gold nanocarriers (1.16 nM) to produce a molar ratio of thiol to gold of 2500:1. The mixture is stirred at room temperature under argon for 1 hour to allow complete exchange of thiol with citrate on the gold nanocarriers. The AuNCs with Ovalbumin on the surface is then purified by centrifuge at 12,000 g for 30 minutes. The supernatant is decanted and the pellet containing AuNC-Ovalbumin is then pellet washed with 1×PBS buffer. The purified Gold-Ovalbumin nanocarriers are then resuspend in suitable buffer for further analysis and bioassays.

Example 11

Evaluating Tolerogenic Immune Response to Epoietin Alpha In Vivo (Prophetic)

Balb/c mice are immunized with epoietin alpha in incomplete Freunds adjuvant to induce CD4+ T-cell proliferation, the level of which is assessed. Subsequently, a composition of the invention comprising MHC Class II-restricted epitopes of epoietin alpha and an immunosuppressant is administered subcutaneously in a dose-dependent manner. The same mice are then again exposed to the epoietin alpha, and the level of CD4+ T cell proliferation is again assessed. Changes in the CD4+ T cell population are then monitored with a reduction in CD4+ T cell proliferation upon subsequent challenge with epoietin alpha indicating a tolerogenic immune response.

Example 12

Evaluating Tolerogenic Immune Responses with Synthetic Nanocarriers Comprising Immunosuppressant and APC Presentable Antigen In Vivo Materials and Methods of Synthetic Nanocarrier Production Nanocarrier 1

Rapamycin was purchased from TSZ CHEM (185 Wilson Street, Framingham, Mass. 01702; Product Catalogue #R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Rapamycin @ 50 mg/mL in methylene chloride. The solution was prepared by dissolving rapamycin in pure methylene chloride.

Solution 2: PLGA @ 100 mg/mL in methylene chloride. The solution was prepared by dissolving PLGA in pure methylene chloride.

Solution 3: PLA-PEG @ 100 mg/mL in methylene chloride. The solution was prepared by dissolving PLA-PEG in pure methylene chloride.

Solution 4: Polyvinyl alcohol @ 50 mg/mL in 100 mM pH 8 phosphate buffer.

An oil-in-water emulsion was used to prepare the nanocarriers. The O/W emulsion was prepared by combining solution 1 (0.2 mL), solution 2 (0.75 mL), solution 3 (0.25 mL), and solution 4 (3 mL) in a small pressure tube and sonicating at 30% amplitude for 60 seconds using a Branson Digital Sonifier 250. The O/W emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers was washed by transferring the nanocarrier suspension to a centrifuge tube and centrifuging at 21,000×g and 4° C. for 45 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of rapamycin in the nanocarrier was determined by HPLC analysis. The total dry-nanocarrier mass per mL of suspension was determined by a gravimetric method.

| Nanocarrier ID | Effective Diameter (nm) | Rapamycin Content (% w/w) |
|---|---|---|
| Nanocarrier 1 | 215 | 9.5 |

Nanocarrier 2

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature.

Solution 2: PLGA @ 100 mg/mL in methylene chloride. The solution was prepared by dissolving PLGA in pure methylene chloride.

Solution 3: PLA-PEG @ 100 mg/mL in methylene chloride. The solution was prepared by dissolving PLA-PEG in pure methylene chloride.

Solution 4: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.75 mL), and solution 3 (0.25 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of peptide in the nanocarrier was determined by HPLC analysis. The total dry-nanocarrier mass per mL of suspension was determined by a gravimetric method.

| Nanocarrier ID | Effective Diameter (nm) | Peptide Content (% w/w) |
|---|---|---|
| Nanocarrier 2 | 234 | 2.1 |

Nanocarrier 3

Simvastatin was purchased from LKT Laboratories, Inc. (2233 University Avenue West, St. Paul, Minn. 55114; Product Catalogue #S3449). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Simvastatin @ 50 mg/mL in methylene chloride. The solution was prepared by dissolving simvastatin in pure methylene chloride.

Solution 2: PLGA @ 100 mg/mL in methylene chloride. The solution was prepared by dissolving PLGA in pure methylene chloride.

Solution 3: PLA-PEG @ 100 mg/mL in methylene chloride. The solution was prepared by dissolving PLA-PEG in pure methylene chloride.

Solution 4: Polyvinyl alcohol @ 50 mg/mL in 100 mM pH 8 phosphate buffer.

An oil-in-water emulsion was used to prepare the nanocarriers. The O/W emulsion was prepared by combining solution 1 (0.15 mL), solution 2 (0.75 mL), solution 3 (0.25 mL), and solution 4 (3 mL) in a small pressure tube and sonicating at 30% amplitude for 60 seconds using a Branson Digital Sonifier 250. The O/W emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers was washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of simvastatin in the nanocarrier was determined by HPLC analysis. The total dry-nanocarrier mass per mL of suspension was determined by a gravimetric method.

| Nanocarrier ID | Effective Diameter (nm) | Simvastatin Content (% w/w) |
|---|---|---|
| Nanocarrier 3 | 196 | 8.0 |

Nanocarrier 4

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). Rapamycin was purchased from TSZ CHEM (185 Wilson Street, Framingham, Mass. 01702; Product Catalogue #R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature.

Solution 2: Rapamycin @ 50 mg/mL in methylene chloride. The solution was prepared by dissolving rapamycin in pure methylene chloride.

Solution 3: PLGA @ 100 mg/mL in methylene chloride. The solution was prepared by dissolving PLGA in pure methylene chloride.

Solution 4: PLA-PEG @ 100 mg/mL in methylene chloride. The solution was prepared by dissolving PLA-PEG in pure methylene chloride.

Solution 5: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.2 mL), solution 3 (0.75 mL), and solution 4 (0.25 mL) in a small pressure tube and sonicating at 50% amplitude for 40 seconds using a Branson Digital Sonifier 250. A secondary emulsion (W1/O1/W2) was then prepared by combining solution 5 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 21,000×g and 4° C. for 45 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amounts of peptide and rapamycin in the nanocarrier were determined by HPLC analysis. The total dry-nanocarrier mass per mL of suspension was determined by a gravimetric method.

| Nanocarrier ID | Effective Diameter (nm) | Rapamycin Content (% w/w) | Peptide Content (% w/w) |
|---|---|---|---|
| 4 | 227 | 9.0 | 2.5 |

Nanocarrier 5

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). Simvastatin was purchased from LKT Laboratories, Inc. (2233 University Avenue West, St. Paul, Minn. 55114; Product Catalogue #S3449). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature.

Solution 2: Simvastatin @ 50 mg/mL in methylene chloride. The solution was prepared by dissolving simvastatin in pure methylene chloride.

Solution 3: PLGA @ 100 mg/mL in methylene chloride. The solution was prepared by dissolving PLGA in pure methylene chloride.

Solution 4: PLA-PEG @ 100 mg/mL in methylene chloride. The solution was prepared by dissolving PLA-PEG in pure methylene chloride.

Solution 5: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.15 mL), solution 3 (0.75 mL), and solution 4 (0.25 mL) in a small pressure tube and sonicating at 50% amplitude for 40 seconds using a Branson Digital Sonifier 250. A secondary emulsion (W1/O1/W2) was then prepared by combining solution 5 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amounts of peptide and simvastatin in the nanocarrier were determined by HPLC analysis. The total dry-nanocarrier mass per mL of suspension was determined by a gravimetric method.

| Nanocarrier ID | Effective Diameter (nm) | Simvastatin Content (% w/w) | Peptide Content (% w/w) |
|---|---|---|---|
| Nanocarrier 5 | 226 | 2.7 | 1.9 |

In Vivo Administration 1

Spleens from B6.Cg-Tg(TcraTcrb)425Cbna (DTII) and C57BL/6 (B6) mice were harvested, mechanically dissociated and filtered separately through a 70 μM sieve to yield a single-cell suspension. Purified CD4$^+$CD25-cells were then extracted in a 2-step process. Using a Miltenyi Biotec AutoMACS magnetic cell sorter spleen cells were first labeled with CD4$^+$ T-cell isolation kit II and the unlabeled fraction was depleted of CD25$^+$ cells with CD25 depletion kit. The purified B6 cells were stained with an intracellular dye, Carboxyfluorescein Succinimidyl Ester (CFSE), before being admixed at equal concentrations with the purified OTII cells. They were then injected intravenously (i.v.) into B6.5JL-Ptprc$^a$/BoyAi (CD45.1) recipient mice.

The next day the recipient CD45.1 mice were treated with targeted tolerogenic synthetic vaccine particles (t$^2$SVP). They were loaded with combinations of ovalbumin peptide (323-339) (OVA$^{323\text{-}339}$), Rapamycin (Rapa) and/or Simvastatin (Simva) and were administered subcutaneously (s.c.).

The injection constitutes a tolerogenic treatment and was followed by 4 more injections each spaced 2 weeks apart. After the treatment schedule was completed the recipient CD45.1 animals were killed and their spleens and popliteal lymph nodes were harvested, mechanically dissociated and filtered separately through a 70 μM sieve to yield a single-cell suspension. The spleen cells were depleted of red blood cells (RBCs) by incubation with RBC lysis buffer (Stem Cell Technologies) and cell counts were performed on both the spleens and lymph nodes.

Spleen or lymph node cells were cultured in CM (complete media) supplemented with 10 U/ml IL-2, restimulated with OPII at 0.3×10$^6$ cells/well in 96-well round bottom (RB) plates and incubated at 37° C., 5% CO$_2$. Cells were split at Day 2 and harvested on Day 5. Supernatants were collected and frozen while cells were stained for phenotypic analysis by flow cytometry. The cells were analyzed on a Becton Dickinson FacsCanto flow cytometer.

In Vivo Administration 2

Spleens from B6.Cg-Tg(TcraTcrb)425Cbna (DTII) and C57BL/6 (B6) mice were harvested, mechanically dissociated and filtered separately through a 70 μM sieve to yield a single-cell suspension. Purified CD4$^+$CD25-cells were then extracted in a 2-step process using a Miltenyi Biotec AutoMACS magnetic cell sorter. Spleen cells were labeled using Miltenyi's CD4$^+$ T-cell isolation kit II. The unlabeled CD4+ T-cell fraction was then depleted of CD25$^+$ cells with CD25 depletion kit. The purified CD4 cells from B6 mice were then stained with an intracellular dye, Carboxyfluorescein Succinimidyl Ester (CFSE), before being admixed at equal concentrations with the purified OT11 cells. They were then injected intravenously (i.v.) into B6.5JL-Ptprc$^a$/BoyAi (CD45.1) recipient mice.

The next day the recipient CD45.1 mice were treated with targeted tolerogenic synthetic vaccine particles. They comprised combinations of ovalbumin peptide (323-339) (OVA$^{323\text{-}339}$), Rapamycin (Rapa) and Simvastatin (Simva) and were administered subcutaneously (s.c.) or intravenously (i.v.).

After the treatment schedule was completed the recipient CD45.1 animals were killed and their spleens and popliteal lymph nodes were harvested, mechanically dissociated and filtered separately through a 70 μM sieve to yield a single-cell suspension. The spleen cells were depleted of red blood cells (RBCs) by incorporation with RBC lysis buffer (Stem Cell Technologies) and cell counts were performed on both the spleens and lymph nodes.

Spleen or lymph node cells were cultured in CM supplemented with 10 U/ml IL-2, restimulated with 1 μM OPII at 0.3×10$^6$ cells/well in 96-well round bottom (RB) plates and incubated at 37° C., 5% CO$_2$. Cells were split at Day 2 and harvested on Day 5. Supernatants were collected and frozen while cells were stained for phenotypic analysis by flow cytometry. The cells were analyzed on a Becton Dickinson FacsCanto flow cytometer.

Results

Figure 2:
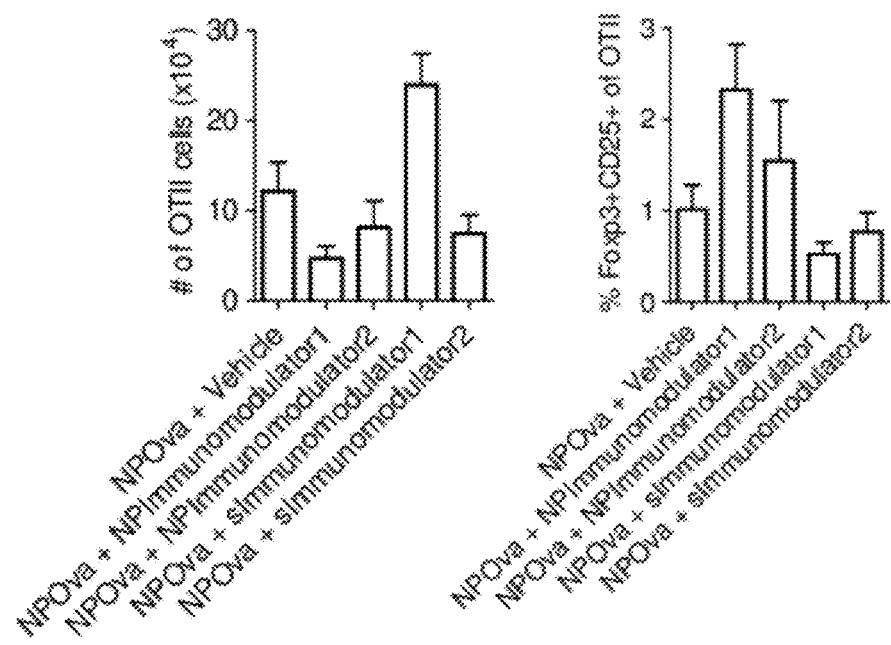
FIG. 2 shows an effect on the number of antigen-specific effector T cells with synthetic nanocarriers of the invention comprising immunosuppressant (rapamycin or simvastatin) (after a single injection).
Figure 3:
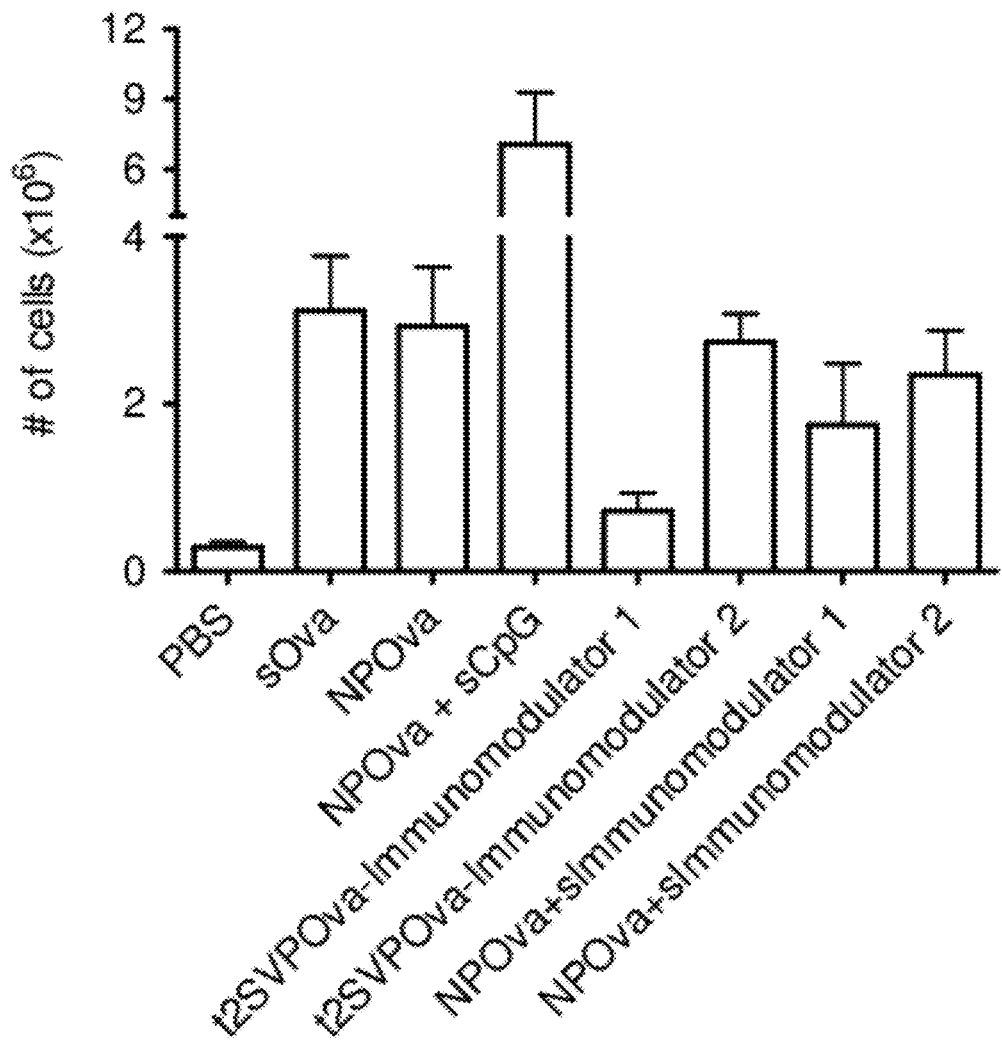
FIG. 3 shows a decrease in the number of popliteal lymph node cells with synthetic nanocarriers of the invention comprising immunosuppressant (rapamycin or simvastatin) (after multiple injections).

The results are shown in FIGS. 2 and 3 (Immunomodulator 1: rapamycin; immunomodulator 2: simvastatin). The figures shows in vivo effects and demonstrates that antigen-specific expansion of effector immune cells is reduced with synthetic nanocarriers comprising antigen and immunosuppressants as compared to antigen alone or synthetic nanocarriers comprising antigen with and without an immunostimulatory molecule.

Example 13

Tolerogenic Immune Responses with Synthetic Nanocarriers

Materials and Methods

Nanocarrier 1

Ovalbumin protein was purchased from Worthington Biochemical Corporation (730 Vassar Avenue, Lakewood, N.J. 08701; Product Code 3048). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). Polyvinyl alcohol (85-89% hydrolyzed) was purchased from EMD Chemicals (Product Number 1.41350.1001). PLA-PEG block co-polymer with a PEG block of approximately 5,000 Da and PLA block of approximately 20,000 Da was synthesized. Sodium cholate hydrate was purchased from Sigma-Aldrich Corp. (3050 Spruce Street, St. Louis, Mo. 63103; Product Code C6445).

Solutions were prepared as follows:

Solution 1: Ovalbumin @ 50 mg/mL in phosphate buffered saline solution. The solution was prepared by dissolving ovalbumin in phosphate buffered saline solution at room temperature. Solution 2: PLGA @ 100 mg/mL in methylene chloride. The solution was prepared by dissolving PLGA in pure methylene chloride. Solution 3: PLA-PEG @ 100 mg/mL in methylene chloride. The solution was prepared by dissolving PLA-PEG in pure methylene chloride. Solution 4: Polyvinyl alcohol @ 50 mg/mL and sodium cholate hydrate @ 10 mg/mL in 100 mM pH 8 phosphate buffer.

A primary water-in-oil emulsion was prepared first. W1/O1 was prepared by combining solution 1 (0.2 mL), solution 2 (0.75 mL), and solution 3 (0.25 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250. The W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of protein in the nanocarrier was determined by an o-phthalaldehyde fluorometric assay. The total dry-nanocarrier mass per mL of suspension was determined by a gravimetric method.

| Nanocarrier ID | Effective Diameter (nm) | Protein Content (% w/w) |
| --- | --- | --- |
| 1 | 191 | 10.1 |

Nanocarrier 2

Ovalbumin protein was purchased from Worthington Biochemical Corporation (730 Vassar Avenue, Lakewood, N.J. 08701; Product Code 3048). Rapamycin was purchased from TSZ CHEM (185 Wilson Street, Framingham, Mass. 01702; Product Catalogue #R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001). Sodium cholate hydrate was purchased from Sigma-Aldrich Corp. (3050 Spruce Street, St. Louis, Mo. 63103; Product Code C6445).

Solutions were prepared as follows:

Solution 1: Ovalbumin @ 50 mg/mL in phosphate buffered saline solution. The solution was prepared by dissolving ovalbumin in phosphate buffered saline solution at room temperature. Solution 2: Rapamycin @ 50 mg/mL in methylene chloride. The solution was prepared by dissolving rapamycin in pure methylene chloride. Solution 3: PLGA @ 100 mg/mL in methylene chloride. The solution was prepared by dissolving PLGA in pure methylene chloride. Solution 4: PLA-PEG @ 100 mg/mL in methylene chloride. The solution was prepared by dissolving PLA-PEG in pure methylene chloride. Solution 5: Polyvinyl alcohol @ 50 mg/mL and sodium cholate hydrate @ 10 mg/mL in 100 mM pH 8 phosphate buffer.

A primary water-in-oil emulsion was prepared first. W1/O1 was prepared by combining solution 1 (0.2 mL), solution 2 (0.2 mL), solution 3 (0.75 mL), and solution 4 (0.25 mL) in a small pressure tube and sonicating at 50% amplitude for 40 seconds using a Branson Digital Sonifier 250. A secondary emulsion (W1/O1/W2) was then prepared by combining solution 5 (3.0 mL) with the primary W1/O1 emulsion, vortexing for 10 s, and sonicating at 30% amplitude for 60 seconds using the Branson Digital Sonifier 250. The W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of rapamycin in the nanocarrier was determined by HPLC analysis. The amount of protein in the nanocarrier was determined by an o-phthalaldehyde fluorometric assay. The total dry-nanocarrier mass per mL of suspension was determined by a gravimetric method.

| Nanocarrier ID | Effective Diameter (nm) | Rapamycin Content (% w/w) | Protein Content (% w/w) |
| --- | --- | --- | --- |
| 2 | 172 | 7.4 | 7.6 |

Immunization

The purpose of this experiment was to assess the effects of encapsulated ($t^2$SVP) immunosuppressant on ongoing antibody responses by measuring antigen-specific immunoglobulins. One group of animals remained unimmunized as a control. Two groups of animals were immunized using "passive administration” of Ovalbumin or active immunization with OVA and CpG with 3 injections (d0, d14 and d28) followed by an assessment of antibody titers and one or two weeks of rest. Another two groups received the same immunizations but received boosts every 2 weeks at the same time they received the treatment. Each of these groups was split into three subgroups to test the capacity of different treatments to modify the Ig titers induced. A control subgroup did not receive tolerogenic treatment. Two other treatments were applied to the other subgroups including NP carrying just OVA protein or in combination with immunosuppressant.

For immunization, animals received 20 μl/limb of OVA+CpG (12.5 μg OVA+10 μg CpG), both hind limbs s.c. or 25 μg of OVA i.v. in 100 μl. The tolerogenic treatment included administration of 200 μl $t^2$SVP i.v. using 10 μg of OVA. Nanoparticles were provided at 500 μm/ml of OVA content. $t^2$SVP was diluted in such a manner that the same amounts of OVA were injected in all groups Measurement of IgG The level of IgG antibodies were measured. Blocker Casein in PBS (Thermo Fisher, Catalog #37528) was used as diluent. 0.05% Tween-20 in PBS was used as wash buffer, prepared by adding 10 ml of Tween-20 ((Sigma, Catalog #P9416-100 mL) to 2 liters of a 10×PBS stock (PBS: OmniPur® 10×PBS Liquid Concentrate, 4 L, EMD Chemicals, Catalog #6505) and 18 Liters of deionized water.

OVA protein at a stock concentration of 5 mg/ml was used as a coating material. A 1:1000 dilution to 5 μg/ml was used as a working concentration. Each well of the assay plates was coated with 100 μl diluted OVA per well, plates were sealed with sealing film (VWR catalog #60941-120), and incubated overnight at 4° C. Costar9017 96-well Flat bottom plates were used as assay plates, Costar9017.

Low-binding polypropylene 96-well plate or tubes were used as set-up plates, in which samples were prepared before being transferred to the assay plate. The setup plates did not contain any antigen and, therefore, serum antibodies did not bind to the plate during the setup of the samples. Setup plates were used for sample preparation to minimize binding that might occur during preparation or pipetting of samples if an antigen-coated plate was used to prepare the samples. Before preparing samples in the setup plate, wells were covered with diluent to block any non-specific binding and the plate was sealed and incubated at 4° C. overnight.

Assay plates were washed three times with wash buffer, and wash buffer was completely aspirated out of the wells after the last wash. After washing, 300 μl diluent were added to each well of assay plate(s) to block non-specific binding and plates were incubated at least 2 hours at room temperature. Serum samples were prepared in the setup plate at appropriate starting dilutions. Starting dilutions were sometimes also prepared in 1.5 ml tubes using diluent. Appropriate starting dilutions were determined based on previous data, where available. Where no previous data was available, the lowest starting dilution was 1:40. Once diluted, 200 μl of the starting dilution of the serum sample was transferred from to the appropriate well of the setup plate.

An exemplary setup plate layout is described as follows: Columns 2 and 11 contained anti-Ovabumin monoclonal IgG2b isotype (AbCam, ab17291) standard, diluted to 1 μg/mL (1:4000 dilution). Columns 3-10 contained serum samples (at appropriate dilutions). Columns 1 and 12 were not used for samples or standards to avoid any bias of measurements due to edge effect. Instead, columns 1 and 12 contained 200 μl diluent. Normal mouse serum diluted 1:40 was used as a negative control. Anti-mouse IgG2a diluted 1:500 from 0.5 mg/mL stock (BD Bioscience) was used as an isotype control.

Once all samples were prepared in the setup plate, the plate was sealed and stored at 4° C. until blocking of the assay plates was complete. Assay plates were washed three times with wash buffer, and wash buffer was completely aspirated after the last wash. After washing, 100 μL of diluent was added to all wells in rows B-H of the assay plates. A 12-channel pipet was used to transfer samples from the setup plate to the assay plate. Samples were mixed prior to transfer by pipetting 150 μl of diluted serum up and down 3 times. After mixing, 1500 of each sample was transferred from the setup plate and added to row A of the respective assay plate.

Once the starting dilutions of each sample were transferred from the setup plate to row A of the assay plate, serial dilutions were pipetted on the assay plate as follows: 50 μl of each serum sample was removed from row A using 12-channel pipet and mixed with the 100 μl of diluent previously added to each well of row B. This step was repeated down the entire plate. After pipetting the dilution of the final row, 50 μl of fluid was removed from the wells in the final row and discarded, resulting in a final volume of 100 μl in every well of the assay plate. Once sample dilutions were prepared in the assay plates, the plates were incubated at room temperature for at least 2 hours.

After the incubation, plates were washed three times with wash buffer. Detection antibody (Goat anti-mouse anti-IgG, HRP conjugated, AbCam ab98717) was diluted 1:1500 (0.33 μg/mL) in diluent and 100 μl of the diluted antibody was added to each well. Plates were incubated for 1 hour at room temperature and then washed three times with wash buffer, with each washing step including a soak time of at least 30 seconds.

After washing, detection substrate was added to the wells. Equal parts of substrate A and substrate B (BD Biosciences TMB Substrate Reagent Set, catalog #555214) were combined immediately before addition to the assay plates, and 100 μl of the mixed substrate solution were added to each well and incubated for 10 minutes in the dark. The reaction was stopped by adding 50 μl of stop solution (2NH2SO4) to each well after the 10 minute period. The optical density (OD) of the wells was assessed immediately after adding the stop solution on a plate reader at 450 nm with subtraction at 570 nm. Data analysis was performed using Molecular Device's software SoftMax Pro v5.4. In some cases, a four-parameter logistic curve-fit graph was prepared with the dilution on the x-axis (log scale) and the OD value on the y-axis (linear scale), and the half maximum value (EC50) for each sample was determined. The plate template at the top of the layout was adjusted to reflect the dilution of each sample (1 per column).

Results

Figure 4:
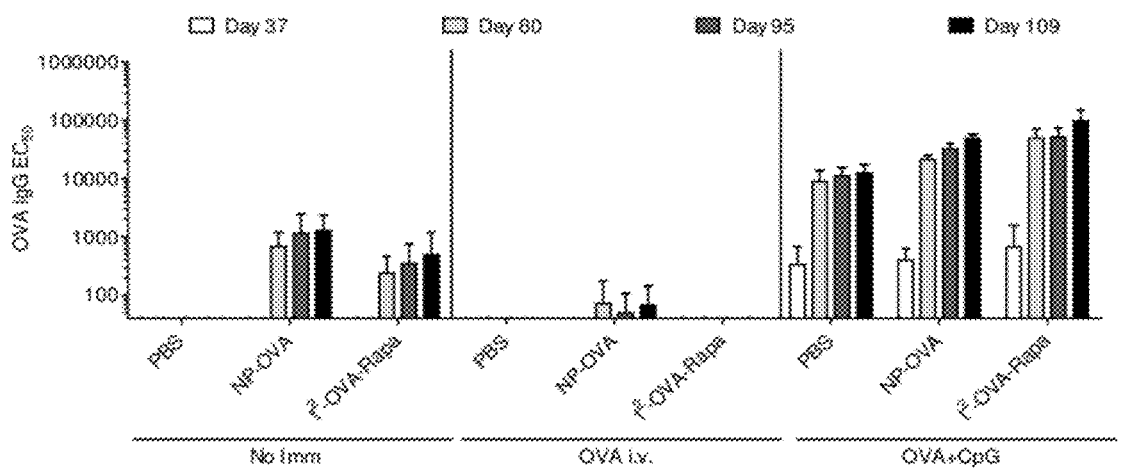
FIG. 4 demonstrates the reduction of anti-OVA IgG antibodies with synthetic nanocarriers that comprise the immunosuppressant rapamycin and ova antigen.

FIG. 4 shows a descrease in antigen-specific antibody production with nanocarriers comprising peptide antigen and immunosuppressant as compared to nanocarriers comprising the peptide alone. Panel 3 shows that the use of a strong immune stimulator, CpG, countered the tolerogenic effects of the synthetic nanocarriers comprising rapamycin in some instances.

Example 14

Tolerogenic Immune Responses with Synthetic Nanocarriers

Materials and Methods

Nanocarriers were prepared as in the above example (Example 13).

Immunization

The purpose of this experiment was to assess the effects of encapsulated ($t^2$SVP) immunosuppressant on emerging antibody responses by measuring antigen-specific immunoglobulins in animals that receive the immunogen and NP-treatment at the same time. One group of animals remained unimmunized as a control (but received the treatment). A second group of animals was immunized using "passive administration" of Ovalbumin, and a third group was immunized with OVA and CpG in the sub-scapular region. Each of these groups were given biweekly injection of nanoparticles (NPs) and anti-OVA Ig levels were monitored on the day previous to the boost. For immunization, animals received 100 μl of OVA+CpG s.c. (subscapular) or 25 μg of OVA i.v. in 1004 Tolerogenic treatment comprised administration of 100 µl t²SVP i.v. Nanocarriers were provided at 5 mg/ml. t2SVP was diluted in such a manner that the same amounts of OVA were injected in all groups. Injections were performed at d0, d14, d28, d42, d56.

Measurement of IgG

The level of IgG antibodies were measured. Blocker Casein in PBS (Thermo Fisher, Catalog #37528) was used as diluent. 0.05% Tween-20 in PBS was used as wash buffer, prepared by adding 10 ml of Tween-20 ((Sigma, Catalog #P9416-100 mL) to 2 liters of a 10×PBS stock (PBS: OmniPur® 10×PBS Liquid Concentrate, 4 L, EMD Chemicals, Catalog #6505) and 18 Liters of deionized water. OVA protein at a stock concentration of 5 mg/ml was used as a coating material. A 1:1000 dilution to 5 µg/ml was used as a working concentration. Each well of the assay plates was coated with 100 µl diluted OVA per well, plates were sealed with sealing film (VWR catalog #60941-120), and incubated overnight at 4° C. Costar9017 96-well Flat bottom plates were used as assay plates, Costar9017.

Low-binding polypropylene 96-well plate or tubes were used as set-up plates, in which samples were prepared before being transferred to the assay plate. The setup plates did not contain any antigen and, therefore, serum antibodies did not bind to the plate during the setup of the samples. Setup plates were used for sample preparation to minimize binding that might occur during preparation or pipetting of samples if an antigen-coated plate was used to prepare the samples. Before preparing samples in the setup plate, wells were covered with diluent to block any non-specific binding and the plate was sealed and incubated at 4° C. overnight.

Assay plates were washed three times with wash buffer, and wash buffer was completely aspirated out of the wells after the last wash. After washing, 300 µl diluent were added to each well of assay plate(s) to block non-specific binding and plates were incubated at least 2 hours at room temperature. Serum samples were prepared in the setup plate at appropriate starting dilutions. Starting dilutions were sometimes also prepared in 1.5 ml tubes using diluent. Appropriate starting dilutions were determined based on previous data, where available. Where no previous data was available, the lowest starting dilution was 1:40. Once diluted, 200 µl of the starting dilution of the serum sample was transferred from to the appropriate well of the setup plate.

An exemplary setup plate layout is described as follows: Columns 2 and 11 contained anti-Ovabumin monoclonal IgG2b isotype (AbCam, ab17291) standard, diluted to 1 µg/mL (1:4000 dilution). Columns 3-10 contained serum samples (at appropriate dilutions). Columns 1 and 12 were not used for samples or standards to avoid any bias of measurements due to edge effect. Instead, columns 1 and 12 contained 200 µl diluent. Normal mouse serum diluted 1:40 was used as a negative control. Anti-mouse IgG2a diluted 1:500 from 0.5 mg/mL stock (BD Bioscience) was used as an isotype control.

Once all samples were prepared in the setup plate, the plate was sealed and stored at 4° C. until blocking of the assay plates was complete. Assay plates were washed three times with wash buffer, and wash buffer was completely aspirated after the last wash. After washing, 100 µL of diluent was added to all wells in rows B-H of the assay plates. A 12-channel pipet was used to transfer samples from the setup plate to the assay plate. Samples were mixed prior to transfer by pipetting 150 µl of diluted serum up and down 3 times. After mixing, 150 µl of each sample was transferred from the setup plate and added to row A of the respective assay plate.

Once the starting dilutions of each sample were transferred from the setup plate to row A of the assay plate, serial dilutions were pipetted on the assay plate as follows: 50 µl of each serum sample was removed from row A using 12-channel pipet and mixed with the 100 µl of diluent previously added to each well of row B. This step was repeated down the entire plate. After pipetting the dilution of the final row, 50 µl of fluid was removed from the wells in the final row and discarded, resulting in a final volume of 100 µl in every well of the assay plate. Once sample dilutions were prepared in the assay plates, the plates were incubated at room temperature for at least 2 hours.

After the incubation, plates were washed three times with wash buffer. Detection antibody (Goat anti-mouse anti-IgG, HRP conjugated, AbCam ab98717) was diluted 1:1500 (0.33 µg/mL) in diluent and 100 µl of the diluted antibody was added to each well. Plates were incubated for 1 hour at room temperature and then washed three times with wash buffer, with each washing step including a soak time of at least 30 seconds.

After washing, detection substrate was added to the wells. Equal parts of substrate A and substrate B (BD Biosciences TMB Substrate Reagent Set, catalog #555214) were combined immediately before addition to the assay plates, and 100 µl of the mixed substrate solution were added to each well and incubated for 10 minutes in the dark. The reaction was stopped by adding 50 µl of stop solution (2NH2SO4) to each well after the 10 minute period. The optical density (OD) of the wells was assessed immediately after adding the stop solution on a plate reader at 450 nm with subtraction at 570 nm. Data analysis was performed using Molecular Device's software SoftMax Pro v5.4. In some cases, a four-parameter logistic curve-fit graph was prepared with the dilution on the x-axis (log scale) and the OD value on the y-axis (linear scale), and the half maximum value (EC50) for each sample was determined. The plate template at the top of the layout was adjusted to reflect the dilution of each sample (1 per column).

Results

Figure 5:
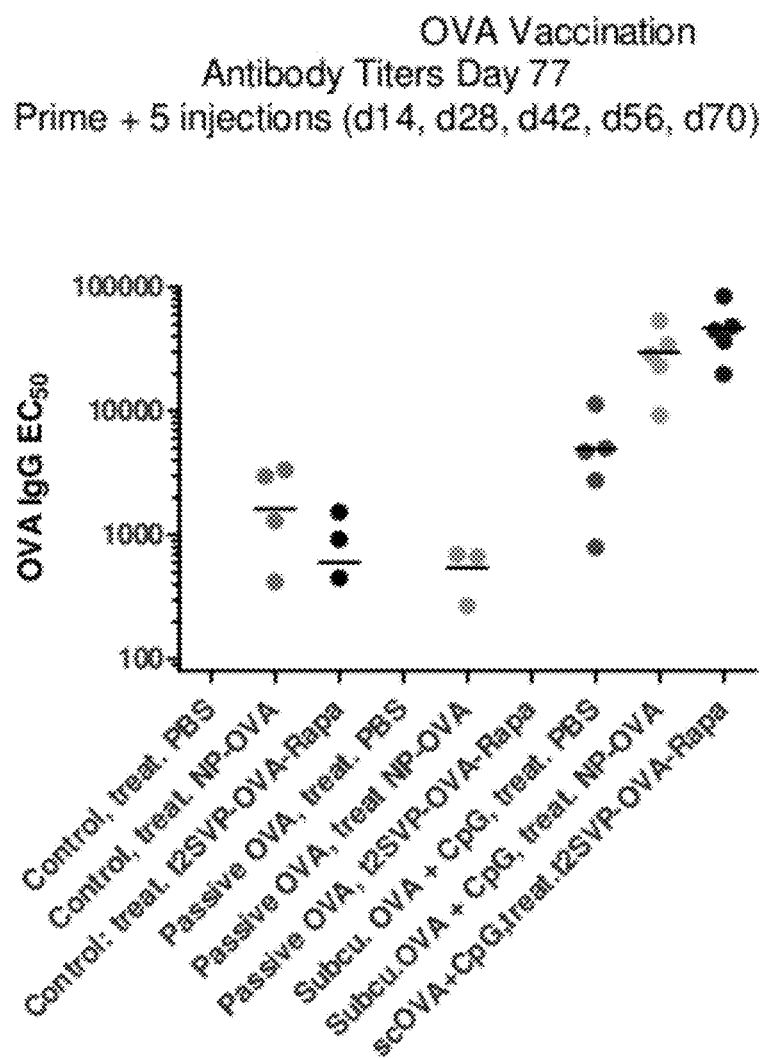
FIG. 5 demonstrates in the control and passive groups the reduction of anti-OVA IgG antibodies with synthetic nanocarriers that comprise the immunosuppressant rapamycin and OVA antigen.

FIG. 5 shows a descrease in antigen-specific antibody production with nanocarriers comprising antigen and immunosuppressant as compared to nanocarriers comprising the antigen alone. Again the data also show that the use of a strong immune stimulator, CpG, countered the tolerogenic effects of the synthetic nanocarriers comprising rapamycin in some instances.

Example 15

Assessing the Effects of Nanocarriers with Antigens and Immunosuppressants on Immune Responses Materials and Methods Nanocarrier 1

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature. Solution 2: PLGA @ 100 mg/mL in methylene chloride. The solution was prepared by dissolving PLGA in pure methylene chloride. Solution 3: PLA-PEG @ 100 mg/mL in methylene chloride. The solution was prepared by dissolving PLA-PEG in pure methylene chloride. Solution 4: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.75 mL), and solution 3 (0.25 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250. The W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of peptide in the nanocarrier was determined by HPLC analysis. The total dry-nanocarrier mass per mL of suspension was determined by a gravimetric method.

| Nanocarrier ID | Effective Diameter (nm) | Peptide Content (% w/w) |
| --- | --- | --- |
| 1 | 234 | 2.1 |

Nanocarrier 2

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). Rapamycin was purchased from TSZ CHEM (185 Wilson Street, Framingham, Mass. 01702; Product Catalogue #R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block copolymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature. Solution 2: Rapamycin @ 50 mg/mL in methylene chloride. The solution was prepared by dissolving rapamycin in pure methylene chloride. Solution 3: PLGA @ 100 mg/mL in methylene chloride. The solution was prepared by dissolving PLGA in pure methylene chloride. Solution 4: PLA-PEG @ 100 mg/mL in methylene chloride. The solution was prepared by dissolving PLA-PEG in pure methylene chloride. Solution 5: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.2 mL), solution 3 (0.75 mL), and solution 4 (0.25 mL) in a small pressure tube and sonicating at 50% amplitude for 40 seconds using a Branson Digital Sonifier 250. A secondary emulsion (W1/O1/W2) was then prepared by combining solution 5 (3.0 mL) with the primary W1/O1 emulsion, vortexing for 10 s, and sonicating at 30% amplitude for 60 seconds using the Branson Digital Sonifier 250. The W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 21,000×g and 4° C. for 45 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amounts of peptide and rapamycin in the nanocarrier were determined by HPLC analysis. The total dry-nanocarrier mass per mL of suspension was determined by a gravimetric method.

| Nanocarrier ID | Effective Diameter (nm) | Rapamycin Content (% w/w) | Peptide Content (% w/w) |
| --- | --- | --- | --- |
| 2 | 227 | 9.0 | 2.5 |

Immunization

Animals received immunization every 2 weeks at the same time they received the treatment. Each of these groups was split into subgroups to test the capacity of different treatments to modify the Ig titers induced. A control subgroup did not receive tolerogenic treatment. Two subgroups received nanocarrier carrying just $OVA_{323-339}$ peptide or in combination with rapamycin.

Immunization was administered via the following routes (values are per animal): 20 µl/limb of OVA+CpG (12.5 µg OVA+10 µg CpG), both hind limbs s.c. Tolerogenic treatments were administered via the following route (values are per animal): 200 µl nanocarriers were provided at 100 µg/ml of $OVA_{323-339}$ content.

Measurement of IgG

The level of IgG antibodies were measured. Blocker Casein in PBS (Thermo Fisher, Catalog #37528) was used as diluent. 0.05% Tween-20 in PBS was used as wash buffer, prepared by adding 10 ml of Tween-20 ((Sigma, Catalog #P9416-100 mL) to 2 liters of a 10×PBS stock (PBS: OmniPur® 10×PBS Liquid Concentrate, 4 L, EMD Chemicals, Catalog #6505) and 18 Liters of deionized water.

OVA protein at a stock concentration of 5 mg/ml was used as a coating material. A 1:1000 dilution to 5 µg/ml was used as a working concentration. Each well of the assay plates was coated with 100 µl diluted OVA per well, plates were sealed with sealing film (VWR catalog #60941-120), and incubated overnight at 4° C. Costar9017 96-well Flat bottom plates were used as assay plates, Costar9017.

Low-binding polypropylene 96-well plate or tubes were used as set-up plates, in which samples were prepared before being transferred to the assay plate. The setup plates did not contain any antigen and, therefore, serum antibodies did not bind to the plate during the setup of the samples. Setup plates were used for sample preparation to minimize binding that might occur during preparation or pipetting of samples if an antigen-coated plate was used to prepare the samples. Before preparing samples in the setup plate, wells were covered with diluent to block any non-specific binding and the plate was sealed and incubated at 4° C. overnight.

Assay plates were washed three times with wash buffer, and wash buffer was completely aspirated out of the wells after the last wash. After washing, 300 µl diluent were added to each well of assay plate(s) to block non-specific binding and plates were incubated at least 2 hours at room temperature. Serum samples were prepared in the setup plate at appropriate starting dilutions. Starting dilutions were sometimes also prepared in 1.5 ml tubes using diluent. Appropriate starting dilutions were determined based on previous data, where available. Where no previous data was available, the lowest starting dilution was 1:40. Once diluted, 200 µl of the starting dilution of the serum sample was transferred from to the appropriate well of the setup plate.

An exemplary setup plate layout is described as follows: Columns 2 and 11 contained anti-Ovabumin monoclonal IgG2b isotype (AbCam, ab17291) standard, diluted to 1 µg/mL (1:4000 dilution). Columns 3-10 contained serum samples (at appropriate dilutions). Columns 1 and 12 were not used for samples or standards to avoid any bias of measurements due to edge effect. Instead, columns 1 and 12 contained 200 µl diluent. Normal mouse serum diluted 1:40 was used as a negative control. Anti-mouse IgG2a diluted 1:500 from 0.5 mg/mL stock (BD Bioscience) was used as an isotype control.

Once all samples were prepared in the setup plate, the plate was sealed and stored at 4° C. until blocking of the assay plates was complete. Assay plates were washed three times with wash buffer, and wash buffer was completely aspirated after the last wash. After washing, 100 µL of diluent was added to all wells in rows B-H of the assay plates. A 12-channel pipet was used to transfer samples from the setup plate to the assay plate. Samples were mixed prior to transfer by pipetting 150 µl of diluted serum up and down 3 times. After mixing, 150 µl of each sample was transferred from the setup plate and added to row A of the respective assay plate.

Once the starting dilutions of each sample were transferred from the setup plate to row A of the assay plate, serial dilutions were pipetted on the assay plate as follows: 50 µl of each serum sample was removed from row A using 12-channel pipet and mixed with the 100 µl of diluent previously added to each well of row B. This step was repeated down the entire plate. After pipetting the dilution of the final row, 50 µl of fluid was removed from the wells in the final row and discarded, resulting in a final volume of 100 µl in every well of the assay plate. Once sample dilutions were prepared in the assay plates, the plates were incubated at room temperature for at least 2 hours.

After the incubation, plates were washed three times with wash buffer. Detection antibody (Goat anti-mouse anti-IgG, HRP conjugated, AbCam ab98717) was diluted 1:1500 (0.33 µg/mL) in diluent and 100 µl of the diluted antibody was added to each well. Plates were incubated for 1 hour at room temperature and then washed three times with wash buffer, with each washing step including a soak time of at least 30 seconds.

After washing, detection substrate was added to the wells. Equal parts of substrate A and substrate B (BD Biosciences TMB Substrate Reagent Set, catalog #555214) were combined immediately before addition to the assay plates, and 100 µl of the mixed substrate solution were added to each well and incubated for 10 minutes in the dark. The reaction was stopped by adding 50 µl of stop solution (2NH2SO4) to each well after the 10 minute period. The optical density (OD) of the wells was assessed immediately after adding the stop solution on a plate reader at 450 nm with subtraction at 570 nm. Data analysis was performed using Molecular Device's software SoftMax Pro v5.4. In some cases, a four-parameter logistic curve-fit graph was prepared with the dilution on the x-axis (log scale) and the OD value on the y-axis (linear scale), and the half maximum value (EC50) for each sample was determined. The plate template at the top of the layout was adjusted to reflect the dilution of each sample (1 per column).

Determination of % OVA+ Dividing B Cells

Ovalbumin+ B-cell division was assessed by flow cytometry. Splenocytes from experimental animals were stained with Cell Tracker Orange (CTO), a thiol-reactive fluorescent probe suitable for long-term cell labeling, and cultured in complete media at 37 C, 5% $CO_2$ with Ovalbumin protein or peptide for 3 days. On day 3 the cells were washed, blocked with anti-CD16/32 antibody and then stained with conjugated antibodies specific to B220 and CD19. Alexa 647 conjugated ovalbumin protein was also incubated with the cells to label Ovalbumin specific BCRs. Those splenocytes that were CD19+ B220+ VA-Alexa647+ were assessed for proliferation by comparing the differential CTO staining. Those that were CTO low were labeled as proliferating Ovalbumin+ B-cells and were compared to the CTO high Ovalbumin+ B-cells to quantify the percentages.

Results

Figure 6:
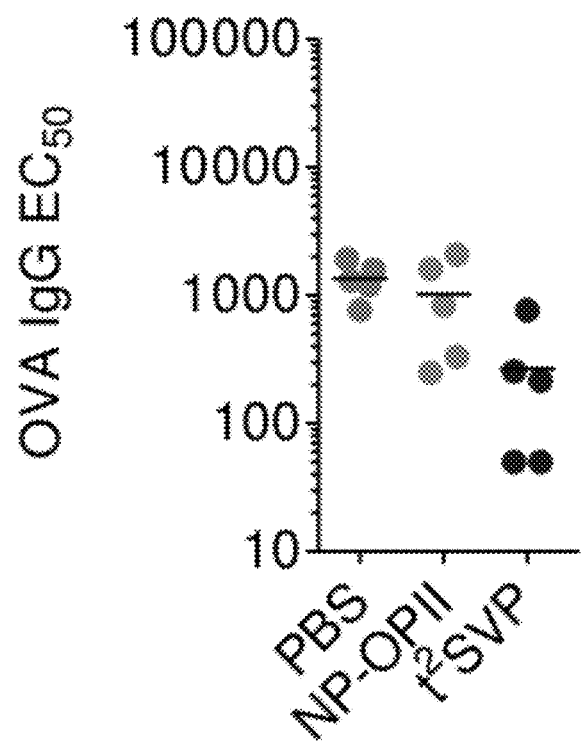
FIG. 6 shows a reduction in antigen-specific IgG levels with the administration of synthetic nanocarriers comprising ova peptide and the immunosuppressant rapamycin.
Figure 7:
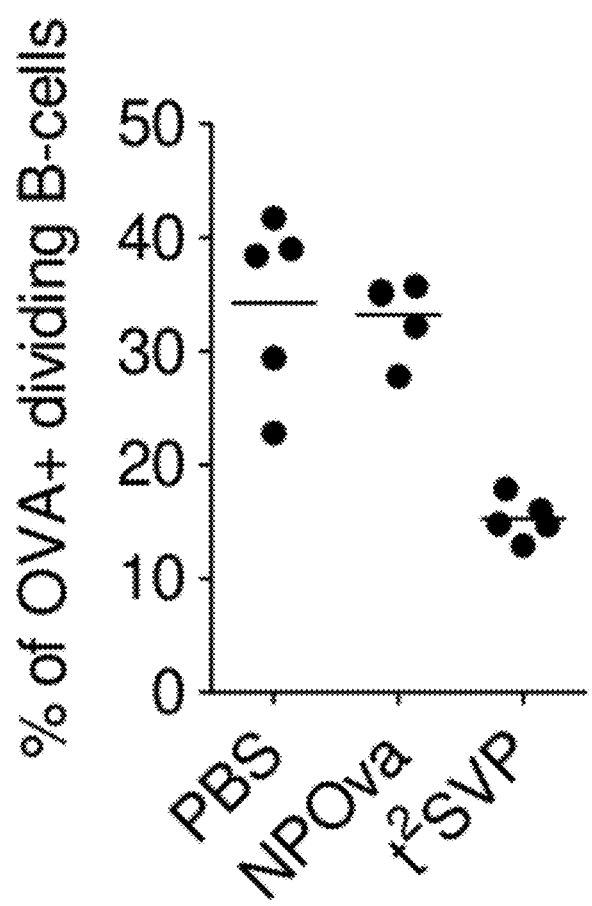
FIG. 7 demonstrates a reduction in the number of antigen-specific B cells with synthetic nanocarriers comprising ova peptide and the immunosuppressant rapamycin.

FIG. 6 shows a reduction in antigen-specific IgG levels with the administration of synthetic nanocarriers comprising ova peptide and the immunosuppressant rapamycin. FIG. 7 also demonstrates a reduction, but in the number of antigen-specific B cells with the synthetic nanocarriers. These results demonstrate the reduction in undesired immune responses with synthetic nanocarriers coupled to ova peptide (comprising an MHC Class II-restricted epitope) and immunosuppressant. There results are relevant in any context where the reduction of antigen-specific B cells would provide a benefit.

Example 16

Assessing the Effects of Nanocarriers with Antigens and Immunosuppressants

Nanocarriers

Nanocarriers were prepared according to methods provided above (Example 15).

Immunization

The nanocarriers were thawed and equilibrated. Initial dilutions constituted a 10× stock solution, and were further diluted to a concentration of 100 µg/ml in $OVA_{323-339}$, or a 1× solution. This 1× solution was used for injections at 200 µl per i.v. injection. Animals were immunized with OVA protein (OVA) and treated with $OVA_{323-339}$ peptide to assess the capacity of nanocarriers to control the immune responses in absence of B cell antigens. Immunization routes were as follows: 10 µg of OVA+4 mg Alum i.p. in 4000 per each Balb/C immunologically naïve female mouse. Experimental groups consisted of 5 animals each. Spleen cells were restimulated with antigen using CFSE or CTO to determine the amount of Ag-specific proliferation.

Levels of Specific Types of Immune Cells

FCS files were analyzed using FlowJo software. 7AAD positive cells (a nuclear dye that label dead cells) positive cells were excluded and cell morphologies dependent on expression of CD4, CD8, Gr-1, F4/80, B220, TCRb and CD11b were quantified.

Gating strategy for T-cell subsets→7AAD− F4/80− GR-1− TCRb+ CD4+/−CD8+/−

Gating strategy for B-cell subsets→7AAD− B220+ TCRb−

Gating strategy for Eosinophils→7AAD− F4/80− Gr-1+ TCRb− CD11b+ Gr-1+

Determination of % Dividing CD4+ T Cells

The frequency of Ovalbumin reactive CD4$^+$ T cells was calculated by way of flow cytometry. Splenocytes from experimental animals were stained with CFSE, a thiol-reactive Fluorescent Probe suitable for long-term cell labeling, and cultured in complete media at 37 C, 5% $CO_2$ with Ovalbumin protein for 3 days. On day 3 the cells were washed, blocked with anti-CD16/32 antibody and then stained with conjugated antibodies specific to TCR CD4 and CD8a. Splenocytes that were TCR+CD4 or TCR+CD8a+ were assessed for proliferation by comparing the differential CFSE staining.

Results

Figure 8:
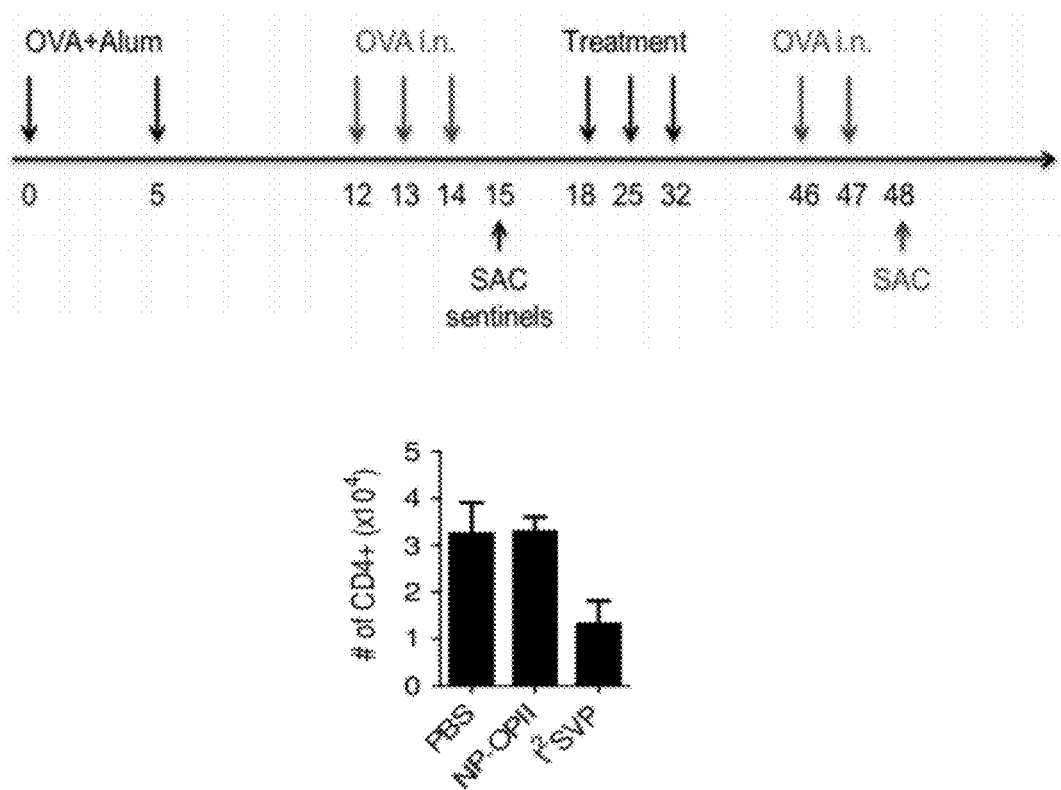
FIG. 8 demonstrates a reduction in the number of CD4+ T cells in lavage samples from asthma model animal subjects treated with synthetic nanocarriers comprising ova peptide and immunosuppressant.
Figure 9:
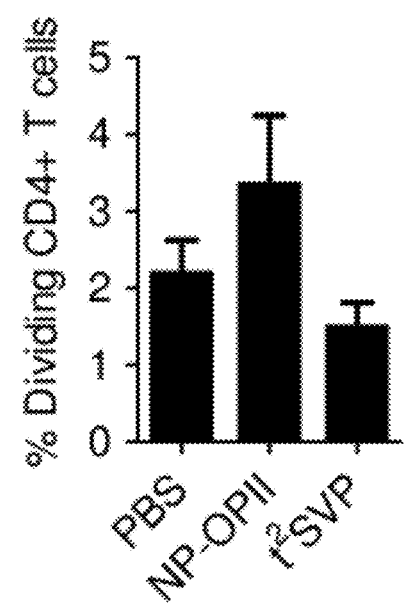
FIG. 9 demonstrates a reduction in the percentage of dividing CD4+ T cells as a result of treatment with synthetic nanocarriers comprising ova peptide and the immunosuppressant rapamycin in asthma model animal subjects.

FIGS. 8 and 9 demonstrate the effectiveness of the nanocarriers in an animal model. Specifically, FIG. 8 demonstrates a reduction in the number of CD4+ T cells in lavage samples from animal subjects treated with synthetic nanocarriers comprising $OVA_{323-339}$ (an MHC Class II-restricted epitope) and immunosuppressant. FIG. 9 demonstrates a reduction in the percentage of dividing CD4+ T cells as a result of the same treatment.

What is claimed is:

1. A composition comprising:
   (i) a first population of polymeric synthetic nanocarriers that are coupled to rapamycin, and
   (ii) a second population of polymeric synthetic nanocarriers that are coupled to therapeutic protein antigen-presenting cell (APC) presentable antigens,
   wherein the load of the rapamycin on average across the first population of polymeric synthetic nanocarriers is at least 2% but no more than 25% (weight/weight),
   wherein the load of the therapeutic protein APC presentable antigens on average across the second population of polymeric synthetic nanocarriers is between 1% and 10% weight/weight,
   wherein at least 75% of the polymeric synthetic nanocarriers of the first population of synthetic nanocarriers have a minimum dimension, obtained using dynamic light scattering, that is is greater than 110 nm,
   and a maximum dimension, obtained using dynamic light scattering, that is equal to or less than 500 nm, and
   wherein the composition is in an amount effective to reduce the generation of an undesired immune response against the therapeutic protein APC presentable antigens.

2. The composition of claim 1, wherein the first population of polymeric synthetic nanocarriers and second population of polymeric synthetic nanocarriers are the same population.

3. The composition of claim 1 or 2, wherein the therapeutic protein APC presentable antigens comprise MHC Class I-restricted and/or MHC Class II-restricted epitopes of a therapeutic protein.

4. The composition of claim 1 or 2, wherein the therapeutic protein APC presentable antigens comprise B cell epitopes of a therapeutic protein.

5. The composition of claim 1 or 2, wherein the therapeutic protein APC presentable antigens comprise substantially no B cell epitopes of a therapeutic protein.

6. The composition of claim 1 or 2, wherein the therapeutic protein APC presentable antigens comprise a therapeutic protein for protein replacement or protein supplementation therapy, or a fragment thereof.

7. The composition of claim 1 or 2, wherein the therapeutic protein APC presentable antigens comprise an infusible or injectable therapeutic protein, an enzyme, an enzyme cofactor, a hormone, a blood or blood coagulation factor, a cytokine, an interferon, a growth factor, a monoclonal antibody, a polyclonal antibody or a protein associated with Pompe's disease, or a fragment thereof.

8. The composition of claim 1 or 2, wherein the first population and/or second population of polymeric nanocarriers comprise polymer that is a non-methoxy-terminated, pluronic polymer.

9. The composition of claim 1 or 2, wherein the first population and/or second population of polymeric nanocarriers comprise a polyester, a polyester coupled to a polyether, polyamino acid, polycarbonate, polyacetal, polyketal, polysaccharide, polyethyloxazoline or polyethyleneimine.

10. The composition of claim 9, wherein the polyester comprises a poly(lactic acid), poly(glycolic acid), poly(lactic-co-glycolic acid) or polycaprolactone.

11. The composition of claim 9, wherein the polymeric nanocarriers comprise a polyester and a polyester coupled to a polyether.

12. The composition of claim 9, wherein the polyether comprises polyethylene glycol or polypropylene glycol.

13. The composition of claim 1 or 2, wherein the aspect ratio of the maximum to minimum dimension of the synthetic nanocarriers of the first population and/or second population is greater than 1:1, 1:1.2, 1:1.5, 1:2, 1:3, 1:5, 1:7 or 1:10.

14. A dosage form comprising the composition of claim 1 or 2.

* * * * *